United States Patent
Tamarkin et al.

(10) Patent No.: US 10,322,186 B2
(45) Date of Patent: *Jun. 18, 2019

(54) TOPICAL TETRACYCLINE COMPOSITIONS

(71) Applicant: Foamix Pharmaceuticals Ltd., Rehovot (IL)

(72) Inventors: Dov Tamarkin, Maccabim (IL); Elana Gazal, Rehovot (IL); Irakliy Papiashvili, Ashkelon (IL); Yohan Hazot, Rehovot (IL); David Schuz, Gimzu (IL); Rita Keynan, Rehovot (IL)

(73) Assignee: FOAMIX PHARMACEUTICALS LTD., Rehovot (IL)

( * ) Notice: Subject to any disclaimer, the term of this patent is extended or adjusted under 35 U.S.C. 154(b) by 0 days.

This patent is subject to a terminal disclaimer.

(21) Appl. No.: 16/235,964

(22) Filed: Dec. 28, 2018

(65) Prior Publication Data

US 2019/0134203 A1    May 9, 2019

Related U.S. Application Data

(63) Continuation of application No. 15/591,733, filed on May 10, 2017, now Pat. No. 10,213,512, which is a
(Continued)

(51) Int. Cl.
| | |
|---|---|
| A61K 8/18 | (2006.01) |
| A61K 35/50 | (2015.01) |
| A61K 31/65 | (2006.01) |
| C07C 50/36 | (2006.01) |
| C07C 237/26 | (2006.01) |
| A61K 47/44 | (2017.01) |
| A61Q 17/04 | (2006.01) |
| A61K 9/00 | (2006.01) |
| A61K 9/12 | (2006.01) |
| A61K 47/24 | (2006.01) |
| A61K 45/06 | (2006.01) |
| A61K 47/10 | (2017.01) |
| A61K 8/36 | (2006.01) |
| A61K 8/34 | (2006.01) |
| A61Q 19/10 | (2006.01) |
| A61Q 19/00 | (2006.01) |
| A61K 8/31 | (2006.01) |
| A61K 47/02 | (2006.01) |
| A61K 31/192 | (2006.01) |
| A61K 31/137 | (2006.01) |
| A61K 47/12 | (2006.01) |
| A61K 31/593 | (2006.01) |

(Continued)

(52) U.S. Cl.
CPC .............. *A61K 47/44* (2013.01); *A61K 8/31* (2013.01); *A61K 8/342* (2013.01); *A61K 8/361* (2013.01); *A61K 9/0014* (2013.01); *A61K 9/0048* (2013.01); *A61K 9/12* (2013.01); *A61K 9/122* (2013.01); *A61K 9/124* (2013.01); *A61K 31/137* (2013.01); *A61K 31/192* (2013.01); *A61K 31/4164* (2013.01); *A61K 31/57* (2013.01); *A61K 31/573* (2013.01); *A61K 31/593* (2013.01); *A61K 31/65* (2013.01); *A61K 45/06* (2013.01); *A61K 47/02* (2013.01); *A61K 47/06* (2013.01); *A61K 47/10* (2013.01); *A61K 47/12* (2013.01); *A61K 47/24* (2013.01); *A61Q 17/04* (2013.01); *A61Q 19/00* (2013.01); *A61Q 19/10* (2013.01); *A61K 2800/31* (2013.01); *A61K 2800/33* (2013.01)

(58) Field of Classification Search
None
See application file for complete search history.

(56) References Cited

U.S. PATENT DOCUMENTS

| | | |
|---|---|---|
| 1,159,250 A | 11/1915 | Moulton |
| 1,666,684 A | 4/1928 | Carstens |
| (Continued) | | |

FOREIGN PATENT DOCUMENTS

| | | |
|---|---|---|
| AU | 198780257 A | 9/1986 |
| AU | 782515 B2 | 12/2005 |
| (Continued) | | |

OTHER PUBLICATIONS

"Everything but the Olive." The Olive Oil Source 1998-2016 [online]. Retrieved from the Internet: http://www.oliveoilsource.com/pageA chemical-characteristics.

(Continued)

*Primary Examiner* — Jeffrey T. Palenik
(74) *Attorney, Agent, or Firm* — Finnegan, Henderson, Farabow, Garrett & Dunner, LLP

(57) ABSTRACT

A topical therapeutic hydrophobic breakable composition includes a carrier comprising (a) about 60% to about 99% by weight of at least one hydrophobic oil; (b) at least one viscosity-modifying agents selected from the group consisting of a fatty alcohol, a fatty acid and a wax; and (c) a tetracycline antibiotic, characterized in that at least part of the tetracycline antibiotic is suspended in the composition; the viscosity of the composition is at least about 30% higher than the viscosity of the carrier without the tetracycline antibiotic; and is higher than the viscosity or the hydrophobic oil and the tetracycline antibiotic without the viscosity modifying agents. The tetracycline is chemically stable in the composition for at least six months; wherein more than about 90% of the tetracycline has not broken down. The composition is packaged as a breakable foam that breaks easily upon application of shear force.

30 Claims, No Drawings

Related U.S. Application Data continuation of application No. 14/595,882, filed on Jan. 13, 2015, now Pat. No. 9,675,700, which is a continuation of application No. 14/469,792, filed on Aug. 27, 2014, now Pat. No. 8,992,896, which is a continuation of application No. 14/327,040, filed on Jul. 9, 2014, now Pat. No. 8,865,139, which is a continuation of application No. 13/499,475, filed as application No. PCT/IB2010/002617 on Oct. 1, 2010, now Pat. No. 8,871,184.

(60) Provisional application No. 61/248,144, filed on Oct. 2, 2009, provisional application No. 61/322,148, filed on Apr. 8, 2010, provisional application No. 61/349,911, filed on May 31, 2010, provisional application No. 61/385,385, filed on Sep. 22, 2010, provisional application No. 61/331,126, filed on May 4, 2010, provisional application No. 61/380,568, filed on Sep. 7, 2010, provisional application No. 61/388,884, filed on Oct. 1, 2010.

(51) Int. Cl.
*A61K 31/573* (2006.01)
*A61K 31/57* (2006.01)
*A61K 31/4164* (2006.01)
*A61K 47/06* (2006.01)

(56) References Cited

U.S. PATENT DOCUMENTS

| | | |
|---|---|---|
| 1,924,972 A | 8/1933 | Beckert |
| 2,085,733 A | 7/1937 | Bird |
| 2,390,921 A | 12/1945 | Clark |
| 2,524,590 A | 10/1950 | Boe |
| 2,586,287 A | 2/1952 | Apperson |
| 2,617,754 A | 11/1952 | Neely |
| 2,767,712 A | 10/1956 | Waterman |
| 2,968,628 A | 1/1961 | Reed |
| 3,004,894 A | 10/1961 | Johnson et al. |
| 3,062,715 A | 11/1962 | Reese et al. |
| 3,067,784 A | 12/1962 | Gorman |
| 3,092,255 A | 6/1963 | Hohman |
| 3,092,555 A | 6/1963 | Horn |
| 3,141,821 A | 7/1964 | Compeau |
| 3,142,420 A | 7/1964 | Gawthrop |
| 3,144,386 A | 8/1964 | Brightenback |
| 3,149,543 A | 9/1964 | Naab |
| 3,154,075 A | 10/1964 | Weckesser |
| 3,178,352 A | 4/1965 | Erickson |
| 3,236,457 A | 2/1966 | Kennedy et al. |
| 3,244,589 A | 4/1966 | Sunnen |
| 3,252,859 A | 5/1966 | Silver |
| 3,261,695 A | 7/1966 | Sienkiewicz |
| 3,263,867 A | 8/1966 | Lehmann |
| 3,263,869 A | 8/1966 | Corsette |
| 3,298,919 A | 1/1967 | Bishop et al. |
| 3,301,444 A | 1/1967 | Wittke |
| 3,303,970 A | 2/1967 | Breslau et al. |
| 3,330,730 A | 7/1967 | Hernandez |
| 3,333,333 A | 8/1967 | Noack |
| 3,334,147 A | 8/1967 | Brunelle et al. |
| 3,342,845 A | 9/1967 | Sayigh et al. |
| 3,346,451 A | 10/1967 | Collins et al. |
| 3,366,494 A | 1/1968 | Bower et al. |
| 3,369,034 A | 2/1968 | Chalmers |
| 3,377,004 A | 4/1968 | Wittke |
| 3,383,280 A | 5/1968 | Kuehns |
| 3,384,541 A | 5/1968 | Clark et al. |
| 3,395,214 A | 7/1968 | Mummert |
| 3,395,215 A | 7/1968 | Schubert |
| 3,401,849 A | 9/1968 | Weber, III |
| 3,419,658 A | 12/1968 | Sanders |
| 3,456,052 A | 7/1969 | Gordon |
| 3,527,559 A | 9/1970 | Sliwinski |
| 3,540,448 A | 11/1970 | Sunnen |
| 3,559,890 A | 2/1971 | Brooks et al. |
| 3,561,262 A | 2/1971 | Borucki |
| 3,563,098 A | 2/1971 | Weber, III |
| 3,574,821 A | 4/1971 | Pfirrmann |
| 3,577,518 A | 5/1971 | Shepherd |
| 3,667,461 A | 6/1972 | Zamarra |
| 3,751,562 A | 8/1973 | Nichols |
| 3,770,648 A | 11/1973 | Mackles |
| 3,787,566 A | 1/1974 | Gauvreau |
| 3,819,524 A | 6/1974 | Schubert et al. |
| 3,824,303 A | 7/1974 | Lanzet et al. |
| 3,841,525 A | 10/1974 | Siegel |
| 3,849,569 A | 11/1974 | Mead |
| 3,849,580 A | 11/1974 | Weinstein et al. |
| 3,865,275 A | 2/1975 | De Nunzio |
| 3,866,800 A | 2/1975 | Schmitt |
| 3,878,118 A | 4/1975 | Watson |
| 3,882,228 A | 5/1975 | Boncey et al. |
| 3,886,084 A | 5/1975 | Vassiliades |
| 3,890,305 A | 6/1975 | Weber et al. |
| 3,912,665 A | 10/1975 | Spitzer et al. |
| 3,912,667 A | 10/1975 | Spitzer et al. |
| 3,923,970 A | 12/1975 | Breuer |
| 3,929,985 A | 12/1975 | Webb, Jr. |
| 3,952,916 A | 4/1976 | Phillips |
| 3,953,591 A | 4/1976 | Snyder |
| 3,959,160 A | 5/1976 | Horsler et al. |
| 3,962,150 A | 6/1976 | Viola |
| 3,963,833 A | 6/1976 | DeSalva et al. |
| 3,966,090 A | 6/1976 | Prussin et al. |
| 3,966,632 A | 6/1976 | Colliopoulos et al. |
| 3,970,219 A | 7/1976 | Spitzer et al. |
| 3,970,584 A | 7/1976 | Hart et al. |
| 3,993,224 A | 11/1976 | Harrison |
| 3,997,467 A | 12/1976 | Jederstrom |
| 4,001,391 A | 1/1977 | Feinstone et al. |
| 4,001,442 A | 1/1977 | Stahlberger et al. |
| 4,018,396 A | 4/1977 | Showmaker et al. |
| 4,019,657 A | 4/1977 | Spitzer et al. |
| 4,052,513 A | 10/1977 | Kaplan |
| 4,083,974 A | 4/1978 | Turi |
| 4,102,995 A | 7/1978 | Hebborn |
| 4,110,426 A | 8/1978 | Barnhurst et al. |
| 4,124,149 A | 11/1978 | Spitzer et al. |
| 4,145,411 A | 3/1979 | Mende |
| 4,151,272 A | 4/1979 | Geary et al. |
| 4,160,827 A | 7/1979 | Cho et al. |
| 4,178,373 A | 12/1979 | Klein et al. |
| 4,213,979 A | 7/1980 | Levine |
| 4,214,000 A | 7/1980 | Papa |
| 4,226,344 A | 10/1980 | Booth et al. |
| 4,229,432 A | 10/1980 | Geria |
| 4,230,701 A | 10/1980 | Holick et al. |
| 4,241,048 A | 12/1980 | Durbak et al. |
| 4,241,149 A | 12/1980 | Labes et al. |
| 4,252,787 A | 2/1981 | Sherman et al. |
| 4,254,104 A | 3/1981 | Suzuki et al. |
| 4,268,499 A | 5/1981 | Keil |
| 4,271,149 A | 6/1981 | Winicov et al. |
| 4,278,206 A | 7/1981 | Prussin |
| 4,292,250 A | 9/1981 | DeLuca et al. |
| 4,292,326 A | 9/1981 | Nazzaro-Porro et al. |
| 4,299,826 A | 11/1981 | Luedders |
| 4,305,936 A | 12/1981 | Klein |
| 4,309,995 A | 1/1982 | Sacco |
| 4,310,510 A | 1/1982 | Sherman et al. |
| 4,323,582 A | 4/1982 | Siegel et al. |
| 4,323,694 A | 4/1982 | Scala, Jr. |
| 4,325,939 A | 4/1982 | Shah |
| 4,329,990 A | 5/1982 | Sneider |
| 4,335,120 A | 6/1982 | Holick et al. |
| 4,338,211 A | 7/1982 | Stiros |
| 4,352,808 A | 10/1982 | Rane et al. |
| 4,363,806 A | 12/1982 | Bergström et al. |
| 4,385,161 A | 5/1983 | Caunt et al. |
| 4,386,104 A | 5/1983 | Nazzaro-Porro |

(56) References Cited

U.S. PATENT DOCUMENTS

| | | |
|---|---|---|
| 4,393,066 A | 7/1983 | Garrett et al. |
| 4,427,670 A | 1/1984 | Ofuchi et al. |
| 4,439,416 A | 3/1984 | Cordon et al. |
| 4,439,441 A | 3/1984 | Hallesy et al. |
| 4,440,320 A | 4/1984 | Wernicke |
| 4,447,486 A | 5/1984 | Hoppe et al. |
| 4,469,674 A | 9/1984 | Shah et al. |
| 4,508,705 A | 4/1985 | Chaudhuri et al. |
| 4,522,948 A | 6/1985 | Walker |
| 4,529,601 A | 7/1985 | Broberg et al. |
| 4,529,605 A | 7/1985 | Lynch et al. |
| 4,552,872 A | 11/1985 | Cooper et al. |
| 4,574,052 A | 3/1986 | Gupte et al. |
| 4,576,961 A | 3/1986 | Lorck et al. |
| 4,595,526 A | 6/1986 | Lai |
| 4,603,812 A | 8/1986 | Stoesser et al. |
| 4,607,101 A | 8/1986 | Bernstein |
| 4,612,193 A | 9/1986 | Gordon et al. |
| 4,627,973 A | 12/1986 | Moran et al. |
| 4,628,063 A | 12/1986 | Haines et al. |
| 4,661,340 A | 4/1987 | Nagy née Kricsfalussy et al. |
| 4,661,524 A | 4/1987 | Thomson et al. |
| 4,672,078 A | 6/1987 | Sakai et al. |
| 4,673,569 A | 6/1987 | Shernov et al. |
| 4,678,463 A | 7/1987 | Millar |
| 4,701,320 A | 10/1987 | Hasegawa et al. |
| 4,725,609 A | 2/1988 | Kull, Jr. et al. |
| 4,738,396 A | 4/1988 | Doi et al. |
| 4,741,855 A | 5/1988 | Grote et al. |
| 4,752,465 A | 6/1988 | Mackles |
| 4,770,634 A | 9/1988 | Pellico |
| 4,772,427 A | 9/1988 | Dawson |
| 4,780,309 A | 10/1988 | Geria et al. |
| 4,784,842 A | 11/1988 | London et al. |
| 4,792,062 A | 12/1988 | Goncalves |
| 4,798,682 A | 1/1989 | Ansmann |
| 4,804,674 A | 2/1989 | Curtis-Prior et al. |
| 4,806,262 A | 2/1989 | Snyder |
| 4,808,388 A | 2/1989 | Beutler et al. |
| 4,822,613 A | 4/1989 | Rodero |
| 4,822,614 A | 4/1989 | Rodero |
| 4,826,048 A | 5/1989 | Skorka et al. |
| 4,827,378 A | 5/1989 | Gillan et al. |
| 4,828,837 A | 5/1989 | Uster et al. |
| 4,836,217 A | 6/1989 | Fischer et al. |
| 4,837,019 A | 6/1989 | Georgalas et al. |
| 4,837,378 A | 6/1989 | Borgman |
| 4,844,902 A | 7/1989 | Grohe |
| 4,847,068 A | 7/1989 | Dole et al. |
| 4,849,117 A | 7/1989 | Bronner et al. |
| 4,849,211 A | 7/1989 | Schrauzer |
| 4,851,154 A | 7/1989 | Grollier et al. |
| 4,855,294 A | 8/1989 | Patel et al. |
| 4,863,900 A | 9/1989 | Pollock et al. |
| 4,867,967 A | 9/1989 | Crutcher |
| 4,873,078 A | 10/1989 | Edmundson et al. |
| 4,874,794 A | 10/1989 | Katz |
| 4,876,083 A | 10/1989 | Grollier et al. |
| 4,877,805 A | 10/1989 | Kligman |
| 4,885,282 A | 12/1989 | Thornfeldt |
| 4,897,262 A | 1/1990 | Nandagiri et al. |
| 4,902,281 A | 2/1990 | Avoy |
| 4,906,453 A | 3/1990 | Tsoucalas |
| 4,913,893 A | 4/1990 | Varco et al. |
| 4,919,934 A | 4/1990 | Deckner et al. |
| 4,933,330 A | 6/1990 | Jorgensen et al. |
| 4,950,420 A | 8/1990 | Svarz |
| 4,954,487 A | 9/1990 | Cooper et al. |
| 4,956,049 A | 9/1990 | Bernheim et al. |
| 4,957,732 A | 9/1990 | Grollier et al. |
| 4,963,351 A | 10/1990 | Weston |
| 4,965,063 A | 10/1990 | Casey et al. |
| 4,966,779 A | 10/1990 | Kirk |
| 4,970,067 A | 11/1990 | Panandiker et al. |
| 4,975,466 A | 12/1990 | Bottcher et al. |
| 4,981,367 A | 1/1991 | Brazelton |
| 4,981,677 A | 1/1991 | Thau |
| 4,981,679 A | 1/1991 | Briggs et al. |
| 4,981,845 A | 1/1991 | Pereira et al. |
| 4,985,459 A | 1/1991 | Sunshine et al. |
| 4,992,478 A | 2/1991 | Geria |
| 4,993,496 A | 2/1991 | Riedle et al. |
| 4,996,193 A | 2/1991 | Hewitt et al. |
| 5,002,540 A | 3/1991 | Brodman et al. |
| 5,002,680 A | 3/1991 | Schmidt et al. |
| 5,007,556 A | 4/1991 | Lover |
| 5,013,297 A | 5/1991 | Cattanach |
| 5,015,471 A | 5/1991 | Birtwistle et al. |
| 5,019,375 A | 5/1991 | Tanner et al. |
| 5,034,220 A | 7/1991 | Helioff et al. |
| 5,035,895 A | 7/1991 | Shibusawa et al. |
| 5,053,228 A | 10/1991 | Mori et al. |
| 5,071,648 A | 12/1991 | Rosenblatt |
| 5,071,881 A | 12/1991 | Parfondry et al. |
| 5,073,371 A | 12/1991 | Turner et al. |
| 5,082,651 A | 1/1992 | Healey et al. |
| 5,087,618 A | 2/1992 | Bodor |
| 5,089,252 A | 2/1992 | Grollier et al. |
| 5,091,111 A | 2/1992 | Neumiller |
| 5,094,853 A | 3/1992 | Hagarty |
| 5,100,917 A | 3/1992 | Flynn et al. |
| 5,104,645 A | 4/1992 | Cardin et al. |
| 5,112,359 A | 5/1992 | Murphy et al. |
| 5,114,718 A | 5/1992 | Damani |
| 5,122,519 A | 6/1992 | Ritter |
| 5,130,121 A | 7/1992 | Kopolow et al. |
| 5,133,972 A | 7/1992 | Ferrini et al. |
| 5,135,915 A | 8/1992 | Czarniecki et al. |
| 5,137,714 A | 8/1992 | Scott |
| 5,143,717 A | 9/1992 | Davis |
| 5,156,765 A | 10/1992 | Smrt |
| 5,160,665 A | 11/1992 | Owada et al. |
| 5,164,357 A | 11/1992 | Bartman et al. |
| 5,164,367 A | 11/1992 | Pickart |
| 5,167,950 A | 12/1992 | Lins |
| 5,171,577 A | 12/1992 | Griat et al. |
| 5,196,405 A | 3/1993 | Packman |
| 5,204,090 A | 4/1993 | Han |
| 5,204,093 A | 4/1993 | Victor |
| 5,208,031 A | 5/1993 | Kelly |
| 5,217,707 A | 6/1993 | Szabo et al. |
| 5,219,877 A | 6/1993 | Shah et al. |
| 5,221,530 A | 6/1993 | Janchitraponvej et al. |
| 5,221,534 A | 6/1993 | DesLauriers et al. |
| 5,221,696 A | 6/1993 | Ke et al. |
| 5,230,897 A | 7/1993 | Griffin et al. |
| 5,236,707 A | 8/1993 | Stewart, II |
| 5,252,246 A | 10/1993 | Ding et al. |
| 5,254,334 A | 10/1993 | Ramirez et al. |
| 5,262,407 A | 11/1993 | Leveque et al. |
| 5,266,592 A | 11/1993 | Grub et al. |
| 5,279,819 A | 1/1994 | Hayes |
| 5,286,475 A | 2/1994 | Louvet et al. |
| 5,294,365 A | 3/1994 | Welch et al. |
| 5,300,286 A | 4/1994 | Gee |
| 5,301,841 A | 4/1994 | Fuchs |
| 5,308,643 A | 5/1994 | Osipow et al. |
| 5,314,904 A | 5/1994 | Egidio et al. |
| 5,318,774 A | 6/1994 | Alban et al. |
| 5,322,683 A | 6/1994 | Mackles et al. |
| 5,326,557 A | 7/1994 | Glover et al. |
| 5,344,051 A | 9/1994 | Brown |
| 5,346,135 A | 9/1994 | Vincent |
| 5,352,437 A | 10/1994 | Nakagawa et al. |
| 5,369,131 A | 11/1994 | Poli et al. |
| 5,378,451 A | 1/1995 | Gorman et al. |
| 5,378,730 A | 1/1995 | Lee et al. |
| 5,380,761 A | 1/1995 | Szabo et al. |
| 5,384,308 A | 1/1995 | Henkin |
| 5,385,943 A | 1/1995 | Nazzaro-Porro |
| 5,389,305 A | 2/1995 | Repinec et al. |
| 5,389,676 A | 2/1995 | Michaels |
| 5,397,312 A | 3/1995 | Rademaker et al. |
| 5,398,846 A | 3/1995 | Corba et al. |

(56) References Cited

U.S. PATENT DOCUMENTS

| | | |
|---|---|---|
| 5,399,205 A | 3/1995 | Shinohara et al. |
| 5,411,992 A | 5/1995 | Eini et al. |
| 5,422,361 A | 6/1995 | Munayyer et al. |
| 5,429,815 A | 7/1995 | Faryniarz et al. |
| 5,435,996 A | 7/1995 | Glover et al. |
| 5,439,670 A | 8/1995 | Purewal et al. |
| 5,439,682 A | 8/1995 | Wivell et al. |
| 5,447,725 A | 9/1995 | Damani et al. |
| 5,449,520 A | 9/1995 | Frigerio et al. |
| 5,451,404 A | 9/1995 | Furman |
| 5,482,965 A | 1/1996 | Rajadhyaksha |
| 5,491,245 A | 2/1996 | Gruning et al. |
| 5,500,211 A | 3/1996 | George et al. |
| 5,508,033 A | 4/1996 | Briand et al. |
| 5,512,555 A | 4/1996 | Waldstreicher |
| 5,514,367 A | 5/1996 | Lentini et al. |
| 5,514,369 A | 5/1996 | Salka et al. |
| 5,520,918 A | 5/1996 | Smith |
| 5,523,078 A | 6/1996 | Baylin |
| 5,527,534 A | 6/1996 | Myhling |
| 5,527,822 A | 6/1996 | Scheiner |
| 5,529,770 A | 6/1996 | McKinzie et al. |
| 5,531,703 A | 7/1996 | Skwarek et al. |
| 5,534,261 A | 7/1996 | Rodgers et al. |
| 5,536,743 A | 7/1996 | Borgman |
| 5,540,853 A | 7/1996 | Trinh et al. |
| 5,545,401 A | 8/1996 | Shanbrom |
| 5,547,989 A | 8/1996 | Chamness |
| 5,558,872 A | 9/1996 | Jones et al. |
| 5,560,859 A | 10/1996 | Hartmann et al. |
| 5,567,420 A | 10/1996 | McEleney et al. |
| 5,576,016 A | 11/1996 | Amselem et al. |
| 5,578,315 A | 11/1996 | Chien et al. |
| 5,585,104 A | 12/1996 | Ha et al. |
| 5,589,157 A | 12/1996 | Hatfield |
| 5,589,515 A | 12/1996 | Suzuki et al. |
| 5,597,560 A | 1/1997 | Bergamini et al. |
| 5,603,940 A | 2/1997 | Candau et al. |
| 5,605,679 A | 2/1997 | Hansenne et al. |
| 5,608,119 A | 3/1997 | Amano et al. |
| 5,611,463 A | 3/1997 | Favre |
| 5,612,056 A | 3/1997 | Jenner et al. |
| 5,613,583 A | 3/1997 | Kono et al. |
| 5,613,623 A | 3/1997 | Hildebrandt |
| 5,614,171 A | 3/1997 | Clavenna et al. |
| 5,614,178 A | 3/1997 | Bloom et al. |
| 5,618,516 A | 4/1997 | Clavenna et al. |
| 5,635,469 A | 6/1997 | Fowler et al. |
| 5,641,480 A | 6/1997 | Vermeer |
| 5,643,600 A | 7/1997 | Mathur |
| 5,645,842 A | 7/1997 | Gruning et al. |
| 5,648,380 A | 7/1997 | Martin |
| 5,650,554 A | 7/1997 | Moloney |
| 5,658,575 A | 8/1997 | Ribier et al. |
| 5,658,749 A | 8/1997 | Thornton |
| 5,658,956 A | 8/1997 | Martin et al. |
| 5,663,208 A | 9/1997 | Martin |
| 5,672,634 A | 9/1997 | Tseng et al. |
| 5,679,324 A | 10/1997 | Lisboa et al. |
| 5,683,710 A | 11/1997 | Akemi et al. |
| 5,686,088 A | 11/1997 | Mitra et al. |
| 5,693,258 A | 12/1997 | Tonomura et al. |
| 5,695,551 A | 12/1997 | Buckingham et al. |
| 5,695,747 A | 12/1997 | Forestier et al. |
| 5,700,396 A | 12/1997 | Suzuki et al. |
| 5,705,472 A | 1/1998 | Hayes et al. |
| 5,716,611 A | 2/1998 | Oshlack et al. |
| 5,716,621 A | 2/1998 | Bello |
| 5,719,122 A | 2/1998 | Chiodini et al. |
| 5,719,197 A | 2/1998 | Kanios et al. |
| 5,725,872 A | 3/1998 | Stamm et al. |
| 5,725,874 A | 3/1998 | Oda |
| 5,730,964 A | 3/1998 | Waldstreicher |
| 5,733,558 A | 3/1998 | Breton et al. |
| 5,733,572 A | 3/1998 | Unger et al. |
| 5,747,049 A | 5/1998 | Tominaga |
| 5,753,241 A | 5/1998 | Ribier et al. |
| 5,753,245 A | 5/1998 | Fowler et al. |
| 5,753,270 A | 5/1998 | Beauchamp et al. |
| 5,759,520 A | 6/1998 | Sachetto |
| 5,759,579 A | 6/1998 | Singh et al. |
| 5,767,104 A | 6/1998 | Bar-Shalom et al. |
| 5,773,410 A | 6/1998 | Yamamoto |
| 5,783,202 A | 7/1998 | Tomlinson et al. |
| 5,788,664 A | 8/1998 | Scalise |
| 5,792,448 A | 8/1998 | Dubief et al. |
| 5,792,922 A | 8/1998 | Moloney et al. |
| 5,797,955 A | 8/1998 | Walters |
| 5,804,546 A | 9/1998 | Hall et al. |
| 5,807,571 A | 9/1998 | List |
| 5,817,322 A | 10/1998 | Xu et al. |
| 5,824,650 A | 10/1998 | De Lacharriere et al. |
| 5,833,960 A | 11/1998 | Gers-Barlag et al. |
| 5,833,961 A | 11/1998 | Siegfried et al. |
| 5,837,270 A | 11/1998 | Burgess |
| 5,840,744 A | 11/1998 | Borgman |
| 5,840,771 A | 11/1998 | Oldham et al. |
| 5,843,411 A | 12/1998 | Hernandez et al. |
| 5,846,983 A | 12/1998 | Sandborn et al. |
| 5,849,042 A | 12/1998 | Lim et al. |
| 5,854,246 A | 12/1998 | Francois et al. |
| 5,856,452 A | 1/1999 | Moloney et al. |
| 5,858,371 A | 1/1999 | Singh et al. |
| 5,865,347 A | 2/1999 | Welschoff |
| 5,866,040 A | 2/1999 | Nakama et al. |
| 5,869,529 A | 2/1999 | Sintov et al. |
| 5,871,720 A | 2/1999 | Gutierrez et al. |
| 5,877,216 A | 3/1999 | Place et al. |
| 5,879,469 A | 3/1999 | Avram et al. |
| 5,881,493 A | 3/1999 | Restive |
| 5,885,581 A | 3/1999 | Massand |
| 5,889,028 A | 3/1999 | Sandborn et al. |
| 5,889,054 A | 3/1999 | Yu et al. |
| 5,891,458 A | 4/1999 | Britton et al. |
| 5,902,574 A | 5/1999 | Stoner et al. |
| 5,902,789 A | 5/1999 | Stoltz |
| 5,905,092 A | 5/1999 | Osborne et al. |
| 5,910,382 A | 6/1999 | Goodenough et al. |
| 5,911,981 A | 6/1999 | Dahms et al. |
| 5,912,007 A | 6/1999 | Pan et al. |
| 5,914,122 A | 6/1999 | Otterbeck et al. |
| 5,914,310 A | 6/1999 | Li et al. |
| 5,919,830 A | 7/1999 | Gopalkrishnan et al. |
| 5,922,331 A | 7/1999 | Mausner |
| 5,925,669 A | 7/1999 | Katz et al. |
| 5,939,376 A | 8/1999 | Durbut et al. |
| 5,948,682 A | 9/1999 | Moloney |
| 5,951,544 A | 9/1999 | Konwitz |
| 5,951,989 A | 9/1999 | Heymann |
| 5,951,993 A | 9/1999 | Scholz et al. |
| 5,952,373 A | 9/1999 | Lanzendorfer et al. |
| 5,952,392 A | 9/1999 | Katz et al. |
| 5,955,414 A | 9/1999 | Brown et al. |
| 5,959,161 A | 9/1999 | Kenmochi et al. |
| 5,961,957 A | 10/1999 | McAnalley |
| 5,961,998 A | 10/1999 | Arnaud et al. |
| 5,972,310 A | 10/1999 | Sachetto |
| 5,976,555 A | 11/1999 | Liu et al. |
| 5,980,904 A | 11/1999 | Leverett et al. |
| 5,990,100 A | 11/1999 | Rosenberg et al. |
| 5,993,846 A | 11/1999 | Friedman et al. |
| 6,001,341 A | 12/1999 | Genova et al. |
| 6,006,948 A | 12/1999 | Auer |
| 6,017,912 A | 1/2000 | Bussell |
| 6,019,967 A | 2/2000 | Breton et al. |
| 6,024,942 A | 2/2000 | Tanner et al. |
| 6,030,630 A | 2/2000 | Fleury et al. |
| 6,033,647 A | 3/2000 | Touzan et al. |
| 6,039,936 A | 3/2000 | Restle et al. |
| 6,042,848 A | 3/2000 | Lawyer et al. |
| 6,045,779 A | 4/2000 | Mueller et al. |
| 6,060,041 A | 5/2000 | Candau et al. |
| 6,071,536 A | 6/2000 | Suzuki et al. |
| 6,071,541 A | 6/2000 | Murad |

(56) References Cited

U.S. PATENT DOCUMENTS

| | | | |
|---|---|---|---|
| 6,075,056 | A | 6/2000 | Quigley, Jr. et al. |
| 6,080,394 | A | 6/2000 | Lin et al. |
| 6,087,310 | A | 7/2000 | Heinkel |
| 6,087,317 | A | 7/2000 | Gee |
| 6,090,772 | A | 7/2000 | Kaiser et al. |
| 6,093,408 | A | 7/2000 | Hasenoehrl et al. |
| 6,096,756 | A | 8/2000 | Crain et al. |
| 6,110,477 | A | 8/2000 | Hernandez et al. |
| 6,110,966 | A | 8/2000 | Pollock |
| 6,113,888 | A | 9/2000 | Castro et al. |
| 6,116,466 | A | 9/2000 | Gueret |
| 6,121,210 | A | 9/2000 | Taylor |
| 6,126,920 | A | 10/2000 | Jones et al. |
| 6,133,327 | A | 10/2000 | Kimura et al. |
| 6,140,355 | A | 10/2000 | Egidio et al. |
| 6,146,645 | A | 11/2000 | Deckers et al. |
| 6,146,664 | A | 11/2000 | Siddiqui |
| 6,162,834 | A | 12/2000 | Sebillotte-Arnaud et al. |
| 6,165,455 | A | 12/2000 | Torgerson et al. |
| 6,168,576 | B1 | 1/2001 | Reynolds |
| 6,171,347 | B1 | 1/2001 | Kunz et al. |
| 6,180,662 | B1 | 1/2001 | Lanzendörfer et al. |
| 6,180,669 | B1 | 1/2001 | Tamarkin |
| 6,183,762 | B1 | 2/2001 | Deckers et al. |
| 6,186,367 | B1 | 2/2001 | Harrold |
| 6,187,290 | B1 | 2/2001 | Gilchrist et al. |
| 6,189,810 | B1 | 2/2001 | Nerushai et al. |
| 6,190,365 | B1 | 2/2001 | Abbott et al. |
| 6,204,285 | B1 | 3/2001 | Fabiano et al. |
| 6,210,656 | B1 | 4/2001 | Touzan et al. |
| 6,210,742 | B1 | 4/2001 | Deckers et al. |
| 6,214,318 | B1 | 4/2001 | Osipow et al. |
| 6,214,788 | B1 | 4/2001 | Velazco et al. |
| 6,217,887 | B1 | 4/2001 | Beerse et al. |
| 6,221,381 | B1 | 4/2001 | Shelford et al. |
| 6,221,823 | B1 | 4/2001 | Crisanti et al. |
| 6,224,888 | B1 | 5/2001 | Vatter et al. |
| 6,231,837 | B1 | 5/2001 | Stroud et al. |
| 6,232,315 | B1 | 5/2001 | Shafer et al. |
| 6,241,971 | B1 | 6/2001 | Fox et al. |
| 6,251,369 | B1 | 6/2001 | Stoltz |
| 6,258,374 | B1 | 7/2001 | Friess et al. |
| 6,261,544 | B1 | 7/2001 | Coury et al. |
| 6,264,964 | B1 | 7/2001 | Mohammadi |
| 6,270,781 | B1 | 8/2001 | Gehlsen |
| 6,271,295 | B1 | 8/2001 | Powell et al. |
| 6,274,150 | B1 | 8/2001 | Simonnet et al. |
| 6,283,336 | B1 | 9/2001 | Dwyer et al. |
| 6,284,802 | B1 | 9/2001 | Bissett et al. |
| 6,287,546 | B1 | 9/2001 | Reich et al. |
| 6,294,550 | B1 | 9/2001 | Place et al. |
| 6,299,023 | B1 | 10/2001 | Arnone |
| 6,299,032 | B1 | 10/2001 | Hamilton |
| 6,299,900 | B1 | 10/2001 | Reed et al. |
| 6,305,578 | B1 | 10/2001 | Hildebrandt et al. |
| 6,306,841 | B1 | 10/2001 | Place et al. |
| 6,308,863 | B1 | 10/2001 | Harman |
| 6,319,913 | B1 | 11/2001 | Mak et al. |
| 6,328,950 | B1 | 12/2001 | Franzke et al. |
| 6,328,982 | B1 | 12/2001 | Shiroyama et al. |
| 6,333,362 | B1 | 12/2001 | Lorant |
| 6,335,022 | B1 | 1/2002 | Simonnet et al. |
| 6,341,717 | B2 | 1/2002 | Auer |
| 6,344,218 | B1 | 2/2002 | Dodd et al. |
| 6,348,229 | B1 | 2/2002 | Eini et al. |
| 6,352,727 | B1 | 3/2002 | Takahashi |
| 6,355,230 | B2 | 3/2002 | Gers-Barlag et al. |
| 6,358,541 | B1 | 3/2002 | Goodman |
| 6,358,924 | B1 | 3/2002 | Hoffmann |
| 6,364,854 | B1 | 4/2002 | Ferrer et al. |
| 6,372,234 | B1 | 4/2002 | Deckers et al. |
| 6,375,936 | B1 | 4/2002 | Allard et al. |
| 6,375,960 | B1 | 4/2002 | Simonnet et al. |
| 6,383,471 | B1 | 5/2002 | Chen et al. |
| 6,395,258 | B1 | 5/2002 | Steer |
| 6,395,300 | B1 | 5/2002 | Straub et al. |
| 6,403,061 | B1 | 6/2002 | Candau et al. |
| 6,403,069 | B1 | 6/2002 | Chopra et al. |
| 6,410,036 | B1 | 6/2002 | De Rosa et al. |
| 6,423,323 | B2 | 7/2002 | Neubourg |
| 6,423,329 | B1 | 7/2002 | Sine et al. |
| 6,428,772 | B1 | 8/2002 | Singh et al. |
| 6,433,003 | B1 | 8/2002 | Bobrove et al. |
| 6,433,024 | B1 | 8/2002 | Popp et al. |
| 6,433,033 | B1 | 8/2002 | Isobe et al. |
| 6,433,068 | B1 | 8/2002 | Morrison et al. |
| 6,437,006 | B1 | 8/2002 | Yoon et al. |
| 6,440,429 | B1 | 8/2002 | Torizuka et al. |
| 6,447,801 | B1 | 9/2002 | Salafsky et al. |
| 6,451,777 | B1 | 9/2002 | Bradbury et al. |
| 6,455,076 | B1 | 9/2002 | Hahn et al. |
| 6,468,989 | B1 | 10/2002 | Chang et al. |
| 6,479,058 | B1 | 11/2002 | McCadden |
| 6,479,060 | B1 | 11/2002 | Jones et al. |
| 6,479,532 | B1 | 11/2002 | Kamimura et al. |
| 6,482,810 | B1 | 11/2002 | Brem et al. |
| 6,486,168 | B1 | 11/2002 | Skwierczynski et al. |
| 6,488,947 | B1 | 12/2002 | Bekele |
| 6,511,655 | B1 | 1/2003 | Muller et al. |
| 6,514,487 | B1 | 2/2003 | Barr |
| 6,524,594 | B1 | 2/2003 | Santora et al. |
| 6,531,118 | B1 | 3/2003 | Gonzalez et al. |
| 6,534,455 | B1 | 3/2003 | Maurin et al. |
| 6,536,629 | B2 | 3/2003 | van der Heijden |
| 6,544,530 | B1 | 4/2003 | Friedman |
| 6,544,562 | B2 | 4/2003 | Singh et al. |
| 6,547,063 | B1 | 4/2003 | Zaveri et al. |
| 6,548,074 | B1 | 4/2003 | Mohammadi |
| 6,551,604 | B1 | 4/2003 | Beck et al. |
| 6,562,355 | B1 | 5/2003 | Renault |
| 6,566,350 | B2 | 5/2003 | Ono et al. |
| 6,582,679 | B2 | 6/2003 | Stein et al. |
| 6,582,710 | B2 | 6/2003 | Deckers et al. |
| 6,589,509 | B2 | 7/2003 | Keller et al. |
| 6,596,287 | B2 | 7/2003 | Deckers et al. |
| 6,599,513 | B2 | 7/2003 | Deckers et al. |
| 6,607,716 | B1 | 8/2003 | Smith et al. |
| 6,610,315 | B2 | 8/2003 | Scholz et al. |
| 6,620,773 | B1 | 9/2003 | Stork et al. |
| 6,638,981 | B2 | 10/2003 | Williams et al. |
| 6,649,571 | B1 | 11/2003 | Morgan |
| 6,649,574 | B2 | 11/2003 | Cardis et al. |
| 6,672,483 | B1 | 1/2004 | Roy |
| 6,682,726 | B2 | 1/2004 | Marchesi et al. |
| 6,682,750 | B2 | 1/2004 | Loeffler et al. |
| 6,691,898 | B2 | 2/2004 | Hurray et al. |
| 6,706,290 | B1 | 3/2004 | Kajander et al. |
| 6,709,663 | B2 | 3/2004 | Espinoza |
| 6,723,309 | B1 | 4/2004 | Deane |
| 6,730,288 | B1 | 5/2004 | Abram |
| 6,736,860 | B2 | 5/2004 | Patel et al. |
| 6,753,000 | B2 | 6/2004 | Breton et al. |
| 6,753,013 | B1 | 6/2004 | Didriksen et al. |
| 6,753,167 | B2 | 6/2004 | Moloney et al. |
| 6,762,158 | B2 | 7/2004 | Lukenbach et al. |
| 6,765,001 | B2 | 7/2004 | Gans et al. |
| 6,774,114 | B2 | 8/2004 | Castiel et al. |
| 6,777,591 | B1 | 8/2004 | Chaudhary et al. |
| 6,790,435 | B1 | 9/2004 | Ma et al. |
| 6,796,973 | B1 | 9/2004 | Contente et al. |
| RE38,623 | E | 10/2004 | Hernandez et al. |
| 6,811,767 | B1 | 11/2004 | Bosch et al. |
| 6,834,778 | B2 | 12/2004 | Jinbo et al. |
| 6,841,547 | B2 | 1/2005 | Brown et al. |
| 6,843,390 | B1 | 1/2005 | Bristor |
| 6,875,438 | B2 | 4/2005 | Kraemer et al. |
| 6,881,271 | B2 | 4/2005 | Ochiai |
| 6,890,567 | B2 | 5/2005 | Nakatsu et al. |
| 6,897,195 | B2 | 5/2005 | Su et al. |
| 6,902,737 | B2 | 6/2005 | Quemin et al. |
| 6,911,211 | B2 | 6/2005 | Eini et al. |
| 6,914,057 | B1 | 7/2005 | Ryan et al. |
| 6,946,120 | B2 | 9/2005 | Wai-Chiu So et al. |
| 6,946,139 | B2 | 9/2005 | Henning |

(56) References Cited

U.S. PATENT DOCUMENTS

| | | |
|---|---|---|
| 6,951,654 B2 | 10/2005 | Malcolm et al. |
| 6,955,816 B2 | 10/2005 | Klysz |
| 6,956,062 B2 | 10/2005 | Beilfuss et al. |
| 6,958,154 B2 | 10/2005 | Andolino Brandt et al. |
| 6,967,023 B1 | 11/2005 | Eini et al. |
| 6,968,982 B1 | 11/2005 | Burns |
| 6,969,521 B1 | 11/2005 | Gonzalez et al. |
| RE38,964 E | 1/2006 | Shillington |
| 6,986,883 B2 | 1/2006 | Pellico |
| 6,994,863 B2 | 2/2006 | Eini et al. |
| 7,002,486 B2 | 2/2006 | Lawrence |
| 7,014,844 B2 | 3/2006 | Mahalingam et al. |
| 7,021,499 B2 | 4/2006 | Hansen et al. |
| 7,029,659 B2 | 4/2006 | Abram |
| 7,060,253 B1 | 6/2006 | Mundschenk |
| 7,078,058 B2 | 7/2006 | Jones et al. |
| 7,083,799 B1 | 8/2006 | Giacomoni |
| 7,137,536 B2 | 11/2006 | Walters et al. |
| 7,195,135 B1 | 3/2007 | Garcia |
| 7,222,802 B2 | 5/2007 | Sweeton |
| 7,225,518 B2 | 6/2007 | Eidenschink et al. |
| 7,226,230 B2 | 6/2007 | Liberatore |
| 7,235,251 B2 | 6/2007 | Hamer et al. |
| 7,252,816 B1 | 8/2007 | Angel et al. |
| 7,270,828 B2 | 9/2007 | Masuda et al. |
| 7,455,195 B2 | 11/2008 | Meketa |
| 7,497,354 B2 | 3/2009 | Decottignies et al. |
| 7,575,739 B2 | 8/2009 | Tamarkin et al. |
| 7,645,803 B2 | 1/2010 | Tamarkin et al. |
| 7,654,415 B2 | 2/2010 | van der Heijden |
| 7,682,623 B2 | 3/2010 | Eini et al. |
| 7,700,076 B2 | 4/2010 | Tamarkin et al. |
| 7,704,518 B2 | 4/2010 | Tamarkin et al. |
| 7,758,888 B2 | 7/2010 | Lapidot et al. |
| 7,793,807 B2 | 9/2010 | Goujon et al. |
| 7,820,145 B2 | 10/2010 | Tamarkin et al. |
| 7,842,791 B2 | 11/2010 | Britten et al. |
| 7,960,416 B2 | 6/2011 | Sato et al. |
| 8,114,385 B2 | 2/2012 | Tamarkin et al. |
| 8,119,106 B2 | 2/2012 | Tamarkin et al. |
| 8,119,109 B2 | 2/2012 | Tamarkin et al. |
| 8,119,150 B2 | 2/2012 | Tamarkin et al. |
| 8,158,109 B2 | 4/2012 | Abram et al. |
| 8,192,749 B2 | 6/2012 | Ashley |
| 8,211,874 B2 | 7/2012 | Theobald et al. |
| 8,343,945 B2 | 1/2013 | Tamarkin et al. |
| 8,362,091 B2 | 1/2013 | Tamarkin et al. |
| 8,435,498 B2 | 5/2013 | Tamarkin et al. |
| 8,486,374 B2 | 7/2013 | Tamarkin et al. |
| 8,486,375 B2 | 7/2013 | Tamarkin et al. |
| 8,486,376 B2 | 7/2013 | Friedman et al. |
| 8,512,718 B2 | 8/2013 | Eini et al. |
| 8,518,376 B2 | 8/2013 | Tamarkin et al. |
| 8,518,378 B2 | 8/2013 | Tamarkin et al. |
| 8,592,380 B2 | 11/2013 | Trumbore et al. |
| 8,617,100 B2 | 12/2013 | Eini et al. |
| 8,618,081 B2 | 12/2013 | Tamarkin et al. |
| 8,623,330 B2 | 1/2014 | Gurge et al. |
| 8,636,982 B2 | 1/2014 | Tamarkin et al. |
| 8,652,443 B2 | 2/2014 | Varanasi et al. |
| 8,703,105 B2 | 4/2014 | Tamarkin et al. |
| 8,709,385 B2 | 4/2014 | Tamarkin et al. |
| 8,722,021 B2 | 5/2014 | Friedman et al. |
| 8,735,377 B1 | 5/2014 | Sipos |
| 8,741,265 B2 | 6/2014 | Tamarkin et al. |
| 8,778,365 B1 | 7/2014 | Hardas et al. |
| 8,784,780 B2 | 7/2014 | Gurge et al. |
| 8,795,635 B2 | 8/2014 | Tamarkin et al. |
| 8,795,693 B2 | 8/2014 | Tamarkin et al. |
| 8,840,869 B2 | 9/2014 | Friedman et al. |
| 8,846,039 B2 | 9/2014 | Chung et al. |
| 8,865,139 B1 | 10/2014 | Tamarkin et al. |
| 8,871,184 B2 | 10/2014 | Tamarkin et al. |
| 8,895,536 B2 | 11/2014 | Bannister et al. |
| 8,900,553 B2 | 12/2014 | Tamarkin et al. |
| 8,900,554 B2 | 12/2014 | Tamarkin et al. |
| 8,945,516 B2 | 2/2015 | Tamarkin et al. |
| 8,992,896 B2 | 3/2015 | Tamarkin et al. |
| 9,050,253 B2 | 6/2015 | Tamarkin et al. |
| 9,072,667 B2 | 7/2015 | Tamarkin et al. |
| 9,101,662 B2 | 8/2015 | Tamarkin et al. |
| 9,161,916 B2 | 10/2015 | Tamarkin et al. |
| 9,167,813 B2 | 10/2015 | Tamarkin et al. |
| 9,192,558 B2 | 11/2015 | Chen et al. |
| 9,211,259 B2 | 12/2015 | Friedman et al. |
| 9,265,725 B2 | 2/2016 | Tamarkin et al. |
| 9,265,740 B2 | 2/2016 | Johnston et al. |
| 9,271,930 B2 | 3/2016 | At |
| 9,320,705 B2 | 4/2016 | Tamarkin et al. |
| 9,439,857 B2 | 9/2016 | Tamarkin et al. |
| 9,474,720 B2 | 10/2016 | Yamamoto |
| 9,492,412 B2 | 11/2016 | Tamarkin et al. |
| 9,539,208 B2 | 1/2017 | Tamarkin et al. |
| 9,539,266 B2 | 1/2017 | Mansouri |
| 9,549,898 B2 | 1/2017 | Tamarkin et al. |
| 9,572,775 B2 | 2/2017 | Tamarkin et al. |
| 9,592,246 B2 | 3/2017 | Salman et al. |
| 9,622,947 B2 | 4/2017 | Tamarkin et al. |
| 9,636,405 B2 | 5/2017 | Tamarkin et al. |
| 9,662,298 B2 | 5/2017 | Tamarkin et al. |
| 9,668,972 B2 | 6/2017 | Tamarkin et al. |
| 9,675,700 B2 | 6/2017 | Tamarkin et al. |
| 9,682,021 B2 | 6/2017 | Tamarkin et al. |
| 9,713,643 B2 | 7/2017 | Friedman et al. |
| 9,795,564 B2 | 10/2017 | Tamarkin et al. |
| 9,849,142 B2 | 12/2017 | Tamarkin et al. |
| 9,884,017 B2 | 2/2018 | Tamarkin et al. |
| 9,931,328 B2 | 4/2018 | Kandavilli et al. |
| 10,029,013 B2 | 7/2018 | Tamarkin et al. |
| 10,086,080 B2 | 10/2018 | Tamarkin et al. |
| 10,137,200 B2 | 11/2018 | Tamarkin et al. |
| 2001/0006654 A1 | 7/2001 | Cannell et al. |
| 2001/0027218 A1 | 10/2001 | Stern et al. |
| 2001/0027981 A1 | 10/2001 | Yquel |
| 2001/0033838 A1 | 10/2001 | Farmer |
| 2001/0036450 A1 | 11/2001 | Verite et al. |
| 2001/0054574 A1 | 12/2001 | Navarro |
| 2002/0004063 A1 | 1/2002 | Zhang |
| 2002/0013481 A1 | 1/2002 | Schonrock et al. |
| 2002/0015721 A1 | 2/2002 | Simonnet et al. |
| 2002/0031478 A1 | 3/2002 | Keller et al. |
| 2002/0032171 A1 | 3/2002 | Chen et al. |
| 2002/0035046 A1 | 3/2002 | Lukenbach et al. |
| 2002/0035070 A1 | 3/2002 | Gardlik et al. |
| 2002/0035087 A1 | 3/2002 | Barclay |
| 2002/0035182 A1 | 3/2002 | L'Alloret et al. |
| 2002/0039591 A1 | 4/2002 | Dahle |
| 2002/0044659 A1 | 4/2002 | Ohta |
| 2002/0045659 A1 | 4/2002 | Michelet et al. |
| 2002/0048798 A1 | 4/2002 | Avery et al. |
| 2002/0058010 A1 | 5/2002 | Picard-Lesboueyries et al. |
| 2002/0072544 A1 | 6/2002 | Miller et al. |
| 2002/0090386 A1 | 7/2002 | Halswanter et al. |
| 2002/0098215 A1 | 7/2002 | Douin et al. |
| 2002/0111281 A1 | 8/2002 | Vishnupad |
| 2002/0117516 A1 | 8/2002 | Lasserre et al. |
| 2002/0134376 A1 | 9/2002 | Castro et al. |
| 2002/0136755 A1 | 9/2002 | Tyrrell et al. |
| 2002/0143188 A1 | 10/2002 | Garvey et al. |
| 2002/0153390 A1 | 10/2002 | Vlodek |
| 2002/0165170 A1 | 11/2002 | Wilson et al. |
| 2002/0182162 A1 | 12/2002 | Shahinpoor et al. |
| 2002/0182234 A1 | 12/2002 | Riedel et al. |
| 2002/0187181 A1 | 12/2002 | Godbey et al. |
| 2002/0198136 A1 | 12/2002 | Mak et al. |
| 2003/0006193 A1 | 1/2003 | Ikeda et al. |
| 2003/0013692 A1 | 1/2003 | Gullans et al. |
| 2003/0017181 A1 | 1/2003 | Rood et al. |
| 2003/0031693 A1 | 2/2003 | Breton et al. |
| 2003/0053961 A1 | 3/2003 | Eccard |
| 2003/0077297 A1 | 4/2003 | Chen et al. |
| 2003/0077301 A1 | 4/2003 | Maibach et al. |
| 2003/0078172 A1 | 4/2003 | Guiramand et al. |
| 2003/0082120 A1 | 5/2003 | Milstein |

(56) References Cited

U.S. PATENT DOCUMENTS

| | | |
|---|---|---|
| 2003/0108502 A1 | 6/2003 | Uchida et al. |
| 2003/0114520 A1 | 6/2003 | Pereira et al. |
| 2003/0118515 A1 | 6/2003 | Jew et al. |
| 2003/0118527 A1 | 6/2003 | Jager et al. |
| 2003/0129259 A1 | 7/2003 | Mahalingam et al. |
| 2003/0130247 A1 | 7/2003 | Gans et al. |
| 2003/0148949 A1 | 8/2003 | Podolsky |
| 2003/0175232 A1 | 9/2003 | Elliott et al. |
| 2003/0175315 A1 | 9/2003 | Yoo et al. |
| 2003/0180347 A1 | 9/2003 | Young et al. |
| 2003/0185839 A1 | 10/2003 | Podolsky |
| 2003/0185861 A1 | 10/2003 | Hori et al. |
| 2003/0194379 A1 | 10/2003 | Brugger et al. |
| 2003/0195128 A1 | 10/2003 | Deckman et al. |
| 2003/0206955 A1 | 11/2003 | Sonneville-Aubrun et al. |
| 2003/0215418 A1 | 11/2003 | Asmus et al. |
| 2003/0215472 A1 | 11/2003 | Bonda et al. |
| 2003/0235597 A1 | 12/2003 | Withiam et al. |
| 2004/0002550 A1 | 1/2004 | Mecurio |
| 2004/0018228 A1 | 1/2004 | Fischell et al. |
| 2004/0028752 A1 | 2/2004 | Kamm et al. |
| 2004/0038912 A1 | 2/2004 | Michelet et al. |
| 2004/0053797 A1 | 3/2004 | Chen et al. |
| 2004/0058878 A1 | 3/2004 | Walker |
| 2004/0063787 A1 | 4/2004 | Villanueva |
| 2004/0067970 A1 | 4/2004 | Foster et al. |
| 2004/0072638 A1 | 4/2004 | Enos et al. |
| 2004/0076651 A1 | 4/2004 | Brocks et al. |
| 2004/0078896 A1 | 4/2004 | Hellyer et al. |
| 2004/0079361 A1 | 4/2004 | Clayton et al. |
| 2004/0105825 A1 | 6/2004 | Henning |
| 2004/0106688 A1 | 6/2004 | Koike et al. |
| 2004/0120917 A1 | 6/2004 | Perrier et al. |
| 2004/0127554 A1 | 7/2004 | Ghisalberti |
| 2004/0138179 A1 | 7/2004 | Goldstein et al. |
| 2004/0151671 A1 | 8/2004 | Abram et al. |
| 2004/0151756 A1 | 8/2004 | Richards et al. |
| 2004/0161447 A1 | 8/2004 | Paul |
| 2004/0184992 A1 | 9/2004 | Abram |
| 2004/0185123 A1 | 9/2004 | Mazzio et al. |
| 2004/0191196 A1 | 9/2004 | Tamarkin |
| 2004/0192754 A1 | 9/2004 | Shapira et al. |
| 2004/0195276 A1 | 10/2004 | Fuchs |
| 2004/0197276 A1 | 10/2004 | Takase et al. |
| 2004/0197295 A1 | 10/2004 | Riedel et al. |
| 2004/0198706 A1 | 10/2004 | Carrara |
| 2004/0219176 A1 | 11/2004 | Dominguez |
| 2004/0220187 A1 | 11/2004 | Stephenson et al. |
| 2004/0229813 A1 | 11/2004 | DiPiano et al. |
| 2004/0234475 A1 | 11/2004 | Lannibois-Drean et al. |
| 2004/0241099 A1 | 12/2004 | Popp et al. |
| 2004/0247531 A1 | 12/2004 | Riedel et al. |
| 2004/0258627 A1 | 12/2004 | Riedel et al. |
| 2004/0258628 A1 | 12/2004 | Riedel et al. |
| 2004/0258643 A1 | 12/2004 | Yaqub et al. |
| 2005/0002976 A1 | 1/2005 | Wu |
| 2005/0013853 A1 | 1/2005 | Gil-Ad et al. |
| 2005/0042182 A1 | 2/2005 | Arkin et al. |
| 2005/0054991 A1 | 3/2005 | Tobyn et al. |
| 2005/0069566 A1 | 3/2005 | Tamarkin et al. |
| 2005/0075407 A1 | 4/2005 | Tamarkin et al. |
| 2005/0079139 A1 | 4/2005 | Jacques et al. |
| 2005/0079228 A1 | 4/2005 | Jaiswal et al. |
| 2005/0084551 A1 | 4/2005 | Jensen et al. |
| 2005/0085843 A1 | 4/2005 | Opolski et al. |
| 2005/0100517 A1 | 5/2005 | Sanzgiri et al. |
| 2005/0101936 A1 | 5/2005 | Gonzales et al. |
| 2005/0106197 A1 | 5/2005 | Blin et al. |
| 2005/0123494 A1 | 6/2005 | Swaile et al. |
| 2005/0123496 A1 | 6/2005 | Shah et al. |
| 2005/0148552 A1 | 7/2005 | Ryan et al. |
| 2005/0153943 A1 | 7/2005 | Ashley |
| 2005/0164993 A1 | 7/2005 | Ashley |
| 2005/0186142 A1 | 8/2005 | Tamarkin et al. |
| 2005/0186147 A1 | 8/2005 | Tamarkin et al. |
| 2005/0189377 A1 | 9/2005 | Lanzendorfer et al. |
| 2005/0196414 A1 | 9/2005 | Dake et al. |
| 2005/0205086 A1 | 9/2005 | Tamarkin et al. |
| 2005/0207837 A1 | 9/2005 | Kosh et al. |
| 2005/0222090 A1 | 10/2005 | Cheng et al. |
| 2005/0232869 A1 | 10/2005 | Tamarkin et al. |
| 2005/0244354 A1 | 11/2005 | Speron |
| 2005/0245902 A1 | 11/2005 | Cornish et al. |
| 2005/0252995 A1 | 11/2005 | Westphal et al. |
| 2005/0255048 A1 | 11/2005 | Hirsh et al. |
| 2005/0258189 A1 | 11/2005 | Peterson et al. |
| 2005/0266035 A1 | 12/2005 | Healy et al. |
| 2005/0268416 A1 | 12/2005 | Sommers |
| 2005/0271596 A1 | 12/2005 | Friedman et al. |
| 2005/0276836 A1 | 12/2005 | Wilson et al. |
| 2005/0281749 A1 | 12/2005 | Willcox et al. |
| 2005/0281755 A1 | 12/2005 | Zarif et al. |
| 2005/0281766 A1 | 12/2005 | Martin et al. |
| 2005/0285912 A1 | 12/2005 | Delametter et al. |
| 2005/0287081 A1 | 12/2005 | Aust et al. |
| 2006/0008432 A1 | 1/2006 | Scarampi et al. |
| 2006/0018937 A1 | 1/2006 | Friedman et al. |
| 2006/0018938 A1 | 1/2006 | Neubourg |
| 2006/0029565 A1 | 2/2006 | Xu et al. |
| 2006/0051301 A1 | 3/2006 | Galopin et al. |
| 2006/0054634 A1 | 3/2006 | Meketa |
| 2006/0057168 A1 | 3/2006 | Larm et al. |
| 2006/0099151 A1 | 5/2006 | Neubourg |
| 2006/0108377 A1 | 5/2006 | Glynn et al. |
| 2006/0110415 A1 | 5/2006 | Gupta |
| 2006/0110418 A1 | 5/2006 | Johnson |
| 2006/0114745 A1 | 6/2006 | Ollmann et al. |
| 2006/0121073 A1 | 6/2006 | Goyal et al. |
| 2006/0140984 A1 | 6/2006 | Tamarkin et al. |
| 2006/0140990 A1 | 6/2006 | Bortz et al. |
| 2006/0160713 A1 | 7/2006 | Sekine et al. |
| 2006/0165616 A1 | 7/2006 | Brock et al. |
| 2006/0177392 A1 | 8/2006 | Walden |
| 2006/0193789 A1 | 8/2006 | Tamarkin et al. |
| 2006/0193813 A1 | 8/2006 | Simonnet |
| 2006/0204446 A1 | 9/2006 | Lulla et al. |
| 2006/0222675 A1 | 10/2006 | Sabnis et al. |
| 2006/0233721 A1 | 10/2006 | Tamarkin et al. |
| 2006/0239937 A2 | 10/2006 | Neubourg |
| 2006/0251684 A1 | 11/2006 | Annis et al. |
| 2006/0254597 A1 | 11/2006 | Thompson |
| 2006/0263323 A1 | 11/2006 | Hoang et al. |
| 2006/0269485 A1 | 11/2006 | Friedman et al. |
| 2006/0272199 A1 | 12/2006 | Licciardello et al. |
| 2006/0285912 A1 | 12/2006 | Eini et al. |
| 2006/0292080 A1 | 12/2006 | Abram et al. |
| 2007/0009607 A1 | 1/2007 | Jones |
| 2007/0010580 A1 | 1/2007 | De Paoli Ambrosi |
| 2007/0015739 A1 | 1/2007 | Walker et al. |
| 2007/0017696 A1 | 1/2007 | Lin et al. |
| 2007/0020213 A1 | 1/2007 | Tamarkin et al. |
| 2007/0020304 A1 | 1/2007 | Tamarkin et al. |
| 2007/0027055 A1 | 2/2007 | Koivisto et al. |
| 2007/0036831 A1 | 2/2007 | Baker |
| 2007/0053943 A1 | 3/2007 | Wang et al. |
| 2007/0059253 A1 | 3/2007 | Popp et al. |
| 2007/0069046 A1 | 3/2007 | Eini et al. |
| 2007/0071688 A1 | 3/2007 | Illel et al. |
| 2007/0098647 A1 | 5/2007 | Neubourg |
| 2007/0111956 A1 | 5/2007 | Matsushima et al. |
| 2007/0134174 A1 | 6/2007 | Irwin et al. |
| 2007/0140998 A1 | 6/2007 | Kato et al. |
| 2007/0140999 A1 | 6/2007 | Puglia et al. |
| 2007/0141086 A1 | 6/2007 | Ohara et al. |
| 2007/0142263 A1 | 6/2007 | Stahl et al. |
| 2007/0148112 A1 | 6/2007 | Dingley et al. |
| 2007/0148194 A1 | 6/2007 | Amiji et al. |
| 2007/0154402 A1 | 7/2007 | Trumbore et al. |
| 2007/0160548 A1 | 7/2007 | Riccardi et al. |
| 2007/0166274 A1 | 7/2007 | Mazur et al. |
| 2007/0224143 A1 | 9/2007 | Konis |
| 2007/0237724 A1 | 10/2007 | Abram et al. |
| 2007/0264317 A1 | 11/2007 | Yosha et al. |
| 2007/0271235 A1 | 11/2007 | Frank et al. |

(56) References Cited

U.S. PATENT DOCUMENTS

| | | |
|---|---|---|
| 2007/0281999 A1 | 12/2007 | Fox et al. |
| 2007/0292355 A1 | 12/2007 | Tamarkin et al. |
| 2007/0292359 A1 | 12/2007 | Friedman et al. |
| 2007/0292461 A1 | 12/2007 | Tamarkin et al. |
| 2008/0008397 A1 | 1/2008 | Kisilev |
| 2008/0015263 A1 | 1/2008 | Bolotin et al. |
| 2008/0015271 A1 | 1/2008 | Abram et al. |
| 2008/0031907 A1 | 2/2008 | Tamarkin et al. |
| 2008/0031908 A1 | 2/2008 | Aubrun-Sonneville et al. |
| 2008/0035155 A1 | 2/2008 | Dahl |
| 2008/0044444 A1 | 2/2008 | Tamarkin et al. |
| 2008/0050317 A1 | 2/2008 | Tamarkin et al. |
| 2008/0058055 A1 | 3/2008 | LeMay et al. |
| 2008/0063682 A1 | 3/2008 | Cashman et al. |
| 2008/0069779 A1 | 3/2008 | Tamarkin et al. |
| 2008/0131378 A1 | 6/2008 | Keller et al. |
| 2008/0138293 A1 | 6/2008 | Tamarkin et al. |
| 2008/0138296 A1 | 6/2008 | Tamarkin et al. |
| 2008/0152596 A1 | 6/2008 | Friedman et al. |
| 2008/0153789 A1 | 6/2008 | Dmowski et al. |
| 2008/0166303 A1 | 7/2008 | Tamarkin et al. |
| 2008/0167376 A1 | 7/2008 | Bar-Or et al. |
| 2008/0181854 A1 | 7/2008 | Eini et al. |
| 2008/0188445 A1 | 8/2008 | Muldoon et al. |
| 2008/0188446 A1 | 8/2008 | Muldoon et al. |
| 2008/0193762 A1 | 8/2008 | Dubertret et al. |
| 2008/0206155 A1 | 8/2008 | Tamarkin et al. |
| 2008/0206161 A1 | 8/2008 | Tamarkin et al. |
| 2008/0241079 A1 | 10/2008 | Neubourg |
| 2008/0253973 A1 | 10/2008 | Tamarkin et al. |
| 2008/0255498 A1 | 10/2008 | Houle |
| 2008/0260655 A1 | 10/2008 | Tamarkin et al. |
| 2008/0292560 A1 | 11/2008 | Tamarkin et al. |
| 2008/0311167 A1 | 12/2008 | Oronsky et al. |
| 2008/0317679 A1 | 12/2008 | Tamarkin et al. |
| 2009/0017147 A1 | 1/2009 | Lintner et al. |
| 2009/0053290 A1 | 2/2009 | Sand et al. |
| 2009/0061001 A1 | 3/2009 | Hougaz |
| 2009/0093514 A1 | 4/2009 | Statham et al. |
| 2009/0130029 A1 | 5/2009 | Tamarkin et al. |
| 2009/0131488 A1 | 5/2009 | Harel et al. |
| 2009/0175799 A1 | 7/2009 | Tamarkin et al. |
| 2009/0214628 A1 | 8/2009 | De Rijk |
| 2009/0291917 A1 | 11/2009 | Akama et al. |
| 2010/0111879 A1 | 5/2010 | Tamarkin et al. |
| 2010/0221194 A1 | 9/2010 | Loupenok |
| 2010/0247449 A1 | 9/2010 | Graupe et al. |
| 2010/0286417 A1 | 11/2010 | Mendes et al. |
| 2011/0002969 A1 | 1/2011 | Serraima et al. |
| 2011/0097279 A1 | 4/2011 | Tamarkin et al. |
| 2011/0207765 A1 | 8/2011 | Van Den Bussche et al. |
| 2011/0262542 A1 | 10/2011 | Ashley |
| 2012/0064136 A1 | 3/2012 | Baker, Jr. et al. |
| 2012/0082632 A1 | 4/2012 | Phillips et al. |
| 2012/0087872 A1 | 4/2012 | Tamarkin et al. |
| 2012/0128598 A1 | 5/2012 | Trumbore et al. |
| 2012/0141384 A1 | 6/2012 | Tamarkin |
| 2012/0148503 A1 | 6/2012 | Tamarkin et al. |
| 2012/0156144 A1 | 6/2012 | Tamarkin et al. |
| 2012/0164087 A1 | 6/2012 | Carter |
| 2012/0181201 A1 | 7/2012 | Heggie |
| 2012/0237453 A1 | 9/2012 | Tamarkin et al. |
| 2013/0053353 A1 | 2/2013 | Tamarkin et al. |
| 2013/0115173 A1 | 5/2013 | Trumbore et al. |
| 2013/0161351 A1 | 6/2013 | Eini et al. |
| 2013/0164225 A1 | 6/2013 | Tamarkin et al. |
| 2013/0189195 A1 | 7/2013 | Tamarkin et al. |
| 2013/0189196 A1 | 7/2013 | Tamarkin et al. |
| 2013/0251644 A1 | 9/2013 | Majhi et al. |
| 2013/0261565 A1 | 10/2013 | Wong et al. |
| 2013/0295022 A1 | 11/2013 | Friedman et al. |
| 2013/0296387 A1 | 11/2013 | Saad |
| 2014/0066524 A1 | 3/2014 | Tamarkin et al. |
| 2014/0086848 A1 | 3/2014 | Tamarkin et al. |
| 2014/0121188 A1 | 5/2014 | Tamarkin et al. |
| 2014/0140937 A1 | 5/2014 | Gurge et al. |
| 2014/0182585 A1 | 7/2014 | Tamarkin et al. |
| 2014/0186269 A1 | 7/2014 | Tamarkin et al. |
| 2014/0221320 A1 | 8/2014 | Joks et al. |
| 2014/0228355 A1 | 8/2014 | Kortagere et al. |
| 2014/0242016 A1 | 8/2014 | Binks et al. |
| 2014/0248219 A1 | 9/2014 | Tamarkin et al. |
| 2015/0025060 A1 | 1/2015 | Tamarkin et al. |
| 2015/0098907 A1 | 4/2015 | Tamarkin et al. |
| 2015/0141381 A1 | 5/2015 | Levy et al. |
| 2015/0157586 A1 | 6/2015 | Tamarkin et al. |
| 2015/0164922 A1 | 6/2015 | Tamarkin et al. |
| 2015/0174144 A1 | 6/2015 | Bowser et al. |
| 2015/0196570 A1 | 7/2015 | Tamarkin et al. |
| 2015/0209296 A1 | 7/2015 | Yamamoto |
| 2015/0374625 A1 | 12/2015 | Tamarkin et al. |
| 2016/0101184 A1 | 4/2016 | Tamarkin et al. |
| 2016/0128944 A1 | 5/2016 | Chawrai et al. |
| 2016/0158261 A1 | 6/2016 | Friedman et al. |
| 2016/0213757 A1 | 7/2016 | Edelson et al. |
| 2016/0279152 A1 | 9/2016 | Chen et al. |
| 2016/0287615 A1 | 10/2016 | Chan et al. |
| 2016/0354473 A1 | 12/2016 | Tamarkin et al. |
| 2016/0361252 A1 | 12/2016 | Franke |
| 2016/0361320 A1 | 12/2016 | Zhao et al. |
| 2017/0014517 A1 | 1/2017 | Tamarkin |
| 2017/0049712 A1 | 2/2017 | Bhalani et al. |
| 2017/0119665 A1 | 5/2017 | Tamarkin et al. |
| 2017/0157175 A1 | 6/2017 | Tamarkin et al. |
| 2017/0172857 A1 | 6/2017 | Tamarkin et al. |
| 2017/0181970 A1 | 6/2017 | Tamarkin et al. |
| 2017/0216334 A1 | 8/2017 | Tamarkin et al. |
| 2017/0231909 A1 | 8/2017 | Tamarkin et al. |
| 2017/0274084 A1 | 9/2017 | Friedman et al. |
| 2017/0340743 A1 | 11/2017 | Tamarkin et al. |
| 2017/0348418 A1 | 12/2017 | Tamarkin et al. |
| 2017/0354597 A1 | 12/2017 | Tamarkin et al. |
| 2018/0000734 A1 | 1/2018 | Tamarkin et al. |
| 2018/0064638 A1 | 3/2018 | Tamarkin et al. |
| 2018/0147218 A1 | 5/2018 | Tamarkin et al. |
| 2018/0153804 A1 | 6/2018 | Tamarkin et al. |
| 2018/0214558 A1 | 8/2018 | Tamarkin et al. |
| 2018/0235984 A1 | 8/2018 | Eini et al. |
| 2019/0000980 A1 | 1/2019 | Tamarkin et al. |
| 2019/0022000 A1 | 1/2019 | Tamarkin et al. |
| 2019/0022001 A1 | 1/2019 | Tamarkin et al. |
| 2019/0029958 A1 | 1/2019 | Tamarkin et al. |
| 2019/0054106 A1 | 2/2019 | Tamarkin et al. |

FOREIGN PATENT DOCUMENTS

| | | |
|---|---|---|
| CA | 2114537 A1 | 2/1993 |
| CA | 2154438 A1 | 1/1996 |
| CA | 2422244 A1 | 9/2003 |
| CA | 2502986 A1 | 5/2004 |
| CA | 2534372 A1 | 10/2005 |
| CH | 639913 A5 | 12/1983 |
| DE | 1 882 100 U | 11/1963 |
| DE | 1926796 A1 | 3/1970 |
| DE | 2 608 226 A1 | 9/1977 |
| DE | 4140474 A1 | 6/1993 |
| DE | 10009233 A1 | 8/2000 |
| DE | 10138495 A1 | 2/2003 |
| DE | 102004016710 A1 | 10/2005 |
| EP | 0 052 404 A2 | 5/1982 |
| EP | 0 156 507 A1 | 10/1985 |
| EP | 0 186 453 A2 | 7/1986 |
| EP | 0 213 827 A2 | 3/1987 |
| EP | 0 214 865 A2 | 3/1987 |
| EP | 0 270 316 A2 | 6/1988 |
| EP | 0 297 436 A2 | 1/1989 |
| EP | 0 336 812 A2 | 10/1989 |
| EP | 0 414 920 A1 | 3/1991 |
| EP | 0 211 550 B1 | 4/1991 |
| EP | 0 216 856 B1 | 7/1991 |
| EP | 0 454 102 A2 | 10/1991 |
| EP | 0 326 196 B2 | 3/1992 |
| EP | 0 484 530 A1 | 5/1992 |
| EP | 0 485 299 A1 | 5/1992 |

(56) References Cited

FOREIGN PATENT DOCUMENTS

| | | |
|---|---|---|
| EP | 0 488 089 A1 | 6/1992 |
| EP | 0 528 190 A1 | 2/1993 |
| EP | 0 552 612 A2 | 7/1993 |
| EP | 0 569 773 A2 | 11/1993 |
| EP | 0 404 376 B1 | 3/1994 |
| EP | 0 598 412 A2 | 5/1994 |
| EP | 0 391 124 B1 | 6/1995 |
| EP | 0 662 431 A2 | 7/1995 |
| EP | 0 535 327 B1 | 10/1996 |
| EP | 0 738 516 A1 | 10/1996 |
| EP | 0 757 959 A1 | 2/1997 |
| EP | 0 824 911 A2 | 2/1998 |
| EP | 0 829 259 A1 | 3/1998 |
| EP | 0 676 198 B1 | 10/1998 |
| EP | 0 979 654 A1 | 2/2000 |
| EP | 0 993 827 A1 | 4/2000 |
| EP | 1 025 836 A1 | 8/2000 |
| EP | 1 055 425 A2 | 11/2000 |
| EP | 0 506 197 B2 | 7/2001 |
| EP | 1 215 258 A2 | 6/2002 |
| EP | 1 287 813 A1 | 3/2003 |
| EP | 1 308 169 A1 | 5/2003 |
| EP | 1 375 386 A1 | 1/2004 |
| EP | 0 504 301 B1 | 3/2004 |
| EP | 1 428 521 A2 | 6/2004 |
| EP | 1 438 946 A1 | 7/2004 |
| EP | 1 189 579 B1 | 9/2004 |
| EP | 1 475 381 A1 | 11/2004 |
| EP | 1 500 385 A1 | 1/2005 |
| EP | 1 537 916 A1 | 6/2005 |
| EP | 1 600 185 A1 | 11/2005 |
| EP | 0 928 608 B1 | 3/2006 |
| EP | 1 653 932 A1 | 5/2006 |
| EP | 1 734 927 A1 | 12/2006 |
| EP | 1 758 547 A1 | 3/2007 |
| EP | 1 483 001 B1 | 11/2007 |
| EP | 1 584 324 B1 | 11/2007 |
| EP | 1 889 609 A2 | 2/2008 |
| EP | 1 902 706 A1 | 3/2008 |
| EP | 2 129 383 A1 | 12/2009 |
| EP | 2 422 768 A2 | 2/2012 |
| EP | 2 494 959 A1 | 9/2012 |
| FR | 2 456 522 A1 | 12/1980 |
| FR | 2 591 331 A1 | 6/1987 |
| FR | 2 640 942 A2 | 6/1990 |
| FR | 2 736 824 A1 | 1/1997 |
| FR | 2 774 595 A1 | 8/1999 |
| FR | 2 789 371 A1 | 8/2000 |
| FR | 2 793 479 A1 | 11/2000 |
| FR | 2 814 959 A1 | 4/2002 |
| FR | 2 833 246 A1 | 6/2003 |
| FR | 2 840 903 A1 | 12/2003 |
| FR | 2 843 373 A1 | 2/2004 |
| FR | 2 845 672 A1 | 4/2004 |
| FR | 2 848 998 A1 | 6/2004 |
| FR | 2 860 976 | 4/2005 |
| FR | 2 915 891 A1 | 11/2008 |
| GB | 808 104 A | 1/1959 |
| GB | 808 105 A | 1/1959 |
| GB | 922 930 A | 4/1963 |
| GB | 933 486 A | 8/1963 |
| GB | 998 490 A | 7/1965 |
| GB | 1 026 831 A | 4/1966 |
| GB | 1 033 299 A | 6/1966 |
| GB | 1 081 949 A | 9/1967 |
| GB | 1 121 358 A | 7/1968 |
| GB | 1 162 684 A | 8/1969 |
| GB | 1 170 152 A | 11/1969 |
| GB | 1 201 918 A | 8/1970 |
| GB | 1 347 950 A | 2/1974 |
| GB | 1 351 761 A | 5/1974 |
| GB | 1 351 762 A | 5/1974 |
| GB | 1 353 381 A | 5/1974 |
| GB | 1 376 649 A | 12/1974 |
| GB | 1 397 285 A | 6/1975 |
| GB | 1 408 036 A | 10/1975 |
| GB | 1 457 671 A | 12/1976 |
| GB | 1 489 672 A | 10/1977 |
| GB | 2 004 746 A | 4/1979 |
| GB | 1 561 423 A | 2/1980 |
| GB | 2 114 580 A | 8/1983 |
| GB | 2 166 651 A | 5/1986 |
| GB | 2 153 686 B | 7/1987 |
| GB | 2 172 298 B | 11/1988 |
| GB | 2 206 099 A | 12/1988 |
| GB | 2 337 461 A | 11/1999 |
| GB | 2 367 809 A | 4/2002 |
| GB | 2 406 330 A | 3/2005 |
| GB | 2 406 791 B | 2/2008 |
| GB | 2 474 930 A | 5/2011 |
| IL | 49491 | 9/1979 |
| IL | 152 486 A | 5/2003 |
| JP | 55-069682 A | 5/1980 |
| JP | 56-039815 A | 4/1981 |
| JP | 57-044429 A | 3/1982 |
| JP | 60-001113 A | 1/1985 |
| JP | 61-275395 A | 12/1986 |
| JP | 62-241701 A | 10/1987 |
| JP | 63-119420 A | 5/1988 |
| JP | 01-100111 A | 4/1989 |
| JP | 01-156906 A | 6/1989 |
| JP | 02-184614 A | 7/1990 |
| JP | 02-255890 A | 10/1990 |
| JP | 03-050289 A | 3/1991 |
| JP | 04-51958 A | 2/1992 |
| JP | 04-282311 A | 10/1992 |
| JP | 04-312521 A | 11/1992 |
| JP | 05-070340 A | 3/1993 |
| JP | 05-213734 A | 8/1993 |
| JP | 06-100414 A | 4/1994 |
| JP | 06-263630 A | 9/1994 |
| JP | 06-329532 A | 11/1994 |
| JP | 07-215835 A | 8/1995 |
| JP | 08-040899 A | 2/1996 |
| JP | 08-501529 A | 2/1996 |
| JP | 08-119831 A | 5/1996 |
| JP | 08-165218 A | 6/1996 |
| JP | 08-277209 A | 10/1996 |
| JP | 09-84855 A | 3/1997 |
| JP | 09-099553 A | 4/1997 |
| JP | 09-110636 A | 4/1997 |
| JP | 10-114619 A | 5/1998 |
| JP | 10-332456 A | 12/1998 |
| JP | 11-501045 A | 1/1999 |
| JP | 11-250543 A | 9/1999 |
| JP | 2000-017174 A | 1/2000 |
| JP | 2000-080017 A | 3/2000 |
| JP | 2000-128734 A | 5/2000 |
| JP | 2000-191429 A | 7/2000 |
| JP | 2000-239140 A | 9/2000 |
| JP | 2000-351726 A | 12/2000 |
| JP | 2000-354623 A | 12/2000 |
| JP | 2001-002526 A | 1/2001 |
| JP | 2001-019606 A | 1/2001 |
| JP | 2001-072963 A | 3/2001 |
| JP | 2002-012513 A | 1/2002 |
| JP | 2002-047136 A | 2/2002 |
| JP | 2002-524490 A | 8/2002 |
| JP | 2002-302419 A | 10/2002 |
| JP | 2003-012511 A | 1/2003 |
| JP | 2003-055146 A | 2/2003 |
| JP | 2004-047136 A | 2/2004 |
| JP | 2004-250435 A | 9/2004 |
| JP | 2004-348277 A | 12/2004 |
| JP | 2005-314323 A | 11/2005 |
| JP | 2005-350378 A | 12/2005 |
| JP | 2006-008574 A | 1/2006 |
| JP | 2006-036317 A | 2/2006 |
| JP | 2006-103799 A | 4/2006 |
| JP | 2006-525145 A | 11/2006 |
| JP | 2007-131539 A2 | 5/2007 |
| JP | 2007-155667 A | 6/2007 |
| JP | 2007-326996 A | 12/2007 |
| KR | 0143232 A | 7/1998 |

(56) References Cited

FOREIGN PATENT DOCUMENTS

| | | |
|---|---|---|
| KR | 2001-003063 A | 1/2001 |
| NZ | 520014 A | 5/2005 |
| NZ | 540166 A | 6/2007 |
| RU | 2277501 C2 | 6/2006 |
| UA | 66796 C2 | 7/2001 |
| WO | WO 82/001821 A1 | 6/1982 |
| WO | WO 86/05389 A1 | 9/1986 |
| WO | WO 88/01502 A1 | 3/1988 |
| WO | WO 88/01863 A1 | 3/1988 |
| WO | WO 88/08316 A1 | 11/1988 |
| WO | WO 89/06537 A1 | 7/1989 |
| WO | WO 90/05774 A1 | 5/1990 |
| WO | WO 91/11991 A1 | 8/1991 |
| WO | WO 92/00077 A1 | 1/1992 |
| WO | WO 92/005142 A1 | 4/1992 |
| WO | WO 92/05763 A1 | 4/1992 |
| WO | WO 92/11839 A1 | 7/1992 |
| WO | WO 92/13602 A1 | 8/1992 |
| WO | WO 93/025189 A1 | 12/1993 |
| WO | WO 94/006440 A1 | 3/1994 |
| WO | WO 96/03115 A1 | 2/1996 |
| WO | WO 96/19921 A1 | 7/1996 |
| WO | WO 96/24325 A1 | 8/1996 |
| WO | WO 96/26711 A1 | 9/1996 |
| WO | WO 96/27376 A1 | 9/1996 |
| WO | WO 96/39119 A1 | 12/1996 |
| WO | WO 97/03638 A1 | 2/1997 |
| WO | WO 97/39745 A1 | 10/1997 |
| WO | WO 98/17282 A1 | 4/1998 |
| WO | WO 98/18472 A1 | 5/1998 |
| WO | WO 98/19654 A1 | 5/1998 |
| WO | WO 98/21955 A1 | 5/1998 |
| WO | WO 98/23291 A1 | 6/1998 |
| WO | WO 98/31339 A1 | 7/1998 |
| WO | WO 98/36733 A2 | 8/1998 |
| WO | WO 98/52536 A1 | 11/1998 |
| WO | WO 99/08649 A2 | 2/1999 |
| WO | WO 99/20250 A1 | 4/1999 |
| WO | WO 99/37282 A2 | 7/1999 |
| WO | WO 99/53923 A1 | 10/1999 |
| WO | WO 2000/09082 A1 | 2/2000 |
| WO | WO 2000/15193 A1 | 3/2000 |
| WO | WO 2000/23051 A1 | 4/2000 |
| WO | WO 2000/33825 A2 | 6/2000 |
| WO | WO 2000/38731 A1 | 7/2000 |
| WO | WO 2000/61076 A1 | 10/2000 |
| WO | WO 2000/62776 A1 | 10/2000 |
| WO | WO 2000/72805 A1 | 12/2000 |
| WO | WO 2000/76461 A2 | 12/2000 |
| WO | WO 2001/01949 A1 | 1/2001 |
| WO | WO 2001/05366 A1 | 1/2001 |
| WO | WO 2001/08681 A1 | 2/2001 |
| WO | WO 2001/10961 A1 | 2/2001 |
| WO | WO 2001/53198 A1 | 7/2001 |
| WO | WO 2001/54212 A1 | 7/2001 |
| WO | WO 2001/54679 A2 | 8/2001 |
| WO | WO 2001/62209 A2 | 8/2001 |
| WO | WO 2001/70242 A2 | 9/2001 |
| WO | WO 2001/76579 A1 | 10/2001 |
| WO | WO 2001/82880 A3 | 11/2001 |
| WO | WO 2001/82890 A1 | 11/2001 |
| WO | WO 2001/85102 A2 | 11/2001 |
| WO | WO 2001/85128 A2 | 11/2001 |
| WO | WO 2001/95728 A1 | 12/2001 |
| WO | WO 2002/00820 A1 | 1/2002 |
| WO | WO 2002/07685 A2 | 1/2002 |
| WO | WO 2002/15860 A1 | 2/2002 |
| WO | WO 2002/15873 A2 | 2/2002 |
| WO | WO 2002/24161 A1 | 3/2002 |
| WO | WO 2002/28435 A1 | 4/2002 |
| WO | WO 2002/41847 A1 | 5/2002 |
| WO | WO 2002/43490 A1 | 6/2002 |
| WO | WO 2002/062324 A2 | 8/2002 |
| WO | WO 2002/078667 A1 | 10/2002 |
| WO | WO 2002/087519 A2 | 11/2002 |
| WO | WO 2003/000223 A1 | 1/2003 |
| WO | WO 2003/002082 A1 | 1/2003 |
| WO | WO 2003/005985 A1 | 1/2003 |
| WO | WO 2003/013984 A1 | 2/2003 |
| WO | WO 2003/015699 A2 | 2/2003 |
| WO | WO 2003/051294 A2 | 6/2003 |
| WO | WO 2003/053292 A1 | 7/2003 |
| WO | WO 2003/055445 A2 | 7/2003 |
| WO | WO 2003/055454 A1 | 7/2003 |
| WO | WO 2003/070301 A1 | 8/2003 |
| WO | WO 2003/071995 A1 | 9/2003 |
| WO | WO 2003/075851 A2 | 9/2003 |
| WO | WO 2003/092641 A1 | 11/2003 |
| WO | WO 2003/094873 A1 | 11/2003 |
| WO | WO 2003/097002 A1 | 11/2003 |
| WO | WO 2004/017962 A2 | 3/2004 |
| WO | WO 2004/037197 A2 | 5/2004 |
| WO | WO 2004/037225 A2 | 5/2004 |
| WO | WO 2004/003284 A1 | 8/2004 |
| WO | WO 2004/064769 A2 | 8/2004 |
| WO | WO 2004/064833 A1 | 8/2004 |
| WO | WO 2004/071479 A1 | 8/2004 |
| WO | WO 2004/078158 A2 | 9/2004 |
| WO | WO 2004/078896 A1 | 9/2004 |
| WO | WO 2004/093895 A1 | 11/2004 |
| WO | WO 2004/112780 A1 | 12/2004 |
| WO | WO 2005/009416 A1 | 2/2005 |
| WO | WO 2005/011567 A2 | 2/2005 |
| WO | WO 2005/018530 A2 | 3/2005 |
| WO | WO 2005/032522 A2 | 4/2005 |
| WO | WO 2005/044219 A1 | 5/2005 |
| WO | WO 2005/063224 A1 | 7/2005 |
| WO | WO 2005/065652 A1 | 7/2005 |
| WO | WO 2005/076697 A2 | 8/2005 |
| WO | WO 2005/097068 A1 | 10/2005 |
| WO | WO 2005/102282 A1 | 11/2005 |
| WO | WO 2005/102539 A1 | 11/2005 |
| WO | WO 2005/117813 A1 | 12/2005 |
| WO | WO 2006/003481 A2 | 1/2006 |
| WO | WO 2006/010589 A2 | 2/2006 |
| WO | WO 2006/011046 A1 | 2/2006 |
| WO | WO 2006/020682 A1 | 2/2006 |
| WO | WO 2006/028339 A1 | 3/2006 |
| WO | WO 2006/031271 A2 | 3/2006 |
| WO | WO 2006/045170 A2 | 5/2006 |
| WO | WO 2006/079632 A1 | 8/2006 |
| WO | WO 2006/081327 A2 | 8/2006 |
| WO | WO 2006/091229 A2 | 8/2006 |
| WO | WO 2006/100485 A1 | 9/2006 |
| WO | WO 2006/120682 A2 | 11/2006 |
| WO | WO 2006/121610 A2 | 11/2006 |
| WO | WO 2006/122158 A2 | 11/2006 |
| WO | WO 2006/129161 A2 | 12/2006 |
| WO | WO 2006/131784 A1 | 12/2006 |
| WO | WO 2007/007208 A2 | 1/2007 |
| WO | WO 2007/010494 A1 | 1/2007 |
| WO | WO 2007/012977 A2 | 2/2007 |
| WO | WO 2007/023396 A2 | 3/2007 |
| WO | WO 2007/031621 A2 | 3/2007 |
| WO | WO 2007/039825 A2 | 4/2007 |
| WO | WO 2007/050543 A2 | 5/2007 |
| WO | WO 2007/054818 A2 | 5/2007 |
| WO | WO 2007/072216 A2 | 6/2007 |
| WO | WO 2007/082698 A1 | 7/2007 |
| WO | WO 2007/085902 A2 | 8/2007 |
| WO | WO 2007/099396 A2 | 9/2007 |
| WO | WO 2007/111962 A2 | 10/2007 |
| WO | WO 2008/008397 A2 | 1/2008 |
| WO | WO 2008/010963 A2 | 1/2008 |
| WO | WO 2008/038147 A2 | 4/2008 |
| WO | WO 2008/041045 A1 | 4/2008 |
| WO | WO 2008/075207 A2 | 6/2008 |
| WO | WO 2008/087148 A2 | 7/2008 |
| WO | WO 2008/104734 A1 | 9/2008 |
| WO | WO 2008/110872 A2 | 9/2008 |
| WO | WO 2008/152444 A2 | 12/2008 |
| WO | WO 2009/007785 A2 | 1/2009 |
| WO | WO 2009/069006 A2 | 6/2009 |
| WO | WO 2009/072007 A2 | 6/2009 |

(56) References Cited

FOREIGN PATENT DOCUMENTS

| | | |
|---|---|---|
| WO | WO 2009/087578 A2 | 7/2009 |
| WO | WO 2009/090495 A2 | 7/2009 |
| WO | WO 2009/090558 A2 | 7/2009 |
| WO | WO 2009/098595 A2 | 8/2009 |
| WO | WO 2011/006026 A1 | 1/2011 |
| WO | WO 2011/013008 A2 | 2/2011 |
| WO | WO 2011/013009 A2 | 2/2011 |
| WO | WO 2011/026094 A2 | 3/2011 |
| WO | WO 2011/039637 A2 | 4/2011 |
| WO | WO 2011/039638 A2 | 4/2011 |
| WO | WO 2011/064631 A1 | 6/2011 |
| WO | WO 2011/106026 A1 | 9/2011 |
| WO | WO 2011/138678 A2 | 11/2011 |
| WO | WO 2013/136192 A2 | 9/2013 |
| WO | WO 2014/134394 A1 | 9/2014 |
| WO | WO 2014/134427 A1 | 9/2014 |
| WO | WO 2014/151347 A1 | 9/2014 |
| WO | WO 2014/201541 A1 | 12/2014 |
| WO | WO 2015/075640 A1 | 5/2015 |
| WO | WO 2015/114320 A1 | 8/2015 |
| WO | WO 2015/153864 A2 | 10/2015 |
| WO | WO 2017/029647 A1 | 2/2017 |
| WO | WO 2017/030555 A1 | 2/2017 |

OTHER PUBLICATIONS

"Suppositories?" CareCure Community, SCI Forum [online]. http://sci.rutgers.edu/forum/showthread.php?4176-Suppositories. Published: Apr. 16, 2002, 3 pages.
1058. Benzalkonium Chloride; 2350. Citric Acid; 6143. Methyl Salicylate. The Merck Index: An Encyclopedia of Chemicals, Drugs, and Biologicals. 13th Edition, 2001, pp. 181, 405-406, 1090-1091, 1556.
242. Allantoin, The Merck Index: An Encyclopedia of Chemicals, Drugs, and Biologicals. 10th edition, Merck & Co., Inc., 1983, p. 39.
Abdullah, G.Z. et al. (Jan. 2013 ) "Carbopol 934, 940 and Ultrez 10 as viscosity modifiers of palm olein esters based nano-scaled emulsion containing ibuprofen" Pak J Pharm Sci, 26(1):75-83.
Abrams et al., "Ciclopirox gel treatment of scalp seborrheic dermatitis," in: Shuster, S. (ed.) Hydroxy-Piridones as Antifungal Agents with Special Emphasis on Onychomycosis. Springer, Berlin, Heidelberg; 1999, Chapter 8, pp. 45-50.
Adachi, "Storage and Oxidative Stability of O/W/ Nano-emulsions," Foods Food Ingredients J. Jpn., 2004, 209(11), 1 page (Abstract).
Adisen et al., "Topical tetracycline in the treatment of acne vulgaris," J Drugs Dermatol., Oct. 2008, 7(10):953-955.
Alcohol SDA 40B, 200 Proof. Material Safety Data Sheets [online]. Retrieved from the Internet: http://www.pharmco-prod.com/pages/MSDS/SDA.sub.--40B.sub.--200.pdf, on Dec. 9, 2008. MSDS 044, Revision 2.1, Revision Date Dec. 2005, 2 pages.
Alcohol, Wikipedia, the free encyclopedia [online]. Last modified on Apr. 23, 2014. Retrieved on May 17, 2014, http://en.wikipedia.org/wiki/Alcohol, 17 pages.
ALDARA™ (imiquimod) Cream. Highlights of Prescribing Information, Graceway Pharmaceuticals, LLC, Mar. 2007, 29 pages.
Allantoin, Römpp Online, retrieved on Sep. 23, 2015, https://roempp.thiem.de/roempp4.0/do/data/RD-O 1-01552, 5 pages.
Al-Mughrabi et al., "Effectiveness of Essential Oils and Their Combinations with Aluminum Starch Octenylsuccinate on Potato Storage Pathogens," TEOP, 2013, 16(1):23-31.
Ambrose et al., "In Vitro Studies of Water Activity and Bacterial Growth Inhibition of Sucrose-Polyethylene Glycol 400-Hydrogen Peroxide and Xylose-Polyethylene Glycol 400-Hydrogen Peroxide Pastes Used to Treat Infected Wounds," Antimicrobial Agents and Chemotherapy, Sep. 1991, 35(9):1799-1803.
Aminobenzoic Acid, Knovel, 2006, retrieved on Apr. 18, 2012, http://www.knovel.com/web/portal/knovel_content?p_p_id=EXT_KNOVEL_CONTENT . . . , 2 pages.

Anton et al., "Water-in-oil nano-emulsion formation by the phase inversion temperature method: a novel and general concept, a new template for nanoencapsulation," Proceedings of the 33rd Annual Meeting and Exposition of the Controlled Release Society, Jul. 2006, Vienna, Austria, 2 pages.
Arct et al., "Common cosmetic hydrophilic ingredients as penetration modifiers of flavonoids," International Journal of Cosmetic Science, Dec. 2002, 24(6):357-366 (Abstract Only).
Arisan, Kozmetic ve Kisisel Bakim Urunleri Grubu, retrieved on Dec. 10, 2008, http://www.arisankimya.com/kozmetik.htm, 8 pages.
Arquad HTL8-MS, AkzoNobel Functional Applications, retrieved on Mar. 18, 2013, Retrieved from the Internet: <URL: http://sc.akzonobel.com/en/fa/Pages/product-detail.aspx?prodID=8764>, 1 page.
Aslam et al. (2015) "Emerging drugs for the treatment of acne" Expert Opin Emerging Drugs, 20:91-101.
Atopic Dermatitis/Eczema, ibabydoc.com, Copyright 2000, retrieved on Jan. 30, 2010, http://www.ibabydoc.com/online/diseaseeczema.asp 6 pages.
Ausburger and Shangraw, "Bubble size analysis of high consistency aerosol foams and its relationship to foam rheology; Effects fo Container Emptying, Propellent Type, and Time," J. Pharma Sci, Apr. 1968, 57(4):624-631.
Austria, et al., "Stability of vitamin C derivatives in solution and topical formulations", Journal of Pharmaceutical and Biomedical Analysis, 1997, 15:795-801.
Barry and Badal, "Stability of minocycline, doxycycline, and tetracycline stored in agar plates and microdilution trays," Current Microbiology, 1978, 1:33-36.
Barry and Woodford, "Comparative bio-availability and activity of proprietary topical corticosteroid preparations: vasoconstrictor assays on thirty-one ointments," British J. Dermatology, 1975, 93:563-571.
Baskaran et al., "Poloxamer-188 improves capillary blood flow and tissue viability in a cutaneous burn wound," J. Surg. Res., 2001, 101(1):56-61.
Beauty Banter, "Interesting list of comedogenic ingredients!!!!!!!!!!!" QVC blog, Interesting list of comedogenic ingredients, 2014, 1-14.
Bell-Syer et al., "A systematic review of oral treatments for fungal infections of the skin of the feet," J. Dermatology. Treat., 2001, 12:69-74.
Ben-Et and Tatarsky "Application of NMR for the Determination of HLB Values of Nonionic Surfactants," Journal of the American Oil Chemists Society, Mar. 20, 1972, 49:499-500.
Bernstein and Harrison, "Effects of the Immunomodulating Agent R837 on Acute and Latent Herpes Simplex Virus Type 2 Infections," Antimicrobial Agents and Chemotherapy, Sep. 1989, 33(9):1511-1515.
Beuchat (Feb. 1983) "Influence of Water Activity on Growth, Metabolic Activities and Survival of Yeasts and Molds" J Food Prot, 46(2):135-141.
Blaney and Cook, "Topical use of tetracycline in the treatment of acne," Arch Dermatol, Jul. 1976, 112:971-973.
Blute et al., "Phase behaviour of alkyl glycerol ether surfactants", Physikalische Chemie/Physical Chemistry Tenside Surf. Det., 1998, 35(3):207-212.
Boehm et al., "Synthesis of high specific activity [.sup.3 H]-9-cis-retinoic acid and its application for identifying retinoids with unusual binding properties," J. Med. Chem., 1994, 37:408-414.
Brenes, et al., "Stability of Copigmented Anthocyanins and Ascorbic Acid in a Grape Juice Model System", J. Agric Food Chem, 2005, 53(1):49-56 (Abstract Only).
Brisaert, M. et al. (1996) "Investigation on the chemical stability of erythromycin in solutions using an optimization system" Pharm World Sci, 18(5):182-186.
Bronopol, 2-BROMO-2-NURO-1,3-Propanediol, Chemical land, Jul. 17, 2006, retrieved on Jun. 4, 2011, http://chemicalland21.com/specialtychem/perchem/BRONOPOL.html, 4 pages.
Brown et al., " Structural dependence of flavonoid interactions with Cu2+ ions: implications for their antioxidant properties," Biochem. J., 1998, 330:1173-1178.
Buck and Guth, "Treatment of Vaginal Intraepithelial Neoplasia (Primarily Low Grade) with Imiquimod 5% Cream", Journal of Lower Genital Tract Disease, 2003, 7(3):290-293.

(56) References Cited

OTHER PUBLICATIONS

Bucks et al., "Bioavailability of Topically Administered Steroids: A "Mass Balance" Technique," J. Investigative Dermatology, 1988, 91(1):29-33.
Bunker and Dowd, "Alterations in Scalp Blood Flow after the Epicutaneous Application of 3% Minoxidil and 0.1% Hexyl Nicotinate in Alopecia," British Society for Investigative Dermatology, Sep. 1986, 117(5):668-669.
Burn Patients Need Vitamin D Supplements, NUTRAingredients. com, Jan. 23, 2004, retrieved on May 5, 2010, http://www.nutraingredients.com/Research/Burn-patients-need-vitamin-D-supplements, 1 page.
Burton and Marshall, "Hypertrichosis due to minoxidil," British J. Dermatology, 1979, 101:593-595.
C12-15 Alkyl Benzoate, Paula's Choice Skincare, retrieved on Oct. 24, 2010, http://ww.cosmeticscop.com/cosmetic-ingredient-dictionary/definition/259/c12-15-alkyl-benzoate.aspx, 1 page.
Campos and Silva, "Ascorbic Acid and Its Derivatives in Cosmetic Formulations", Cosmetics and Toiletries, 2000, 115(6):59-62 (Abstract Only.
Can Tuberous Sclerosis Be Prevented?, Sharecare, 2002, retrieved on Aug. 29, 2013, <URL: http://www.sharecare.com/health/autosomal-dominant-genetic-disorders/can-tuberous-sclerosis-be-prevented;jsessionid=850579B60520A907DE75930E061E60E6>, 2 pages.
Canavan et al. (2016) "Optimizing Non-Antibiotic Treatments for Patients with Acne: A Review" Dermatol Ther, 6:555-578.
Carapeti et al., "Topical diltiazem and bethanechol decrease anal sphincter pressure and heal anal fissures without side effects," Dis Colon Rectum, 2000, 43(10):1359-1362.
CARBOWAX 1000MSDS, Material Safety Data Sheet for Polyethylene glycol 1000 MSDS, last updated Nov. 6, 2008, retrieved on Dec. 13, 2008, http://www.sciencelab.com/xMSDS-Polyethylene.sub.-glycol.sub.-1000-9926-622, 6 pages.
Carelli et al., "Effect of Vehicles on Yohimbine Permeation Across Excised Hairless Mouse Skin", Pharm Acta Helv, Aug. 1978, 73(3):127-134 (Abstract Only).
Causes of Psoriasis, retrieved on Sep. 9, 2010, http://www.quickcare.org/skin/causes-of0psoriasis.html, 3 pages.
Cetearyl Alcohol, Natural Wellbeing, Copyright 2001-2012, retrieved on Apr. 10, 2014, http://www.naturalwellbeing.com/learning-center/Cetearyl_Alcohol, 3 pages.
Chebil et al., "Solubility of Flavonoids in Organic Solvents," J. Chem. Eng. Data, 2007, 52(5):1552-1556 (Abstract Only).
Chemical Characteristics, The Olive Oil Source, © 1998-2015, retrieved on Jun. 12, 2015, http://www.oliveoilsource.com/page/chemical-characteristics, 10 pages.
Cheshire and Freeman, "Disorders of Sweating," Semin Neurol, 2003, 23(4):399-406.
Chevrant-Breton et al., "Etude du Traitement Capillaire <<Bioscalin>> dans les Alopecies Diffuses de la Femme", Gazette Medicale, 1986, 93(17):75-79 (English Abstract).
Chiang et al., "Bioavailability Assessment of Topical Delivery Systems: In Vitro Delivery of Minoxidil from Prototypical Semi-Solid Formulations", Int. J. Pharm, 1989, 49(2):109-114 (Abstract Only).
Chinnian et al., "Photostability Profiles of Minoxidil Solutions", PDA J. Pharm Sci Technol., Mar.-Apr. 1996, 50(2):94-98 (English Abstract).
Chollet et al., "Development of a Topically Active Imiquimod Formulation", Pharmaceutical Development and Technology, 1999, 4(1):35-43.
Chollet et al., "The Effect of Temperatures on the Solubility of Imiquimod in Isostearic Acid", Abstract 3031, Pharmaceutical Research, Nov. 1997, 14(11 Supplemental):S475.
Chrysos et al., "Effect of nifedipine on rectoanal motility," Dis Colon Rectum, Feb. 1996, 39(2):212-216.
Clobetasol Propionate Cream and Ointment, Apr. 2006, retrieved Jul. 3, 2014, http://dailymed.nlm.nih.gov/dailymed/archives/fdaDrugInfo.cfm?archiveid=994, 7 pages.

Cloez-Tayarani et al., "Differential effect of serotonin on cytokine production in lipopolysaccharide-stimulated human peripheral blood mononuclear cells: involvement of 5-hydroxytryptamine2A receptors," Int. Immunol., 2003, 15:233-240.
Coal Tars and Coal-Tar Pitches, Report on Carcinogens, Twelfth Edition, 2011, 3 pages.
Coatzee et al., "Acceptability and feasibility of Micralax® applicators and of methyl cellulose gel placebo for large-scale clinical trials of vaginal microbicides," AIDS, 2001, 15:1837-1842.
Coconut Oil, Wikipedia, the free encyclopedia, retrieved on Jul. 3, 2015, https://en.wikipedia.org/wiki/Coconut_oil, 8 pages.
Codex Standard for Olive Oils and Olive Pomace Oils Codex Stan 33-1981, Adopted in 1981, recently amended 2013, 8 pages.
Cole and Gazewood, "Diagnosis and Treatment of Impetigo," American Family Physical Website, 2007, http://www.aafp.org/afp, 6 pages.
Colloidal Silica, W.R. Grace & Co. Enriching Lives, Everywhere™, 2011, retrieved on Jun. 4, 2011, http://www.grace.com/engineeredmaterials/materialsciences/colloidalsilica/default.aspx, 4 pages.
Communication of a Notice of Opposition in European Application No. 03772600.7, dated Jan. 13, 2015, 36 pages.
Cook and Mortenson, "Nifedipine for treatment of anal fissures," Dis Colon Rectum, 2000, 43(3):430-431.
Craig, D.Q.M. et al. (Jul. 1994) "An investigation into the structure and properties of Carbopol 934 gels using dielectric spectroscopy and oscillatory rheometry" J Controlled Rel, 30(3):213-223 (Abstract).
Cremophor a Grades, BASF The Chemical Company, Jan. 2008, 6 pages.
Croda Crop Care, Arlacel 165, 2011, retrieved on Aug. 3, 2015, http://www.crodapersonalcare.com/home.aspx?view=dtl&d=content&s=157&r=401&p=2578&productName=&inciname=&application=&subapplication=&productfunction=&consumerbenefit=&prodID=1926, 2 pages.
Croda Product Care Europe, Cetomacrogol 1000, 2011, retrieved on Aug. 3, 2015, http://www.crodapersonalcare.com/home.aspx?view=dtl&d=content&s=157&r=273&p=1859&productName=&inciname=&chemicaltype=&application=&subapplication=&productfunction=&consumerbenefit=&prodID=27, 1 page.
Crohn'S Disease, Merck Manual Home Edition, retrieved on Jan. 16, 2013, <http://www.merckmanuals.com/home/digestive_disorders/inflammatory_bowel_diseases_ibd/crohn_disease.html?qt=crohn's disease&alt=sh>, 3 pages.
Cunha, "Minocycline versus Doxycycline in the treatment of Lyme Neuroborreliosis," Clin. Infect. Diseases, 2000, 30: 237-238.
Dacarbazine, Chemical Book, 2010, retrieved on Oct. 18, 2013, <URL: http://www.chemicalbook.com/ChemicalProductProperty_EN_CB7710656.htm>, 2 pages.
Dalby et al., "Determination of Drug Solubility in Aerosol Propellants," Pharmaceutical Research, 1991, 8(9):1206-1209.
Dawber and Rundegren, "Hypertrichosis in Females Applying Minoxidil Topical Solution and in Normal Controls", JEADV, 2003, 17:271-275.
Denatonium Benzoate, retrieved Dec. 9, 2008, http://www.newdruginfo.com/pharmaceopeia/usp28/v28230/usp28nf23s0_m-22790.htm, 2 pages.
Dentinger, et al., "Stability of Nifedipine in an Extemporaneously Compounded Oral Solution", American Journal of Health-System Pharmacy, 2003, 60(10):1019-1022 (English Abstract).
Derivative, Merriam Webster Online Dictionary, retrieved on Jul. 5, 2008, http://www.merriam-webster.com/cgi-bin/dictionary?book=dictionary&va=derivative, 1 page.
Devos and Miller, "Antisense Oligonucleotides: Treating neurodegeneration at the Level of RNA," Neurotherapeutics, 2013, 10:486-497.
Diethyltoluamide, Wikipedia, the free encyclopedia, retrieved on Sep. 11, 2015, https://de.wikipedia.org/wiki/Diethyltoluamid, 12 pages.
Dimethylphthalate, Wikipedia, the free encyclopedia, retrieved on Sep. 11, 2015, http://de.wikipedia.org/wiki/Dimethylphthalat, 8 pages.
Disorder, American Heritage Dictionary of the English Language, 2007, retrieved on Oct. 9, 2010, http://www.credoreference.com/entry/hmdictenglang/disorder, 1 page.
Draelos, "Antiperspirants and the Hyperhidrosis Patients," Dermatologic Therapy, 2001, 14:220-224.

(56) References Cited

OTHER PUBLICATIONS

Drug Index—Dacarbazine, BC Cancer Agency, Jun. 2004, retrieved on Oct. 18, 2013, <URL:http://www.bccancer.bc.ca/HPI/DrugDatabase/DrugIndexPro/Dacarbazine.htm>, 6 pages.
Drugfuture, Chemical Index Database, "Sorbitan Esters" Monograph [online]. Retrieved from: http://www.drugfuture.com/chemdata/sorbitan-esters.html, on Jul. 1, 2016, 2 pages.
Durian et al., "Scaling behavior in shaving cream," The American Physical Society, Dec. 1991, 44(12):R7902-7905.
Durmortier et al., "A review of poloxamer 407 pharmaceutical and pharmacological characteristics," Pharmaceutical Res., Dec. 2006, 23(12):2709-2728.
E7023 Ethanol 200 Proof (Absolute), Sigma-Aldrich Co., © 2008, retrieved on Dec. 9, 2008, http://www.sigmaaldrich.com/catalog/ProductDetail.do?N4=E7023SIAL&N5=SEAR- CH.sub.--CONCAT.sub.--PNOBRAND.sub.--KEY&F=SPEC, 2 pages.
Ebadi et al., "Healing effect of topical nifedipine on skin wounds of diabetic rats," DARU, 2003, 11(1):19-22.
Edens et al., "Storage Stability and Safety of Active Vitamin C in a New Dual-Chamber Dispenser", Journal of Applied Cosmetology, 1999, 17(4):136-143 (English Abstract).
Edirisinghe et al., "Effect of fatty acids on endothelium-dependent relaxation in the rabbit aorta", Clin Sci, Aug. 2006, 1 1 1 (2): 145-51.
Edwards, "Imiquimod in Clinical Practice," J. Am Acad Dermatol., Jul. 2000 43(1, Pt 2):S12-S17 (English Abstract).
Effendy and Maibach "Surfactants and Experimental Irritant Contact Dermatitis." Contact Dermatol., 1995, 33:217-225.
Elias and Ghadially, "The aged epidermal permeability barrier," Clinical Geriatric Medicine, Feb. 2002, 103-120.
Ellis et al., "The Treatment of Psoriasis with Liquor Carbonis Detergens," J. Invest Dermatology, 1948, 10:455-459.
Emulsifiers With HLB Values, The Herbarie, retrieved on Aug. 5, 2009, http://www.theherbarie.com/files/resources-center/formulating/Emulsifiers- .sub.--HLB.sub.--Values.pdf, 3 pages.
Esposito et al., "Nanosystems for Skin Hydration: A Comparative Study," International Journal of Cosmetic Science, 2007, 29: 39-47.
Established ("Approved") Excipients, Encyclopedia of Pharmaceutical Technology, Second Edition, © 2002, vol. 3, 2146-2147.
Ethylene Oxide Derivatives: An Essence of Every Industry, retrieved on Jul. 12, 2011, http://www.emulsifiers.in/ethylene_oxide_derivatives2.htm, 3 pages.
European Patent Application No. 03772600.7 (Patent No. 1556009): Communication of a Notice of Opposition, dated Sep. 23, 2015, 42 pages.
European Patent Application No. 03772600.7 (Patent No. 1556009): Communication of a Notice of Opposition, dated September24, 2015, 30 pages.
European Patent Application No. 03772600.7 (Patent No. 1556009): Reply of the Patent Proprietor to the Notices of Opposition, dated May 9, 2016, 134 pages.
European Patent Application No. 03772600.7 (Patent No. 1556009): Summons to Attend Oral Proceedings, dated Jun. 30, 2016, 19 pages.
European Patent Application No. 03772600.7 (Patent No. 1556009): Interlocutory Decision in Opposition Proceedings, dated Feb. 3, 2017, 54 pages.
European Patent Application No. 03772600.7 (Patent No. 1556009): Minutes of Oral Proceedings, dated Feb. 3, 2017, 6 pages.
Excessive Sweating, Merck Manual Home Edition, Oct. 2007, retrieved on Apr. 14, 2011, www.merckmanuals.com/home/print/sec18/ch206/ch206c.html, 2 pages.
Fantin et al., "Critical influence of resistance to streptogramin B-type antibiotics on activity of RP 59500 (Quinupristin-dalfopristin) in experimental endocarditis due to *Staphylococcus aureus*," Antimicrob Agents and Chemothery, Feb. 1995, 39:400-405.
Farahmand et al., "Formulation and Evaluation of a Vitamin C Multiple Emulsion", Pharmaceutical Development and Technology, May 2006, 11(2):255-261 (English Abstract).
Flick, Cosmetic and Toiletry Formulations, 2nd Edition, Copyright 1996, vol. 5, 251-309.
Floyd, "Silicone Surfactants: Applicants in the Personal Care Industry," Silicone Surfactants, 1999, Chapter 7, 181-207.
Fluhr et al., "Glycerol accelerates recovery of barrier function in vivo," Acta Derm. Venereol, 1999, 79:418-421.
Foamix Pharmaceuticals Ltd. (May 1, 2017) "Foamix Pharmaceuticals Announces Plans for Additional Phase 3 Trial for FMX101 in Moderate to Severe Acne," Press Release [online]. Retrieved from: http://www.foamix.co.il/news.asp?nodeID=564&itemID=204, on Jun. 12, 2017, 5 pages.
Foamix Pharmaceuticals, Statement: Use of Luviquat FC 370, Approved by Yohan Hazot, May 3, 2016, 3 pages.
Fontana, "Water Activity: Why It is Important for Food Safety," International Conference on Food Safety, Nov. 16-18, 1998, 177-185.
Fontana (Apr. 1999) "Pharmaceutical Applications for Water Activity" Pharmaceutical Online [online]. Retrieved from https://www.pharmaceuticalonline.com/doc/pharmaceutical-applications-for-water-activit- . . . , on Jan. 17, 2018 (4 pages).
Frankel, A.J. et al. (2010) "Coal Tar 2% Foam in Combination with a Superpotent Corticosteroid Foam for Plaque Psoriasis. Case Report and Clinical Implications" J Clin Aesthet Dermatol, 3(10):42-45.
Fully-Refined Paraffin Wax (FRP Wax), Industrial Raw Materials LLC, Feb. 21, 2008, retrieved on Aug. 22, 2013, <http://irmwax.com/Wax/Paraffin/fully_refined.asp> 1 page.
Gallarate et al., "On the Stability of Ascorbic Acid in Emulsified Systems for Topical and Cosmetic Use", International Journal of Pharmaceutics, 1999, 188:233-241.
Galligan et al., "Adhesive Polyurethane Liners for Anterior Restorations," J. Dent. Res., Jul.-Aug. 1968, 629-632.
Garti et al. "Sucrose Esters microemulsions," J. Molec. Liquids, 1999, 80:253-296.
Gas Gangrene, Merck Manual Home Edition, 2008, retrieved on Jan. 16, 2013, <http://www.merckmanuals.com/home/infections/bacterial_infections/gas_gangrene.html?qt=gas gangrene&alt=sh>1 page.
Gelbard et al. "Primary Pediatric Hyperhidrosis: A Review of Current Treatment Options," Pediatric Dermatology, 2008, 25(6):591-598.
Gels, UNC: The Pharmaceutics and Compounding Laboratory, retrieved on Aug. 25, 2014, http://pharmlabs.unc.edu/labs/gels/agents/htm, 4 pages.
Ghica, M.V. et al. (2011) "Design and optimization of some collagen-minocycline based hydrogels potentially applicable for the treatment of cutaneous wound infections" Pharmazie, 66:853-861.
Gill et al., "Adverse Drug Reactions in a Paediatric Intensive Care Unit," Acta Paediatric, 1995, 84:438-441.
Gladkikh, "Ascorbic Acid and Methods of Increasing its Stability in Drugs", Translated from Khimiko-Farmatsevticheskii Zhurnal, 1970, 4(12):37-42.
Glaser and Ballard, "Hyperhidrosis: A Comprehensive and Practical Approach to Patient Management," Expert Rev. Dermatol., Oct. 2006, 1(6):773-775.
Google Search Strategy for Minocycline Solubility, retrieved on Aug. 15, 2013, <http://www.googl.com/search?rls=com.microsoft%3Aen-us%3AIE-SearchBox&q-melocycline+solubility>, 1 page.
Graves et al., "Structure of Concentrated Nanoemulsions," The Journal of Chemical Physics, Apr. 1, 2005, 122:134703, 6 pages.
Griffin, "Calculation of HLB Values of Non-Ionic Surfactants," Journal of the Society of Cosmetic Chemists, May 14, 1954, 249-256.
Groveman et al., "Lack of Efficacy of Polysorbate 60 in the Treatment of Male Pattern Baldness", Arch Intern Med, 1985, 145:1454-1458.
Gschnait et al., "Topical Indomethacin Protects from UVB and UVA Irradiation," Arch. Dermatol. Res., 1984, 276:131-132.
Hakan et al., "The protective effect of fish oil enema in acetic acid and ethanol induced colitis," The Turkish Journal of Gastroenterology, 2000, 11(2):155-161.

(56) References Cited

OTHER PUBLICATIONS

Hall, "Diaper Area Hemangiomas: A Unique Set of Concerns," retrieved on Dec. 1, 2008, http://members.tripod.com/.about.Michelle.sub.--G/diaper.html, 8 pages.
HALLSTAR® GMS SE/AS, retrieved on Jun. 4, 2011, http://www.hallstar.com/pis/php?product=1H022, 1 page.
Hammer et al., "Anti-Microbial Activity of Essential Oils and other Plant extracts," J. Applied Microbiology, 1999, 86:985-990.
Hargreaves, "Chemical Formulation, An Overview of Surfactant-Based Preparations Used in Everyday Life", The Royal Society of Chemistry, 2003, 114-115.
Harrison et al., "Effects of cytokines and R-837, a cytokine inducer, on UV-irradiation augmented recurrent genital herpes in guinea pigs", Antiviral Res., 1991, 15(4):315-322.
Harrison et al., "Modification of Immunological Responses and Clinical Disease During Topical R-837 Treatment of Genital HSV-2 Infection," Antiviral Research, 1988, 10:209-224.
Harrison et al., "Pharmacokinetics and Safety of Imiquimod 5% Cream in the Treatment of Actinic Keratoses of the Face, Scalp, or Hands and Arms", Arch. Dermatol. Res., Jun. 2004, 296(1):6-11 (English Abstract).
Harrison et al., "Posttherapy Suppression of Genital Herpes Simplex Virus (HSV) Recurrences and Enhancement of HSV-Specific T-Cell Memory by Imiquimod in Guinea Pigs", Antimicrobial Agents and Chemotherapy, Sep. 1994, 38(9):2059-2064.
Harry, "Skin Penetration," The British Journal of Dermatology and Syphilis, 1941, 53:65-82.
Hashim et al., "Tinea versicolor and visceral leishmaniasis," Int J Dermatol., Apr. 1994; 33(4):258-259 (Abstract).
Haute.De, "Substance (INCI-Designation): Triethanolamine" [online]. Retrieved on Sep. 14, 2015, http://www.haut.de/service/inci/anzeige&id=I6384&query=Triethanolamine&funktio . . . ; German with English translation, 3 pages.
Haw, "The HLB System: A Time Saving Guide to Surfactant Selection," Presentation to the Midwest Chapter of the Society of Cosmetic Chemists, Mar. 9, 2004, 39 pages.
Healy, "Gelled Emollient Systems for Controlled Fragrance Release and Enhanced Product Performance," Cosmetics and toiletries, 2002, 117(2): 47-54.
Heart Failure, The Merck Manual, 2008, retrieved Oct. 9, 2010, http://www.merck.com/mmhe/sec03/ch025/ch025a.html, 12 pages.
Helmenstine, "Surfactant Definition—Chemistry Glossary Definition of Surfactant," About.com Chemistry, retrieved on Mar. 5, 2012, http://chemistry.about.com/od/chemistryglossary/g/surfactant.htm, 1 page.
Hepburn, "Cutaneous leishmaniasis," Clin Exp Dermatol, Jul. 2000, 25(5):363-370 (Abstract).
HLB Systems, Pharmcal.tripod.com, retrieved on Sep. 17, 2010, http://pharmcal.tripod.com/ch17.htm, 3 pages.
HLB-Numbers, Sigma Aldrich, 2009, retrieved on Feb. 2, 2009, http://www.sigmaaldrich.com/materials-science/micro-and-nanoelectronics/l- ithography-nanopatterning/hlb-numbers.html, 3 pages.
How to Have a Healthy Libido in Mid-Life and Beyond, GreenWillowTree.com, Jan. 2001, retrieved on Jul. 28, 2012, http://www.greenwillowtree.com/Page.bok?file=libido.html, 5 pages.
Hubbe, Colloidal Silica, Mini-Encyclopedia of Papermaking Wet-End Chemistry: Additives and Ingredients, their Composition, Functions, Strategies for Use, Feb. 1, 2001, retrieved on Jun. 4, 2011, http://www4.ncsu.edu/~hubbe/CSIL.htm, 2 pages.
Human Immunodeficiency Virus Infection, Merck Manual Home Edition, 2008, retrieved on Jan. 16, 2013, <http://www.merckmanuals.com/home/infections/human_immunodeficiency_virus_hiv_infection/human_immunodeficiency_virus_infection.html?qt=human immunodeficiency virus infection&alt=sh >, 11 pages.
Hwang et al., "Isolation and identification of mosquito repellents in Artemisia vulgaris," J. Chem. Ecol., 1985, 11: 1297-1306.
ICI Americas Inc., "Meaning of HLB Advantages and Limitations" Chapter 1 in The HLB System. A Time-Saving Guide to Emulsifier Selection. Wilimington, Delaware: 1980; pp. 1-4.

Ikuta et al., "Scanning Electron Microscopic Observation of Oil/Wax/Water/Surfactant System", Journal of SCCJ, 2004, 34(4):280-291 (English Abstract).
Indomethacin, Aug. 15, 2009, retrived on Jun. 3, 2011, http://it03.net/com/oxymatrine/down/1249534834.pdf, 3 pages.
Innocenzi et al., "An Open-Label Tolerability and Effacy Study of an Aluminum Sesquichlorhydrate Topical Foam in Axillary and Palmar Primary Hyperhidrosis," Dermatologic Therapy, 2008, 21:S27-S30.
Izquierdo et al. "Formation and Stability of Nano-Emulsions Prepared Using the Phase Inversion Temperature Method," Langmuir, 2002, 18(1):26-30 (Abstract).
Jan, "Troubled Times: Detergent Foam," retrieved on Feb. 9, 2012, http://zetatalk.com/health/theal17c.htm, 2 pages.
Joseph, "Understanding foams & foaming," University of Minnesota, May 1997, http://www.aem.umn.edu/people/faculty/joseph/archive/docs/understandingfoams.pdf, 8 pages.
Kalkan et al., "The Measurement of Sweat Intensity Using a New Technique," Tr. J. of Medical Sciences, 1998, 28:515-517.
Kanamoto et al., "Pharmacokinetics of two rectal dosage forms of ketoprofen in patients after anal surgery," J Pharmacobiodyn., Mar. 1988, 11(3):141-145.
Kang et al., "Enhancement of the Stability and Skin Penetration of Vitamin C by Polyphenol", Immune Netw., Dec. 2004, 4(4):250-254 (English Abstract).
Kanicky, J.R. and D.O. Shah (2002) "Effect of Degree, Type, and Position of Unsaturation on the pKa of Long-Chain Fatty Acids" J Colloid and Interface Science, 256:201-207.
Karasu et al., "Practice Guideline for the Treatment of Patients with Major Depressive Disorder," Second Edition, Apr. 2000, 78 pages.
KATHON™ CG, Rohm and Haas Personal Care, Jun. 2006, 9 pages.
Kaur et al., "Formulation Development of Self Nanoemulsifying Drug Delivery System (SNEDDS) of Celecoxib for Improvement of Oral Bioavailability," Pharmacophore, 2013, 4(4):120-133.
Kim, "Stability of Minoxidil in Aqueous Solution", Yakhak Hoechi, 1986, 30(5):228-231 (English Abstract).
Kinnunen and Hannuksela, "Skin reactions to hexylene glycol," Contact Dermatitis, Sep. 1989, 21(3):154-158.
Kircik, L.H. and S. Kumar (Aug. 2010) "Scalp Psoriasis" J Drugs Dermatol, 9(8 Suppl):s101-s137.
Kleber et al., "Practice Guideline for the Treatment of Patients with Substance Use Disorders," Aug. 2006, 276 pages.
Klucel Hydroxypropylcellulose; Chemical and Physical Properties, Hercules Limited, copyright 1986, retrieved on Aug. 25, 2014, http://legacy.library.ucsf.edu/tid/cnf81a99/pdf, 35 pages.
Knight et al., "Topical diltiazem ointment in the treatment of chronic anal fissure," Br. J. Surg., 2001, 88(4):553-556.
Koerber, "Humectants and Water Activity," Water Activity News, 2000, 8 pages.
Kolb, "Emulsifiers, emollients and solubilizers for personal care", pp. 1-9, accessed Jun. 20, 2018.
Kreuter, "Nanoparticles and microparticles for drug and vaccine delivery," J. Anat., 1996, 189:503-505.
Kucharekova et al., "Effect of a lipid-rich emollient containing ceramide 3 in experimentally induced skin barrier dysfunction," Contact Dermatitis, Jun. 2002, 46:331-338.
Kumar et al., "Application of Broad Spectrum Antiseptic Povidone Iodine as Powerful Action: A Review," Journal of Pharmaceutical Science and Technology, 2009, 1(2):48-58.
Kwak et al. "Study of Complete Transparent Nano-Emulsions which Contain Oils." IFSCC Conference, Seoul Korea, Sep. 2003, 3 pages.
Laboratory 6- Characteristics of Surfactants and Emulsions, retrieved on Jan. 29, 2010, http://web.archive.org/web/20000106225413/http://pharmacy.wilkes.edu/kibbeweb/lab7.html, 5 pages.
Lautenschlager, "A Closer Look on Natural Agents: Facts and Future Aspects," Kosmetic Konzept Kosmetische Praxis, 2006, 5:8-10.
Le Vine et al., "Components of the Goeckerman Regimen," Journal of Investigative Dermatology, 1979, 73:170-173.
Lebwohl and Ali, "Treatment of psoriasis. Part 1. Topical therapy and phototherapy," J. Am Acad Dermatol, Oct. 2001, 487-498.

(56) References Cited

OTHER PUBLICATIONS

Lebwohl et al., "A randomized, double-blind, placebo-controlled study of clobestasol propionate 0.05% foam in the treatment of nonscalp psoriasis," International Journal of Dermatology, 2002, 41(5): 269-274.
Lee et al., "Historical review of melanoma treatment and outcomes," Clinics in Dermatology, 2013, 31: 141-147.
Lee et al., "The Stabilization of L-Ascorbic Acid in Aqueous Solution and Water-in-Oil-in-Water Double Emulsion by Controlling pH and Electrolyte Concentration," J. Cosmet. Sci., Jan./Feb. 2004, 55:1-12.
Leive et al., "Tetracyclines of various hydrophobicities as a probe for permeability of *Escherichia coli* outer membrane," Antimicrobial Agents and Chemotherapy, 1984, 25:539-544.
Leunapon-F, LEUNA-Tenside, Screenshot, retrieved on Sep. 18, 2015, http://www.leuna-tenside.de/2006_7_14_3143/2006_8_7 5750/2006_8_7 241/cas-68439-49-6, 1 page.
Leung and Robinson, "Bioadhesive Drug Delivery," American Chemical Society, 1991, Chapter 23, 350-366.
Li et al., "Solubility Behavior of Imiquimod in Alkanoic Acids", Pharmaceutical Research, Abstract 3029, Nov. 1997,14(11):S475, 2 pages.
Licking Vaginal Dryness Without a Prescription, retrieved on Dec. 14, 2008, http://www.estronaut.com/a/vag.sub.--dryness.htm, 3 pages.
Lin et al., "Ferulic acid stabilizes a solution of vitamins c and e and doubles its photoprotection of skin," J Invest Dermatol, 2005, 125:826-832.
Lippacher et al., "Liquid and Semisolid SLN Dispersions for Topical Application: Rheological Characterization," European Journal of Pharmaceutics and Biopharmaceutics, 2004, 58:561-567.
Livingstone and Hubel, "Segregation of form, color, movement, and depth: Anatomy, physiology, and perception," Science, May 1988, 240:740-749.
Lupke and Kemper, "The HET-CAM Test: An Alternative to the Draize Eye Test," FD Chem. Toxic., 1986, 24:495-196.
Lupo, "Antioxidants and Vitamins in Cosmetics", Clinics in Dermatology, 2001, 19:467-473.
Luviquat Polymer Grades, BASF The Chemical Company, May 2012, 32 pages.
Mailer, "Chemistry and quality of olive oil," NSW Dept. of Primary Industries, Aug. 2006, Primefact 227, 1-4.
Martindale: The Complete Drug Reference, 33rd Edition, Jun. 2002, Pharmaceutical Press, pp. 1073 and 1473.
Martindale: The Complete Drug Reference, Thirty-third edition, Bath Press, London, 2002, 1073 and 1473.
Martindale: The Extra Pharmacopoeia, Twenty-eighth edition, The Pharmaceutical Press, London, 1982, 862-864.
Material Safety Data Sheet, Luvitol EHO, Caelo, Nov. 28, 2013, 4 pages.
Material Safety Data Sheet, Butane, Gas Innovations, Sep. 7, 2007, 3 pages.
Material Safety Data Sheet, Carbon Dioxide, Airgas, Feb. 11, 2016, 11 pages.
Material Safety Data Sheet, Dimethyl Ether, Airgas, May 14, 2015, 12 pages.
Material Safety Data Sheet, Hydroxyethyl Cellulose, Sigma-Aldrich, Jan. 14, 2004, http://terpconnect.umd.edu/-choi/MSDS/Sigma-Aldrich/HYDROXYETHYL%20CELLULOSE, 5 pages.
Material Safety Data Sheet, Hydroxyethyl Cellulose, Sigma-Aldrich, Jan. 2004, 5 pages.
Material Safety Data Sheet, Liquor carbonis detergens, Caelo, Nov. 28, 2013, 5 pages.
Material Safety Data Sheet, Mineral Oil, Macron Fine Chemicals, Oct. 24, 2011, 6 pages.
Material Safety Data Sheet, N-Butane, Airgas, May 7, 2015, 13 pages.
Material Safety Data Sheet, Nitrous Oxide, Airgas, Feb. 11, 2016, 11 pages.
Material Safety Data Sheet, Propane, Airgas, Oct. 20, 2015, 12 pages.
Material Safety Data Sheet, Science Lab.com, Polyethylene Glycol 200, MSDS, Nov. 6, 2008, 6 pages.
Material Safety Data Sheet, USP, Progesterone, Apr. 26, 2006, 5 pages.
Mead, "Electrostatic Mechanisms Underlie Neomycin Block of the Cardiac Ryanodine Receptor Channel (RyR2)," Biophysical Journal, 2004, (87): 3814-3825.
Messenger et al., "Minoxidil: Mechanisms of Action on Hair Growth", British Journal of Dermatology, 2004, 150:186-194.
Metronidazole (Veterinary—Systemic), The United States Pharmacopeial Convention, 2007, retrieved on Sep. 10, 2009, www.usp.org/pdf/EN/veterinary/metronidazole.pdf, 4 pages.
Metz et al., "A Phase I Study of Topical Tempol for the Prevention of Alopecia Induced by Whole Brain Radiotherapy," Clinical Cancer Research, Oct. 2004, 10:6411-6417.
Meucci et al., "Ascorbic Acid Stability in Aqueous Solutions", Acta Vitaminol Enzymol, 1985, 7(3-4):147-153 (English Abstact).
Milton, D.T. et al. (2006) "A Phase I/II Study of Weekly High-Dose Erlotinib in Previously Treated Patients With Nonsmall Cell Lung Cancer" Cancer, 107:1034-1041.
Mineral Oil USP, U.S. Department of Health & Human Services, Chemical Abstracts Service Registry No. 8012-95-1, 2011, 7 pages.
Minocycline (DB01017), Drug Bank, Feb 8, 2013, retrieved on Aug. 15, 2013, <http://www.drugbank.ca/drugs/DB01017>, 10 pages.
Minocycline, Wikipedia, the free encyclopedia, retrieved on Oct. 21, 2011, http://en.wikipedia.org/wiki/Minocycline, 7 pages.
MMP Inc., International Development and Manufacturing, "Formulating specialties," retrieved on Feb. 2, 2010, http://mmpinc.com, 3 pages.
Molan, "World Wide Wounds: Honey as a topical antibacterial agent for treatment of infected wounds," Dec. 2001, retrieved May 7, 2008, http://www.worldwidewounds.com/2001/november/Molan/honey-as-topical-agent.html, 13 pages.
*Molins PLC v. Textron Inc.*, 48 F.3d 1172, 33 USPQ2d 1823 (Fed. Cir. 1995), 19 pages.
Morgan et al., "Enhanced Skin Permeation of Sex Hormones with Novel Topical Spray Vehicles," Journal of Pharmaceutical Sciences, Oct. 1998, 87(10):1213-1218.
Mousse, Merriam-Webster Online Dictionary, retrieved on Dec. 8, 2008, http://www.merriam-webster.com/dictionary/mousse, 2 pages.
Musial, W. and A. Kubis (2004) "Carbopols as factors buffering triethanolamine interacting with artificial skin sebum" Polim Med, 34(4):17-30 (Abstract).
Natural Skincare Authority, "Disodium EDTA: Cosmetic Toxin Data," 2011, retrieved on Nov. 17, 2013, http://www.natural-skincare-authority.com/DISODIUM-EDTA.html, 4 pages.
Neutrogena Clinical SPF 30 Facial Lifting Wrinkle Treatment, Apr. 28, 2010, retrieved on Sep. 11, 2010, http://www.cosmetoscope.com/2010/04/neutrogea-clinical-with-johnson-johnsons-cytomimic-techology/, 5 pages.
Neves et al., "Rheological Properties of Vaginal Hydrophilic Polymer Gels," Current Drug Delivery, 2009, 6:83-92.
New Nanomaterials to Deliver Anticancer Drugs to Cells Developed, Science Daily, Jun. 2007, retrieved on Oct. 14, 2013, <URL: http://www.sciencedaily.com/releases/2007/06/070607112931.htm>, 3 pages.
Nietz, "Molecular orientation at surfaces of solids," J. Phys. Chem., 1928, 32(2): 255-269.
Niram Chemicals, Chemical products—Cetostearyl Alcohol, Cetyl Alcohol, Stearyl Alcohol and Polyethylene Glycol Importer & Supplier, retrieved on Jul. 17, 2012, http://www.indiamart.com/niramchemicals/chemicals.html, 7 pages.
Novartis "LAMISIL®" Product Information, T2001-29 [online]. Retrieved from: http://www.fda.gov/downloads/Drugs/DrugSafety/PostmarketDrugSafetyInformationforPatientsandProviders/ucm052213.pdf; Published: Apr. 2001, 8 pages.
Oh et al., "Antimicrobial activity of ethanol, glycerol monolaurate or lactic acid against Listeria moncylogenes,"Int. J. Food Microbiology, 1993, 20:239-246.
Olsen et al., "A Multicenter, Randomized, Placebo-Controlled, Double-Blind Clinical Trial of a Novel Formulation of 5% Minoxidil Topical Foam Versus Placebo in the Treatment of Androgenetic Alopecia in Men", J. Am. Acad Dermatol, Nov. 2007, 57:767-774.

(56) References Cited

OTHER PUBLICATIONS

OM-Cinnamate, MakingCosmetics.com, retrieved on Sep. 26, 2009, http://www.makingcosmetics.com/sunscreens/OM-Cinnamate-p102.html, 1 page.
Omega-9 Fatty Acids (Oleic Acid), Orthomolecular.org, Dec. 2004, retrieved on Aug. 15, 2014, http://orthomolecular.org/nutrients/omega9.html, 1 page.
Optimization of Nano-Emulsions Production by Microfluidization, European Food Research and Technology. Sep. 2007, 22:5-6 (English Abstract).
Oranje et al., "Topical retapamulin ointment, 1%, versus sodium fusidate ointment, 2%, for impetigo: a randomized, observer-blinded, noninferiority study," Dermatology, 2007, 215(4):331-340.
Osborne and Henke, "Skin Penetration Enhancers Cited in the Technical Literature," Pharm. Technology, Nov. 1997, 21(11):58-86.
Padhi et al., "Phospho-olivines as positive-electrode materials for rechargeable lithium batteries," J. Electrochemical Soc., Apr. 1997, 144(4): 1188-1194.
Padi and Kulkarni, "Minocycline prevents the development of neuropathic pain, but not acute pain: possible anti-inflammatory and antioxidant mechanisms," Eur J. Pharmacol, 2008, 601:79-87.
Pakpayat et al., "Formulation of Ascorbic Acid Microemulsions with Alkyl Polyglycosides", European Journal of Pharmaceutics and Biopharmaceutics, 2009, 72:444-452.
Palamaras and Kyriakis, "Calcium antagonists in dermatology: a review of the evidence and research-based studies," Derm. Online Journal, 2005, 11(2):8.
Passi et al., "Lipophilic antioxidants in human sebum and aging," Free Radical Research, 2002,36(4):471-477.
Pharmaceutical Benefits Advisory Committee (PBAC) of Australia. PBAC Public Summary Document—Nov. 2014 Meeting (5 pages).
Pendergrass et al., "The shape and dimension of the human vagina as seen in three-dimensional vinyl polysiloxane casts," Gynecol Obstet. Invest., 1996, 42(3):178-82 (Abstract).
Penreco, "Intelligent Gel Technology Product Specifications," Rev. Jun. 2016 (2 pages).
Permethrin (Insecticide), Wildpro, retrieved on Jun. 4, 2015, http://wildpro.twycrosszoo.org/S/00Chem/ChComplex/perm.htm, 5 pages.
Perotti et al., "Topical Nifedipine With Lidocaine Ointment vs. Active Control for Treatment of Chronic Anal Fissure," Dis Colon Rectum, 2002, 45(11):1468-1475.
Polystyrene, Wikipedia the free encyclopedia, retrieved Apr. 21, 2014, http://web.archive.org/web/20060312210423/http://en.wikipedia.org/wiki/Polystyrene, 4 pages.
PPG-40-PEG-60 Lanolin Oil, Environmental Working Group, 2010, retrieved on May 19, 2010, http://www.cosmeticsdatabase.com/ingredient/722972/PPG-40-PEG-60_Lanolin_Oil/?ingred06=722972., 3 pages.
Prevent, The American Heritage Dictionary of the English Language, 2007, retrieved on Oct. 9, 2010, http://www.credoreference.com/entry/hmdictenglang/prevent, 1 page.
Product Data Sheet for Meclocycline, bioaustralis fine chemicals, Jun. 28, 2013, 1 page.
PROMIUS™ Pharma LLC (2012) Scytera™ (coal tar) Foam, 2%. Product Information Sheet, 1 page.
Prud'homme et al., Foams: theory, measurements and applications, Marcel Dekker, Inc., 1996, 327-328.
Purcell, "Natural Jojoba Oil Versus Dryness and Free Radicals," Cosmetics and Toiletries Manufacture Worldwide, 1988, 4 pages.
Purdy et al., "Transfusion-transmitted malaria: unpreventable by current donor exclusion guidelines?" Transfusion, Mar. 2004, 44:464.
Raschke et al., "Topical Activity of Ascorbic Acid: From In Vitro Optimization to In Vivo Efficacy", Skin Pharmacology and Physiology, Jul./Aug. 2004, 17(4):200-206 (Abstract).
Ravet et al., "Electroactivity of natural and sythetic triphylite," J. Power Sources, 2001, 97-98: 503-507.
Raymond, "Iodine as an Aerial Disinfectant," J. Hygiene, May 1946, 44(5):359-361.

Reaction Rate, Wikipedia, the free encyclopedia, retrieved on Dec. 18, 2011, en.wikipedia.org/wiki/Reaction_rate, 6 pages.
Receptacle, Merriam Webster, retrieved on Jul. 12, 2011, http://www.merriam-webster.com/dictionary/receptacle, 1 page.
Refina, "Viscosity Guide for Paints, Petroleum & Food Products," accessed Mar. 4, 2015, http://www.refina.co.uk/webpdfs/info_docs/Viscosity_guide_chart.pdf, 2 pages.
Regulation (EC) No. 2003/2003 of the European Parliament and of the Council, Official Journal of the European Union, Oct. 13, 2003, 2 pages.
Repa et al. "All-trans-retinol is a ligand for the retinoic acid receptors," Proc. Natl. Acad Sci, USA, Aug. 1993, 90: 7293-7297.
Reregistration Eligibility Decision for Pyrethrins, EPA, Jun. 7, 2006, 108 pages.
Richwald, "Imiquimod", Drugs Today, 1999, 35(7):497 (Abstract).
Rieger and Rhien, "Emulsifier Selection/HLB," Surfactants in Cosmetics, 129, 1997.
Rohstoffinformationen, Hoffmann Mineral, 2008, 8 pages (with English translation).
Rosacea, Clinuvel Pharmaceuticals, 2010, retrieved on Sep. 9, 2010, http://clinuvel.com/skin-conditions/common-skin-conditions/rosacea#h0-6-prevention, 5 pages.
Rowe et al., "Glyceryl Monooleate," Handbook of Pharmaceutical Excipients, 2011, 10 pages, retrieved on Dec. 19, 2011, http://www.medicinescomplete.com/mc/excipients/current/1001938996.htm?q=glyceryl%20monooleate&t=search&ss=text&p=l# hit.
Rowe et al., "Octyldodecanol," Handbook of Pharmaceutical Excipients, 2011, 9 pages, retrieved on Dec. 19, 2011, URL:http://www.medicinescomplete.com/mc/excipients/current/1001942450.htm?q=octyldodecanol&t=search&ss=text&p=l# hit.
Rowe et al., "Sucrose Palmitate," Handbook of Pharmaceutical Excipients, 2011, 11 pages, retrieved on Dec. 19, 2011, URL:http://www.medicinescomplete.com/mc/excipients/current/EXP-TD-c46-mn0001.htm?q=sucrose%20stearate&t=search&ss=text&p=l# hit.
Rowe et al., "Sucrose Stearate," Handbook of Pharmaceutical Excipients, 2011, 11 pages, retrieved on Dec. 19, 2011, URL:http://www.medicinescomplete.com/mc/excipients/current/EXP-TD-cll-mnOOOl-mnOOOl.htm?q=sucrose%20stearate&t=search&ss=text&p=3# hit.
Rses (Oil in Refrigerator Systems, Service Application Manual, 2009).
Rutledge, "Some corrections to the record on insect repellents and attractants," J. Am. Mosquito Control Assoc, Dec. 1988, 4(4): 414-425.
Sakai et al., "Characterization of the physical properties of the stratum corneum by a new tactile sensor," Skin Research and Technology, Aug. 2000, 6:128-134.
Sanders et al., "Stabilization of Aerosol Emulsions and Foams," J. Soc. Cosmet. Chem., 1970, 21:377-391.
Sarpotdar, P.P. et al. (Jan. 1986) "Effect of Polyethylene Glycol 400 on the Penetration of Drugs Through Human Cadaver Skin In Vitro" J Pharma Sci, 75(1):26-28.
Savin et al., "Tinea versicolor treated with terbinafine 1% solution," Int J. Dermatol, Nov. 1999; 38(11): 863-865.
Schaefer, "Silicone Surfactants," Tenside Surf. Det., 1990, 27(3): 154-158.
Schmidt, "*Malassezia furfur*: a fungus belonging to the physiological skin flora and its relevance in skin disorders," Cutis, Jan. 1997, 59(1):21-24 (Abstract).
Schmolka, "A review of block polymer surfactants," Journal of the American Oil Chemists Society, Mar. 1977, 54: 110-116.
Schott, "Rheology," Remington's Pharmaceutical Sciences, 17th Edition, 1985, 330-345.
Schutze, "Iodine and Sodium Hypochlorite as Wound Disinfectants," The British Medical Journal, 1915, 921-922.
Sciarra, "Aerosol Technology," Kirk-Othmer Encyclopedia of Chemical Technology, Jul. 2012, 20 pages.
Scientific Discussion for the Approval of Aldara, EMEA, 2005, 10 pages.
Scott, "A Practical Guide to Equipment Selection and Operating Techniques," Pharmaceutical Dosage Forms: Disperse Systems, vol. 3, Copyright 1998, 291-362.

(56) References Cited

OTHER PUBLICATIONS

Scully et al., "Cancers of the oral mucosa treatment and management," Medscape Drugs, Diseases and Procedures, Apr. 20, 2012, retrieved on Oct. 12, 2013, <http://emedicine.medscape.com/article/1075729-treatment>, 10 pages.
Seborrheic Dermatitis, retrieved on Sep. 9, 2010, http://www.cumc.columbia.edu/student/health/pdf/R-S/Seborrhea%20Dermatitis.pdf, 2 pages.
Security Datasheet, Luvitol EHO, Cetearyloctanoat, Nov. 27, 2013, 10 pages.
Sehgal, "Ciclopirox: a new topical pyrodonium antimycotic agent: A double-blind study in superficial dermatomycoses," British Journal of Dermatology, 1976, 95:83-88.
Sharp, "Oil," Dictionary of Chemistry, Copyright 1990, 286.
Shear et al., "Pharmacoeconomic analysis of topical treatments for tinea infections," Pharmacoeconomics, Mar. 1995, 7(3):251-267.
Shear, Vocabulary.com, retrieved on Aug. 23, 2013, <URL: https://www.vocabulary.com/dictionary/shear>, 3 pages.
Sheer, Vocabulary.com, retrieved on Aug. 23, 2013, https://www.vocabulary.com/dictionary/sheer, 3 pages.
Shemer, A. et al. (2016) "Topical minocycline foam for moderate to severe acne vulgaris: Phase 2 randomized double-blind, vehicle-controlled study results" J Am Acad Dermatol, 74(6):1251-1252.
Sheu et al., "Effect of Tocopheryl Polyethylene Glycol Succinate on the Percutaneous Penetration of Minoxidil from Water/Ethanol/Polyethylene Glycol 400 Solutions," Drug Dev. Ind. Pharm., Jun. 2006, 32(5):595-607 (Abstract).
Shim et al., "Transdermal Delivery of Mixnoxidil with Block Copolymer Nanoparticles," J. Control Release, Jul. 2004, 97(3):477-484 (Abstract).
Shrestha et al., "Forming properties of monoglycerol fatty acid esters in nonpolar oil systems," Langmuir, 2006, 22: 8337-8345.
Sigma-Aldrich. http://www.sigmaaldrich.com/catalog/product/sial/p1754?lang=en® ion=. Published:Mar. 5, 2014.
Sigma Aldrich, "Surfactants Classified by HLB Numbers" 2017 [online]. Retrieved from the Internet: www.sigmaaldrich.com/materials-science/material-science-products.html?TablePage=22686648, on Jul. 8, 2017 (3 pages).
Silicone, Oxford Dictionaries Online, retrieved on Apr. 19, 2011, http://www.oxforddictionaries.com/definition/silicone?view=uk, 1 page.
Simoni et al., "Retinoic acid and analogs as potent inducers of differentiation and apoptosis. New promising chemopreventive and chemotherapeutic agents in oncology," Pure Appl Chem., 2001, 73(9):1437-1444.
Simovic et al., "The influence of Processing Variables on Performance of O/W Emulsion Gels Based on Polymeric Emulsifier (Pemulen® TR-2NF)," International Journal of Cosmetic Science, Dec. 2001, 21(2)119-125 (Abstract).
Smith, "Hydroxy acids and skin again," Soap Cosmetics Chemical Specialties, Sep. 1993, 69(9):54-59.
Smith, "Sore Nipples," Breastfeeding Mom's Sore Nipples / Breastfeeding Basics, retrieved on Feb. 8, 2012, http://breastfeedingbasics.com/articles/sore-nipples, 9 pages.
SOFTEMUL—165: Product Data Sheet, Mohini Organics PVT Ltd, retrieved Apr. 10, 2014, http://www.mohiniorganics.com/Softemul165.html#, 1 page.
Solans et al., "Overview of basic aspects of microemulsions," Industrial Applications of Microemulsions, New York, 1997, 1-17.
SOLODYN® (Minocycline HCI, USP) Prescribing Information; revised Jun. 2016, 2 pages.
Sonneville-Aubrun et al., "Nanoemulsions: A New Vehicle for Skincare Products," Advances in Colloid and Interface Science, 2004, 108-109:145-149.
Spa Collections, AG & Co. Essential oil workshop, retrieved on Jan. 31, 2010, http://www.agworkshop.com/p3.asp, 1 page.
Squillante et al., "Codiffusion of propylene glycol and dimethyl isosorbide in hairless mouse skin," European J. Pharm. Biopharm., 1998, 46:265-271.
Squire and Goode, "A randomized, single-blind, single-centre clinical trial to evaluate comparative clinical efficacy of shampoos containing ciclopirox olamine (1.5%) and salicylic acid (3%), or ketoconazole (2%, Nizoral) for the treatment of dandruff/seborrhoeic dermatitis," Dermatolog Treat., Jun. 2002, 13(2):51-60 (Abstract).
Sreenivasa et al., "Preparation and Evaluation of Minoxidil Gels for Topical Application in Alopecia," Indian Journal of Pharmaceutical Sciences, 2006, 68(4):432-436.
Sreenivasan, B. et al. (1956)"Studies on Castor Oil. I. Fatty Acid Composition of Castor Oil" J Am Oil Chem Soc, 33:61-66.
Stehle et al., "Uptake of minoxidil from a new foam formulation devoid of propylene glycol to hamster ear hair follicles," J. Invest. Dermatol., 2005, 124(4): A101 (Abstract).
Sugisaka et al., "The Physicochemical Properties of Imiquimod, The First Imidazoquinoline Immune Response Modifier", Pharmaceutical Research, Nov. 1997, 14(11):S475, Abstract 3030.
*Sun Pharmaceutical Industries Ltd.* v. *Eli Lilly and Co.*, 611 F.3d 1381, 95 USPQ2d 1797 (Fed. Cir. 2010),7 pages.
Sung, J.H. et al. (2010) "Gel characterisation and in vivo evaluation of minocycline-loaded wound dressing with enhanced wound healing using polyvinyl alcohol and chitosan" Intl J Pharmaceut, 392:232-240.
Surfactant, Wikipedia, the free encyclopedia, retrieved on Oct. 24, 2010, http://en.wikipedia.org/wiki/Surfactant, 7 pages.
Tadros, "Surfactants in Nano-Emulsions." Applied Surfactants: Principles and Applications, 2005, 285-308.
Tamarkin, D. (2013) "Foam: A Unique Delivery Vehicle for Topically Applied Formulations" in: Formulating Topical Applications—a Practical Guide. Dayan N, Ed., Carol Stream, IL: CT Books, Chapter 9, pp. 233-260.
Tan et al., "Effect of Carbopol and PolyvinYlpyrrolidone on the Mechanical, Rheological, and Release Properties of Bioadhesive Polyethylene Glycol Gels," AAPS PharmSciTech, 2000; 1(3) Article 24, 10 pages.
Tanhehco, "Potassium Channel Modulators as Anti-Inflammatory Agents", Expert Opinion on Therapeutic Patents, Jul. 2001, 11(7):1137-1145 (Abstract).
Tarumoto et al., "Studies on toxicity of hydrocortisone 17-butyrate 21-propionate -1. Acute toxicity of hydrocortisone 17-butyrate 21-propionate and its analogues in mice, rats and dogs (author's transl)," J Toxicol Sci., Jul. 1981, 6:1-16 (Abstract).
Tata et al., "Penetration of Minoxidil from Ethanol Propylene Glycol Solutions: Effect of Application Volume on Occlusion," Journal of Pharmaceutical Sciences, Jun. 1995, 84(6):688-691.
Tata et al., "Relative Influence of Ethanol and Propylene Glycol Cosolvents on Deposition of Minoxidil into the Skin," Journal of Pharmaceutical Sciences, Jul. 1994, 83(10):1508-1510.
Tavss et al., "Anionic detergent-induced skin irritation and anionic detergent-induced pH rise of bovine serum albumin," J. Soc. Cosmet. Chem., Jul./Aug. 1988, 39:267-272.
TCI America, Safety Data Sheet; Product Name: Squalane. Product Code: H0096 [online]. Retrieved from: https://www.spectrumchemical.com/MSDS/TCI-H0096.pdf. Revised: Oct. 6, 2014, 5 pages.
Tea Tree Oil, LookChem, Chemical Abstract No. 68647-73-4, 2012, 2 pages.
The HLB System—A Time-Saving Guide to Emulsifier Selection, ICI Americas Inc., Mar. 1980, 1-22.
The United States Pharmacopeia: The National Formulary, USP23/NF18, US Pharmacopoeia, Jan. 1995, p. 10-14.
Third Party Submission in Published Patent Application, U.S. Appl. No. 12/014,088, filed Feb. 4, 2009, 4 pages.
Thorgeirsdottir et al., "Antimicrobial activity of monocaprin: a monoglyceride with potential use as a denture disinfectant," Acta Odontologica Scandinavica, Feb. 2006, 64:21-26 (Abstract only).
Tirumala et al., "Abstract: D28.00011: Enhanced order in thinfilms of Pluronic (A-B-A) and Brij (A-B) Block copolymers blended with poly (acrylic acid)," Session D28: Block Copolymer Thin Films, Mar. 13, 2006, 1 page, Abstract.
Tjulandin, S. et al. (2013) "Phase I, dose-finding study of AZD8931, an inhibitor of EGFR (erbB1), HER2 (erbB2) and HER3 (erbB3) signaling, in patients with advanced solid tumors" Invest New Drugs, 32(1):145-153.
Todd et al., "Volatile Silicone Fluids for Cosmetic Formulations," Cosmetics and Toiletries, Jan. 1976, 91:27-32.

(56) References Cited

OTHER PUBLICATIONS

Torma et al., "Biologic activities of retinoic acid and 3,4-Didehydroretinoic acid in human keratinocytes are similar and correlate with receptor affinities and transactivation properties," J. Invest. Dermatology, 1994, 102: 49-54.
Torres-Rodriguez, "New topical antifungal drugs," Arch Med Res., Winter 1993, 24(4): 371-375 (Abstract).
Toxicology and Carcinogenesis Studies of T-Butyl Alcohol (CAS No. 75-65-0) in F344/N Rats and B6C3F1 Mice (Drinking Water Studies), May 1995, retrieved on Dec. 9, 2008, http://ntp.niehs.nih.gob/?objectid=-0709F73D-A849-80CA-5FB784E866B576D1, 4 pages.
Trofatter, "Imiqimod in clinical practice", European Journal of Dermatology, Oct./Nov. 1998, 8(7 Supp.):17-19 (Abstract).
Tsai et al., "Drug and Vehicle Deposition from Topical Applications: Use of In Vitro Mass Balance Technique with Minoxidil Solutions", J. Pharm. Sci., Aug. 1992, 81(8):736-743 (Abstract).
Tsai et al., "Effect of Minoxidil Concentration on the Deposition of Drug and Vehicle into the Skin," International Journal of Pharmaceutics, 1993, 96(1-3):111-117 (Abstract).
Tsai et al., "Influence of Application Time and Formulation Reapplication on the Delivery of Minoxidil through Hairless Mouse Skin as Measured in Franz Diffusion Cells," Skin Pharmacol., 1994, 7:270-277.
Tyring, "Immune-Response Modifiers: A New Paradigm in the Treatment of Human Papillomavirus," Current Therapeutic Research, Sep. 2000, 61(9):584-596 (Abstract).
Tzen et al. "Surface Structure and Properties of Plant Seed Oil Bodies," Department of Botany and Plant Sciences, University of California, Riverside, California 92521, Apr. 15, 1992, 9 pages.
Tzen et al., "Lipids, proteins and structure of seed oil bodies from diverse species," Plant Physiol., 1993, 101:267-276.
U.S. Final Office Action for U.S. Appl. No. 11/430,437, Tamarkin et al., dated Dec. 16, 2008, 24 pages.
U.S. Office Action for U.S. Appl. No. 11/430,437, Tamarkin et al., dated May 9, 2008, 27 pages.
U.S. Office Action from U.S. Appl. No. 11/430,599, dated Jul. 28, 2008, 59 pages.
Uner et al., "Skin Moisturizing Effect and Skin Penetration of Ascorbyl Palmitate Entrapped in Solid Lipid Nanoparticles (SLN) and Nanostructured Lipid Carriers (NLC) Incorporated into Hydrogel," Pharmazie, 2005, 60:751-755.
United States Standards for Grades of Olive Oil and Olive-Pomace Oil, United States Dept. of Agriculture, Oct. 25, 2010, 21 pages.
Valenta, "Effects of Penetration Enhancers on the In-vitro Percutaneous Absorption of Progesterone," J. Pharm. Pharmacol., 1997, 49: 955-959.
Van Cutsem et al., "The anti-inflammatory effects of ketoconazole," J. Am. Acad. Dermatol., Aug. 1991, 25(2):257-261.
Van Slyke, "On the measurement of buffer values and on the relationship of buffer value to the dissociation constant of the buffer and the concentration and reaction of the buffer solution," J. Biol. Chem., 1922, 52:525-570.
Vera et al., "Scattering optics of Foam," Applied Optics, Aug. 20, 2001, 40(24):4210-4214.
Veron et al., "Stability of Minoxidil Topical Formulations", Ciencia Pharmaceutica, 1992, 2(6):411-414 (Abstract).
VERSAGEL® M Series, Mineral Oil Moisturizing Gels. Product Bulletin, retrieved from https://archive.org/web/, as archived Oct. 15, 2006, 3 pages.
View of NCT01171326 on Dec. 7, 2010, ClinicalTrials.gov archive, Dec. 7, 2010, retrieved on Sep. 9, 2013, http://clinicaltrials.gov/archive/NCT01171326/2010_12_07, 4 pages.
View of NCT01362010 on Jun. 9, 2011, ClinicalTrials.gov archive, Jun. 9, 2011, retrieved on Sep. 9, 2013, < http://clinicaltrials.gov/archive/NCT01362010/2011_06_09>, 3 pages.
Wang and Chen, "Preparation and surface active properties of biodegradable dextrin derivative surfactants," Colloids and Surfaces A: Physicochemical and Engineering Aspects, 2006, 281(1-3):190-193.
WATER JEL Technologies, "Material Safety Data Sheet for Neomycin Antibiotic Ointment," Dec. 1, 2004, 7 pages.
WebMD (2014) "Psoriasis Health Center" [online]. Retrieved Apr. 13, 2015; retrieved from the Internet: http://www.webmd.com/skin-problems-and-treatments/psoriasis/psoriasis-symptoms, 3 pages.
WebMD (2014) "Understanding Rosacea—the Basics" [online]. Retrieved Apr. 13, 2015; retrieved from the Internet: http://www.webmd.com/skin-problems-and-treatments/understanding-rosacea-basics (5 pages).
WebMD (2017) "User Reviews & Ratings—Scytera topical" [online]. Retrieved Mar. 1, 2017; retrieved from the Internet: http://www.webmd.com/drugs/drugreview-151502-Scytera+topical.aspx?drugid=151502&drugname=Scytera+topical&sortby=3 (2 pages).
Weindl et al., "Hyaluronic acid in the treatment and prevention of skin diseases: molecular biological, pharmaceutical and clinical aspects," Skin Pharmacology and Physiology, 2004, 17: 207-213.
Wenninger et al., "International Cosmetic Ingredient Dictionary and Handbook," The Cosmetic, Toiletry, and Fragrance Association, Washington, DC., 1997, vol. 1, 4 pages.
Wermuth, "Similarity in drugs: reflections on analogue design," Drug Discovery Today, Apr. 2006, 11(7/8):348-354.
What Is CP Serum, Skin Biology, retrieved on Dec. 1, 2008, http://web.archive.org/web/20030810230608/http://www.skinbio.com/cpserum.- html, 21 pages.
What Is TSC?, Tuberous Sclerosis Alliance, Jan. 1, 2005, retrieved on Feb. 6, 2014, http://www.tsalliance.org.pages.aspx?content=2, 3 pages.
Williams et al., "Acne vulgaris," Lancet, 2012, 379:361-372.
Williams et al., "Scale up of an olive/water cream containing 40% diethylene glycol monoethyl ether," Dev. Ind. Pharm., 2000, 26(1):71-77.
Williams et al., "Urea analogues in propylene glycol as penetration enhancers in human skin," International Journal of Pharmaceutics, 1989, 36, 43-50.
Wormser et al., "Protective effect of povidone-iodine ointment against skin lesions induced by sulphur and nitrogen mustards and by non-mustard vesicants," Arch. Toxicol., 1997, 71, 165-170.
Wormser, "Early topical treatment with providone-iodine ointment reduces, and sometimes prevents, skin damage following heat stimulus," Letter to the Editor, Burns, 1998, 24:383.
Wrightson, W.R. et al. (1998) "Analysis of minocycline by high-performance liquid chromatography in tissue and serum" J Chromatography B, 706:358-361.
Wu et al., "Interaction of Fatty Acid Monolayers with Cobalt Nanoparticles," Nano Letters, 2004, 4(2): 383-386.
Yamada et al., "Candesartan, an angiotensin II receptor antagonist, suppresses pancreatic inflammation and fibrosis in rats," J. Pharmacol. Exp. Ther., 2003, 307(1):17-23.
Zeichner, J.A. (2010) "Use of Topical Coal Tar Foam for the Treatment of Psoriasis in Difficult-to-treat Areas" J Clin Aesthet Dermatol, 3(9):37-40.
Zinc Oxide, Knovel, 2006, retrieved on Apr. 18, 2012, http://www.knovel.com/web/portal/knovel_content?p_p_id=EXT_KNOVEL_CONTENT . . . , 2 pages.
Ziolkowsky, "Moderne Aerosolschaume in der Kosmetik (Modern Aerosol Foams in Chemical and Marketing Aspects)" Seifen-Ole-Fette-Wachse, Aug. 1986, 112(13): 427-429 (with English translation).

TOPICAL TETRACYCLINE COMPOSITIONS

CROSS REFERENCE TO RELATED APPLICATIONS

This application is a continuation of U.S. application Ser. No. 15/591,733, filed May 10, 2017; which is a continuation of U.S. application Ser. No. 14/595,882, filed Jan. 13, 2015; which is a continuation of U.S. application Ser. No. 14/469,792, filed Aug. 27, 2014; which is a continuation of U.S. application Ser. No. 14/327,040, filed Jul. 9, 2014; which is a continuation of U.S. application Ser. No. 13/499,475, filed Sep. 14, 2012; which is a U.S. National Stage entry under 35 U.S.C. § 371 of International Application No. PCT/IB2010/002617, filed Oct. 1, 2010; which claims the benefit of priority under 35 U.S.C. § 119(e) to U.S. Provisional Application No. 61/248,144 filed Oct. 2, 2009 and entitled "Surfactant-Free Water-Free Foamable Compositions, Breakable Foams and Their Uses"; U.S. Provisional Application No. 61/322,148 filed Apr. 8, 2010 and entitled "Surfactant-Free Water-Free Foamable Compositions, Breakable Foams and Their Uses"; U.S. Provisional Application No. 61/349,911 filed May 31, 2010 and entitled "Surfactant-Free Water-Free Foamable Compositions, Breakable Foams and Their Uses"; U.S. Provisional Application No. 61/385,385 filed Sep. 22, 2010 and entitled "Surfactant-Free Water-Free Foamable Compositions, Breakable Foams and Gels and Their Uses"; U.S. Provisional Application No. 61/331,126 filed May 4, 2010 and entitled "Compositions, Gels and Foams with Rheology Modulators and Uses Thereof"; and U.S. Provisional Application No. 61/380,568 filed Sep. 7, 2010 and entitled "Surfactant-Free Water-Free Foamable Compositions and Breakable Foams and Their Uses"; all of which are herein incorporated in their entirety by reference.

BACKGROUND

Tetracyclines are broad-spectrum antibiotic, which are routinely used orally for the treatment of dermatological conditions, such as acne and rosacea. However, despite their high therapeutic value, tetracyclines are very unstable, and they are known to be incompatible with many formulation excipients, including water, various protic substances and oxidizing agents.

Topical tetracycline was the first topical antibiotic approved for the treatment of acne, its use has been limited because of the skin penetration problems of the active ingredient (Adişen E et al, "Topical tetracycline in the treatment of acne vulgaris", J Drugs Dermatol. 2008; 7:953-5). The vehicle of this product is an ointment base, comprising petrolatum (which is greasy and unusable in the case of facial treatment of acne and rosacea).

Tetracycline hydrophobic compositions intended to be mixed with an external source of protic liquid are known. They comprise a hydrophobic non-hygroscopic silicone thickening agent, preferably a silicone elastomer, in concentrations of more than 5%. This mixing results in substantial solubilization of the tetracycline, thus rendering it "suitable for topical delivery. Such a product, which requires mixing two components prior to administration by the patient is cumbersome and has no or little practical or viable value; and furthermore, it would degrade and form degradation products if left for a while prior to treatment.

SUMMARY

The present application relates to oleaginous gel formulations, foamable formulations and foams comprising tetracycline, which are stable and their therapeutic uses.

The application also relates to foamable formulations and foam without surfactants; and or without surfactants and polymeric agents. In one or more embodiments the hydrophobic solvents are provided as part of a drug carrier. For example certain drugs require hydrophobic solvents in order to solubilize them.

In one or more other embodiments, the hydrophobic solvents are provided to facilitate or enhance the intradermal penetration or delivery of a drug. In one or more additional cases, the hydrophobic solvents are provided to have an occlusive effect at the target site, for example where the site of treatment is a damaged skin and the occlusive effect of hydrophobic solvents is desirable. The present application further relates to compositions comprising hydrophobic solvents and their uses. The application further describes semi solid gel compositions that liquefy on application of mild shear force such as gentle rubbing.

In one or more embodiments there is provided topical therapeutic hydrophobic breakable composition comprising
  a. a carrier comprising
    i. about 60% to about 99% by weight of at least one hydrophobic oil
    ii. at least two viscosity-modifying agents selected from the group consisting of a fatty alcohol, a fatty acid and a wax
  b. a tetracycline antibiotic
  characterized in that
  (i) at least part of the tetracycline antibiotic is suspended in the composition;
  (ii) the viscosity of the composition is at least about 30% higher than the viscosity of the carrier without the tetracycline antibiotic; and is higher than the viscosity of the hydrophobic oil and the tetracycline antibiotic without the viscosity modifying agents;
  (iii) the amount of viscosity modifying agents can optionally be reduced by at least an amount by weight that would have increased the viscosity of the carrier without the tetracycline antibiotic by at least 30%;
  wherein the tetracycline is chemically stable in the composition for at least six months wherein more than about 90% of the tetracycline has not broken down;
  wherein when packaged in an aerosol container to which is added a liquefied or compressed gas propellant the composition affords upon release from the container a breakable foam of at least good quality that breaks easily upon application of shear force.

It is known in the art that foams can easily be formulated based on high amounts of water, in combination with surface active agents, foam adjuvants and polymeric agents. As described in the literature, hydrophobic solvents can have a de-foaming effect which makes the formulation of foams based on hydrophobic solvents—challenging. To overcome this challenge, the prior art requires the use of substantial levels of surfactants that act as foaming agents. Surface active agents are known to be irritating, especially ionic surface active agents and repeated use can cause dry skin and so it is desirable to reduce their use in pharmaceutical compositions intended to treat skin or mucosa. The prior art further teaches the incorporation of foam adjuvants, such as fatty alcohols and fatty acids, as foam boosting agents and also the incorporation of polymeric agents (e.g. gelling agents) as foam stabilizers, which can prolong the collapse time of a foam. Waxes may also be introduced into these surfactant based formulations but as will be appreciated, waxes, which are solids at ambient temperature, can easily precipitate.

The technical problems to be overcome in formulating oleaginous carriers and pharmaceutical compositions with hydrophobic solvent (a) without surfactants; and/or (b) without polymeric agents and/or (c) without water and/or (e) without short chain alcohols and/or (f) without polyols; are multifold and include finding a suitable substitute for surfactant which provides foam generating properties; finding a suitable replacement that preferably does not need to have a foam adjuvant present with the surfactant (substitute), which if present would inter alia help to boost the foam and as an aid to the surfactant and preferably does not need to have a polymeric agent present with the surfactant (substitute), which if present would inter alia help prolong stability of the foam.

It was surprisingly discovered in the present invention, that surface active agents can be advantageously eliminated and replaced by viscosity-modifying agents consisting of a fatty alcohol, a fatty acid and a wax in the context of hydrophobic solvent based-foams. Waxes possess several advantages over other foaming agents such as excellent skin compatibility, almost no chemical reactivity which ensures active ingredients stability and efficient skin occlusion which helps reducing skin water loss and can enhance skin penetration of active agents. Albeit waxes introduce their own additional problems into formulating foamable compositions and foams, including their tendency to solidify and precipitate out from a formulation and to block canister valves, against which the formulations need to be designed so that the formulations are not negatively disturbed upon adding an effective amount of propellant and that the formulations are shakable and are homogenous and can readily reform at least upon mild or reasonable shaking prior to use.

Another challenge is how to adjust the rheology as primarily expressed in the viscosity of the formulation before and after adding propellant so that before it can exhibit gel like properties and that after addition it is shakable in the canister, Additionally the composition should be capable of generating a foam that when applied to a target is neither a liquid nor very viscous but is comfortable an convenient for application. Further, costs of toxicology and trials may be substantially reduced where the gel and the foam are capable of showing equivalency for pharmaceutical purposes.

Incorporated in or added to the above is the aspect of how to provide formulations in which unstable active ingredients, such as tetracyclines, which readily degrade can nevertheless remain sufficiently chemically stable for prolonged periods of time such that allowing for a reasonable or acceptable amount of breakdown (for example as may be accepted by a regulatory drug authority) they remain capable of providing a therapeutic effect or prevention or remission of a disorder or disease (hereinafter "chemically stable"). A further challenge is providing and delivering a composition in which the active agent is homogenous, especially when the active agent is not dissolved. Additionally the formulations should avoid the use of substances, which can be irritating if applied to a sensitive target or can cause depletion or drying or soreness on repeated use.

Incorporated in or added to the above is the aspect of how to provide physically stable formulations which are at least short term stable upon release from the pressurized container and not break as a result of exposure to skin temperature. Foams which are structurally stable on the skin for at least one minute are termed "short term stable". In another aspect of physically stability the foamable formulation including propellant remains homogenous and does not separate to any significant extent for at least one minute after being shaken (hereinafter "physically stable").

In one aspect, a topical therapeutic hydrophobic breakable composition includes a carrier comprising about 60% to about 99% by weight of at least one hydrophobic oil and at least one viscosity-modifying agents selected from the group consisting of a fatty alcohol, a fatty acid and a wax; and a tetracycline antibiotic, characterized in that at least part of the tetracycline antibiotic is suspended in the composition and the viscosity of the composition is at least about 30% higher than the viscosity of the carrier without the tetracycline antibiotic; and is higher than the viscosity of the hydrophobic oil and the tetracycline antibiotic without the viscosity modifying agents; and wherein after storage at 25° C. for at least two months the composition retains at least 90% of the tetracycline initially present in the composition; and wherein when packaged in an aerosol container to which is added a liquefied or compressed gas propellant the composition affords upon release from the container a breakable foam of at least good quality that breaks easily upon application of shear force.

In one or more embodiments, the tetracycline at least 95% or at least 97% of the tetracycline initially present is present after at least two months.

In one or more embodiments, the tetracycline at least 90% or at least 95% or at least 97% of the tetracycline initially present is present after at least three months.

In one or more embodiments, the tetracycline at least 90% or at least 95% or at least 97% of the tetracycline initially present is present after at least six months.

In one or more embodiments, the amount of tetracycline present is determined by HPLC.

In one or more embodiments, the increase in viscosity is a synergistic increase such that the combined viscosity of the carrier and the viscosity of the hydrophobic oil and the tetracycline antibiotic is less than the viscosity of the composition.

In one or more embodiments, the hydrophobic breakable vehicle is in the form of a gel prior to addition of propellant; wherein said gel liquefies and spreads easily upon application of mild shear force.

In one or more embodiments, the hydrophobic breakable vehicle is in the form of a foam; wherein said foam has a collapse time of greater than about 3 minutes.

In one or more embodiments, the ratio of composition other than propellant to propellant is from about 100:1 to about 100:25.

In one or more embodiments, the at least one hydrophobic oil is selected from the group consisting of a mineral oil, a hydrocarbon oil, an ester oil, an ester of a dicarboxylic acid, a triglyceride oil, an oil of plant origin, an oil from animal origin, an unsaturated or polyunsaturated oil, a diglyceride, a PPG alkyl ether, an essential oil, a silicone oil, liquid paraffin, an isoparaffin, a polyalphaolefin, a polyolefin, polyisobutylene, a synthetic isoalkane, isohexadecane, isododecane, alkyl benzoate, alkyl octanoate, C12-C15 alkyl benzoate, C12-C15 alkyl octanoate, arachidyl behenate, arachidyl propionate, benzyl laurate, benzyl myristate, benzyl palmitate, bis (octyldodecyl stearoyl) dimer dilinoleate, butyl myristate, butyl stearate, cetearyl ethylhexanoate, cetearyl isononanoate, cetyl acetate, cetyl ethylhexanoate, cetyl lactate, cetyl myristate, cetyl octanoate, cetyl palmitate, cetyl ricinoleate, decyl oleate, diethyleneglycol diethylhexanoate, diethyleneglycol dioctanoate, diethyleneglycol diisononanoate, diethyleneglycol diisononanoate, diethylhexanoate, diethylhexyl adipate, diethylhexyl malate, diethylhexyl succinate, diisopropyl adipate, diisopropyl dimerate, diisopropyl sebacate, diisostearyl dimer dilinoleate, diisostearyl fumerate, dioctyl malate, dioctyl sebacate, dodecyl oleate, ethylhexyl palmitate, ester derivatives of lanolic acid, ethylhexyl cocoate, ethylhexyl ethylhexanoate, ethylhexyl hydroxystearate, ethylhexyl isononanoate, ethylhexyl palmytate, ethylhexyl pelargonate, ethylhexyl stearate, hexadecyl stearate, hexyl laurate, isoamyl laurate, isocetyl isocetyl behenate, isocetyl lanolate, isocetyl palmitate, isocetyl stearate, isocetyl salicylate, isocetyl stearate, isocetyl stearoyl stearate, isocetearyl octanoate, isodecyl ethylhexanoate, isodecyl isononanoate, isodecyl oleate, isononyl isononanoate, isodecyl oleate, isohexyl decanoate, isononyl octanoate, isopropyl isostearate, isopropyl lanolate, isopropyl laurate, isopropyl myristate, isopropyl palmitate, isopropyl stearate, isostearyl behenate, isostearyl citrate, isostearyl erucate, isostearyl glycolate, isostearyl isononanoate, isostearyl isostearate, isostearyl lactate, isostearyl linoleate, isostearyl linolenate, isostearyl malate, isostearyl neopentanoate, isostearyl palmitate, isostearyl salicylate, isostearyl tartarate, isotridecyl isononanoate, isotridecyl isononanoate, lauryl lactate, myristyl lactate, myristyl myristate, myristyl neopentanoate, myristyl propionate, octyldodecyl myristate, neopentylglycol dicaprate, octyl dodecanol, octyl stearate, octyl palmitate, octyldodecyl behenate, octyldodecyl hydroxystearate, octyldodecyl myristate, octyldodecyl stearoyl stearate, oleyl crucate, oleyl lactate, oleyl oleate, propyl myristate, propylene glycol myristyl ether acetate, propylene glycol dicaprate, propylene glycol dicaprylate, propylene glycol dicaprylate, maleated soybean oil, stearyl caprate, stearyl heptanoate, stearyl propionate, tocopheryl acetate, tocopheryl linoleate, glyceryl oleate, tridecyl ethylhexanoate, tridecyl isononanoate, triisocetyl citrate, alexandria laurel tree oil, avocado oil, apricot stone oil, barley oil, borage seed oil, calendula oil, canelle nut tree oil, canola oil, caprylic/capric triglyceride castor oil, coconut oil, corn oil, cotton oil, cottonseed oil, evening primrose oil, flaxseed oil, groundnut oil, hazelnut oil, glycereth triacetate, glycerol triheptanoate, glyceryl trioctanoate, glyceryl triundecanoate, hempseed oil, jojoba oil, lucerne oil, maize germ oil, marrow oil, millet oil, neopentylglycol dicaprylate/dicaprate, olive oil, palm oil, passionflower oil, pentaerythrityl tetrastearate, poppy oil, propylene glycol ricinoleate, rapeseed oil, rye oil, safflower oil, sesame oil, shea butter, soya oil, soybean oil, sweet almond oil, sunflower oil, sysymbrium oil, syzigium aromaticum oil, tea tree oil, walnut oil, wheat germ glycerides, wheat germ oil, PPG-2 butyl ether, PPG-4 butyl ether, PPG-5 butyl ether, PPG-9 butyl ether, PPG-12 butyl ether, PPG-14 butyl ether, PPG-15 butyl ether, PPG-15 stearyl ether, PPG-16 butyl ether, PPG-17 butyl ether, PPG-18 butyl ether, PPG-20 butyl ether, PPG-22 butyl ether, PPG-24 butyl ether, PPG-26 butyl ether, PPG-30 butyl ether, PPG-33 butyl ether, PPG-40 butyl ether, PPG-52 butyl ether, PPG-53 butyl ether. PPG-10 cetyl ether, PPG-28 cetyl ether, PPG-30 cetyl ether, PPG-50 cetyl ether, PPG-30 isocetyl ether, PPG-4 lauryl ether, PPG-7 lauryl ether, PPG-2 methyl ether, PPG-3 methyl ether, PPG-3 myristyl ether, PPG-4 myristyl ether, PPG-10 oleyl ether, PPG-20 olcyl ether, PPG-23 oleyl ether, PPG-30 oleyl ether, PPG-37 oleyl ether, PPG-40 butyl ether, PPG-50 oleyl ether, PPG-11 stearyl ether, herring oil, cod-liver oil, salmon oil, cyclomethicone, a dimethyl polysiloxane, dimethicone, an epoxy-modified silicone oil, a fatty acid-modified silicone oil, a fluoro group-modified silicone oil, a methylphenylpolysiloxane, phenyl trimethicone and a polyether group-modified silicone oil.

In one or more embodiments, the fatty alcohol has at least 12 carbon atoms in its carbon backbone; and wherein said fatty acid has at least 12 carbon atoms in its carbon backbone.

In one or more embodiments, the fatty alcohol and said fatty acid have a melting point of more than about 40° C.

In one or more embodiments, the fatty alcohol is selected from the group consisting of lauryl alcohol, myristyl alcohol, cetyl alcohol, stearyl alcohol, arachidyl alcohol, behenyl alcohol, tetracosanol, hexacosanol, octacosanol, triacontanol, tetratriacontanol; and wherein said fatty acid is selected from the group consisting of dodecanoic acid, tetradecanoic acid, hexadecanoic acid, heptadecanoic acid, octadecanoic acid, eicosanoic acid, docosanoic acid, tetracosanoic acid, hexacosanoic acid, heptacosanoic acid, octacosanoic acid, triacontanoic acid, dotriacontanoic acid, tritriacontanoic acid, tetratriacontanoic acid and pentatriacontanoic acid.

In one or more embodiments, the carbon chain of said fatty alcohol or said fatty acid is substituted with a hydroxyl group, and for example, the carbon chain of said fatty acid is 12-hydroxy stearic acid.

In one or more embodiments, wax is selected from the group consisting of a plant wax, carnauba wax, candelilla wax, ouricury wax, sugarcane wax, retamo wax, jojoba oil, an animal waxes, beeswax, a petroleum derived wax, a paraffin wax, polyethylene and derivatives thereof.

In one or more embodiments, the viscosity-modifying agent is a combination comprising (i) at least one fatty alcohol and at least one fatty acid; or (ii) at least one fatty alcohol and least one wax; or (iii) at least one fatty acid and at least one wax; or (iv) at least one fatty alcohol, at least one fatty acid and least one wax.

In one or more embodiments, the hydrophobic breakable vehicle is substantially free of surface active agents, protic solvents, polar aprotic solvents and silicone thickening agents.

In one or more embodiments, the hydrophobic breakable vehicle is substantially free of surface active agents, polymeric gelling agents, polyols, short chain alcohols and silicone thickening agents.

In one or more embodiments, the hydrophobic breakable vehicle contains less than about 0.4%; or less than about 0.2%; or less than about 0.1% of surface active agents, protic solvents, polar aprotic solvents and silicone thickening agents.

In one or more embodiments, the tetracycline antibiotic is selected from the group consisting of tetracycline, oxytetracycline, demeclocycline, doxycycline, lymecycline, meclocycline, methacycline, minocycline, rolitetracycline, chlorotetracycline and tigecycline, and for example, the tetracycline antibiotic is hydrophobic.

In one or more embodiments, the tetracycline antibiotic is present in a free base form a hydrate form, a salt form or a complex form, and for example, the Log of the distribution constant of the tetracycline antibiotic at pH 7.0 (buffer/chloroform) is equal to or less than about 0.2.

In one or more embodiments, the tetracycline antibiotic does not comprise any hydroxy group at Carbons 5, 6, and 7, and for example, the tetracycline antibiotic is selected from the group of minocycline and doxycycline; or is minocycline.

In one or more embodiments, the composition further comprises an additional active agent.

In one or more embodiments, the additional active agent is selected form the group consisting of an active herbal extract, an acaricides, an age spot and keratose removing agent, an allergen, an alpha hydroxyl acid, an analgesic agent, an androgen, an antiacne agent, an antiallergic agent, an antiaging agent, an antibacterial agent, an antibiotic, an antiburn agent, an anticancer agent, an antidandruff agent, an antidepressant, an antidermatitis agent, an antiedemic anent, an antifungal agent, an antihistamine, an antihelminth agent, an anti-hyperkeratosis agent, an anti-infective agent, an antiinflammatory agent, an antiirritant, an antilipemic agent, an antimicrobial agent, an antimycotic agent, an antioxidant, an antiparasitic agent, an antiproliferative agent, an antipruritic agent, an antipsoriatic agent, an antirosacea agent, an antiseborrheic agent, an antiseptic agent, an antiswelling agent, an antiviral agent, an anti-wart agent, an anti-wrinkle agent, an antiyeast agents, an astringent, a beta-hydroxy acid, benzoyl peroxide, a topical cardiovascular agent, a chemotherapeutic agent, a corticosteroid, an immunogenic substance, a dicarboxylic acid, a disinfectant, an estrogen, a fungicide, a hair growth regulator, a haptene, a hormone, a hydroxy acid, an immunosuppressant, an immunoregulating agent, an immunomodulator, an immunostimulant, an insecticide, an insect repellent, a keratolytic agent, a lactam, a local anesthetic agent, a lubricating agent, a masking agent, a metals, a metal oxide, a mitocide, a neuropeptide, a non-steroidal anti-inflammatory agent, an oxidizing agent, a pediculicide, a peptide, a pesticide, a protein, a photodynamic therapy agent, a progesterone, a radical scavenger, a refatting agent, a retinoid, a sanative, a scabicide, a sedative, a self tanning agent, a skin protective agent, a skin whitening agent, a steroid, a steroid hormone, a vasoactive agent, a vasoconstrictor, a vasodilator, a vitamin, a vitamin A, a vitamin A derivative, a vitamin B, a vitamin B derivative, a vitamin C, a vitamin C derivative, a vitamin D, a vitamin D derivative, a vitamin D analog, a vitamin F, a vitamin F derivative, a vitamin K, a vitamin K derivative, a wound healing agent and a wart remover.

In one or more embodiments, wherein, when tested in the Franz-cell in vitro model using human or pig's skin, affords an amount of the tetracycline in the skin which is higher than the respective amount transferred transdermally.

In one or more embodiments, wherein, when tested in the Franz-cell in vitro model using human or pig's skin, the ratio between the amount of the tetracycline in the skin and the respective amount transferred transdermally is higher than about 100:1; or between about 100:1 and about 10:1; or between about 10:1 and about 2:1; or more than 1:1.

In one or more embodiments, wherein the concentration of the tetracycline in the hydrophobic breakable composition is higher than the lowest concentration which results in intradermal delivery of sufficient concentrations of the tetracycline to have a therapeutic effect when tested in the Franz-cell in vitro model, using human or pig's skin.

In one or more embodiments, wherein the composition prevents the degradation of the tetracycline antibiotic upon application on the target site of treatment.

In another aspect, a method of preventing, treating or alleviating the symptoms of a dermatological, an ophthalmological, a gynecologic or mucosal disorder includes applying topically to the target area a hydrophobic therapeutic composition as described herein.

In one or more embodiments, the disorder includes bacterial infection, inflammation, oxidative stress, and neurodegeneration and/or apoptosis as one of it etiological factors.

In one or more embodiments, the disorder is selected from the group consisting of a dermatological condition abscess, acne, acne conglobata, acne fulminans, acne vulgaris, acne scars, acute febrile neutrophilic dermatosis, acute lymphangitis, allergic contact dermatitis, alopecia, athlete's foot, atopic dermatitis, bacterial skin infections, baldness, basal cell carcinoma, blisters, bromhidrosis, bullous pemphigoid, burn, calluses candidiasis, carbuncles, cellulitis, chemical burns, chicken pox, cholesteatoma, cholinergic urticaria, chronic effects of sunlight, cold sores, cold urticaria, comedones, corns, creeping eruption, cutaneous abscess, cutaneous larva migrans, cutaneous myiasis, dark spots, delusional parasitosis, Dercum disease, dermatitis, dermatitis herpetiformis, dermatological pain, dermatological inflammation, dermographism, dermatophytoses, drug eruptions and reactions, dyshidrotic eczema, ectodermal dysplasia, eczema, ecthyma, epidermoid cyst, epidermal necrolysis, erysipelas, erysipelas, erythrasma, exfoliative dermatitis, erythema multiforme, erythema nodosum, folliculitis, fungal nail infections, fungal skin infections, furuncles, gangrene, genital herpes, granuloma annularc, head lice, hidradenitis suppurativa, hives, folliculitis, hirsutism, hyperhidrosis, hypohidrosis, ichthyosis, impetigo, inflammatory acne, ingrown nails, intertrigo, irritant contact dermatitis, ischemic necrosis, itching, jock itch, Kaposi's sarcoma, keratosis pilaris, lichen simplex chronicus, lichen planus, lichen sclerosus, lymphadenitis, lymphadenitis, lymphangitis, malignant melanoma, mastocytosis, measles, melanoma, melanoma, miliaria, moles, molluscum contagiosum, MRSA, necrotizing subcutaneous infection, necrotizing fasciitis, necrotizing myositis, nodular papulopustular acne, non-inflammatory acne, nummular dermatitis, oral herpes, panniculitis, parapsoriasis paronychia, parasitic skin infections, pemphigus, photo-allergy, photo-damage, photo-irritation, photosensitivity, papules, pediculosis, perioral dermatitis, pimples, *pityriasis rosea, pityriasis* Lichenoides, *pityriasis rosea, pityriasis rubra* pilaris, poison ivy, post-operative or post-surgical skin conditions, pressure ulcers, pressure urticaria, pruritis, pseudofolliculitis barbae, psoriasis, PUPPP, purpura, pustules, pyogenic granuloma, rash, ringworm, rosacea, roseola, rubella, scabies, scalded skin syndrome, scarring, scleroderma, sebaceous cyst, seborrheic dermatitis, seborrheic keratosis, shingles, skin aging, skin cancer, skin neoplasia, skin neoplasms, skin rash, skin ulcers, squamous cell carcinoma, staphylococcal scalded skin syndrome, stasis dermatitis, Stevens-Johnson syndrome, sunburn, sun spots, thermal burns, *tinea corporis, tinea cruris, tinea pedis, tinea versicolor*, toxic epidermal necrolysis, trauma or injury to the skin, varicella zoster virus, vitamin D deficiency, viral skin infections, vitiligo. warts, water hives, wrinkles, xerosis, yeast skin infections and zoster; a disorder of a body cavity or mucosal surface, a disorder of the nose, mouth, eye, ear, respiratory system, vagina, urethra, or rectum, *chlamydia* infection, gonorrhea infection, hepatitis B, herpes, HIV/AIDS, human papillomavirus (HPV), genital warts, bacterial vaginosis, candidiasis, chancroid, granuloma Inguinale, lymphogranloma venereum, mucopurulent cervicitis (MPC), molluscum contagiosum, nongonococcal urethritis (NGU), trichomoniasis, vulvar disorders, vulvodynia, vulvar pain, yeast infection, vulvar dystrophy, vulvar intraepithelial neoplasia (VIN), contact dermatitis, pelvic inflammation, endometritis, salpingitis, oophoritis, genital cancer, cancer of the cervix, cancer of the vulva, cancer of the vagina, vaginal dryness, dyspareunia, anal and rectal disease, anal abscess/fistula, anal cancer, anal fissure, anal warts, Crohn's disease, hemorrhoids, anal itch, pruritus ani, fecal incontinence, constipation, polyps of the colon and rectum; an ophthalmic disorder, eye redness, eye pain or light sensitivity, blurred vision, loss of vision, visual disturbances—floaters, flashing, distortion, halos, etc., itching/burning, tearing/discharge, sensation of something in the eye, eyelid problems, double vision; ophtahlmic allergy, blepharitis, cataract, central scrous chorioretinopathy, color vision problems, corneal abrasion, corneal edema, corneal ulcer, conjunctivitis, contact lens complications, dacryocystitis, blurred distance vision, dry eye, eale's disease, episcleritis, eyelid ectropion, eyelid entropion, eyelid cellulitis, eye strain, focusing spasm, glaucoma, acute glaucoma, iritis, keratoconus, lyme disease, macular degeneration, macular edema, macular hole, eye medication toxicity, myasthenia gravis, ocular cicatricial pemphigoid, ophthalmic migraine, presbyopia, obstructed tear duct, optic neuritis, optic nerve stroke, orbital fracture, orbital cellulitis, phlyetenulosis, pterygium, recurrent corneal erosion, retinal artery occlusion, retinal detachment, retinal tear, retinal vein occlusion, sarcoidosis, scleritis, sinus disease, strabismus (ocular misalignment), subconjunctival hemorrhage, temporal arteritis, thyroid eye disease, trichiasis, eyelid tumor, twitching of eyelid (eyelid myokymia), uveitis, vitreous detachment and vitreous hemorrhage.

In one or more embodiments, the disorder is selected from the group consisting of a skin infection, acne, rosacea, an eye infection, ocular rosacea, blepharitis, dry eye, trachoma and glaucoma.

In one or more other specific embodiments the drug carrier is formulated substantially free of elastomers. In one or more other specific embodiments the drug carrier is formulated essentially free of elastomers. In one or more other specific embodiments the drug carrier is formulated substantially free of silicones. In one or more other specific embodiments the drug carrier is formulated essentially free of silicones. In one or more other specific embodiments the drug carrier is formulated with less than about 30% silicone, or less than about 25% silicone, or less than about 20% silicone, or less than about 15% silicone, or less than about 10% silicone, or less than about 7.5% silicone, or less than about 5% silicone or less than about 2% silicone; or less than about 1% silicone; or less than about 0.5% silicone.

DETAILED DESCRIPTION

The present invention is directed to a hydrophobic breakable tetracycline formulation for topical administration, wherein the formulation is (i) in the form of an oil gel that liquefies and spreads easily upon application of mild shear force; or (ii) an oil foam; wherein said oil foam is stable upon dispensing from the aerosol can and breaks down and spreads easily upon application of mild shear force.

The formulation of the invention is suitable for topical administration to the skin and mucosal membranes, the eyes, nasal cavity, the ear canal and the vaginal cavity.

A feature of a product for medical use is long term stability. The compositions herein are surprisingly stable. Following accelerated stability studies, they demonstrate desirable texture, do not break immediately upon contact with a surface, spread easily on the treated area and absorb quickly.

In one or more embodiments the composition has an acceptable shelf-life of at least six months. In one or more embodiments the foam composition has an acceptable shelf-life of at least one year, In one or more embodiments the foam composition has an acceptable shelf-life of at least 15 months, or at least 18 months or at least 21 months or at least two years at ambient temperature.

In one or embodiments stability is inter alia a product of extensive effort and research; eliminating surfactants; eliminating water; choice of components; testing each component individually with the active agent (compatibility studies); the combination of components, having an appropriate Aw value (e.g. <9), storage in an air and light tight container.

In one or more embodiments the active agent is considered chemically stable when more than about 90% of the active agent does not break down after a period of two months in the formulation at room temperature. In one or more embodiments the period is six months. In one or more embodiments more than about 88% of the active agent does not break down. In one or more embodiments the active agent is chemically stable in the composition at 40° C.

In one or more embodiments the drug carrier is formulated substantially free of short chain alcohols, such as, ethanol, propanol or butanol. In one or more embodiments the drug carrier is formulated essentially free of short chain alcohols. In one or more specific embodiments the drug carrier is formulated essentially free of derivatives of fatty alcohols or fatty acids. In one or more other specific embodiments the drug carrier is formulated essentially free of polyols. In one or more other specific embodiments the drug carrier is formulated substantially free of surfactants and or short chain alcohols and or polyols. In one or more other specific embodiments the drug carrier is formulated essentially free of surfactants and or short chain alcohols and or polyols. In one or more embodiments there is provided a composition which is essentially waterless. In one or more embodiments there is provided a surfactant free composition that is also free of short chain alcohols and or polyol-free. In one or more embodiments there is provided a substantially polymer free composition. In other embodiments it is essentially polymer free. In still further embodiments the composition is free of polymeric agent. In one or more embodiments a polymeric agent has a Molecular weight of at least about 1000 Daltons.

In one or more embodiments the composition is essentially free of two or more of water; polymeric agent; surfactant; short chain alcohol; or polyol. In one or more embodiments the composition is essentially free of three or more of water; polymeric agent; surfactant; short chain alcohol; or polyol. In one or more embodiments the composition is essentially free of four or more of water; polymeric agent; surfactant; short chain alcohol; or polyol. In one or more embodiments the composition is essentially free of water, polymeric agent; surfactant; short chain alcohol; and polyol.

In one or more other specific embodiments the drug carrier is formulated substantially free of elastomers. In one or more other specific embodiments the drug carrier is formulated essentially free of elastomers. In one or more other specific embodiments the drug carrier is formulated substantially free of silicones. In one or more other specific embodiments the drug carrier is formulated essentially free of silicones. In one or more other specific embodiments the drug carrier is formulated with less than about 30% silicone, or less than about 25% silicone, or less than about 20% silicone, or less than about 15% silicone, or less than about 10% silicone, or less than about 7.5% silicone, or less than about 5% silicone or less than about 2% silicone; or less than about 1% silicone; or less than about 0.5% silicone.

Definitions

All % values are provided on a weight (w/w) basis.

In one or more embodiments wherever a phrase is used to refer to a concentration of above X % or below X % it can also include X % or above about X % or below about X % it can also include about X %.

In one or more embodiments the term "about" has its usual meaning in the context of pharmaceutical and cosmetic formulations to allow for reasonable variations in amounts that can achieve the same effect. By the term "about" herein it is meant as indicated above and also that a figure or range of figures can vary in an embodiments plus or minus up to 30%. So in this embodiment if a figure of "about 1" is provided then the amount can be up to 1.3 or from 0.70. In other embodiments it can reflect a variation of plus or minus 20%. In still further embodiments it can describe a variation of plus or minus 10%. In still further embodiments it can describe a variation of plus or minus 5%. As will be appreciated by one of the art there is some reasonable flexibility in formulating compositions such that where one or more ingredients are varied successful formulations may still be made even if an amount falls slightly outside the range. Therefore, to allow for this possibility amounts are qualified by about. In one or more other embodiments the figures may be read without the prefix about.

The term "thixotropic," as used herein, means that the formulation shows a significant decrease in viscosity upon application of shear force.

The term "waterless," as used herein, means that the composition contains no, or substantially no, free or unassociated or absorbed water. Similarly, "waterless" or "substantially waterless" carriers contain at most incidental and trace amounts of water.

By the term "single phase" herein it is meant that the liquid components of the composition or carrier are fully miscible, and the solid components if any, are either dissolved or suspended in the composition. By substantially a single phase is meant that the composition or carrier is primarily or essentially a single phase as explained above, but may also have present a small amount of material which is capable of forming or may form a separate phase amounting to less than about 5% of the composition or carrier, preferably less than about 3%, and more preferably less than about 1%. By the term "single phase" or "substantially a single phase" in the context of a foamable composition the above meaning applies even after addition of propellant to the composition or carrier.

The term "unstable active agent" as used herein, means an active agent which is oxidized and/or degraded within less than a day, and in some cases, in less than an hour upon exposure to air, light, skin or water under ambient conditions.

The term "co-surfactant" as used herein, means a compound which on its own is not able to form and stabilize satisfactorily an oil in water emulsion, but when used in combination with a surfactant, such co-surfactant can boost the emulsifying power of surfactants to create a stable emulsion. For example, fatty alcohols, such as cetyl alcohol or a fatty acid such as stearic acid can function as co-surfactants. Cetyl alcohol and stearyl alcohol are waxy hydrophobic substances that can be emulsified with water using a surfactant. In certain circumstances a co-surfactant can itself be converted in to a surfactant or soap by, for example, adding a base, such as, triethanolamine to a fatty acid, resulting in a fatty acid salt, which is also termed "soap" (a strong anionic surfactant).

The identification of a "polyol", as used herein, is an organic substance that contains at least two hydroxy groups in its molecular structure.

Gel and Foam Presentations

The topical therapeutic hydrophobic breakable composition of the present invention can be presented as a gel or as a foam. The term "breakable", as used herein relates to a composition is stable as a gel or as a foam upon dispensing from a container, yet breaks and spreads easily upon application of mild shear force.

It was surprisingly discovered in the present invention, that certain compositions comprising a hydrophobic solvent, together with viscosity-modifying agents which may be at least one fatty alcohol and/or at least one fatty acid, and/or at least one wax and mixtures of two or more thereof; and a suspended active agent; without any surface active agents afford, upon packaging in an aerosol container and adding a propellant, a shakable and homogenous foamable composition, which releases a breakable foam with good to excellent quality (as defined herein.

The resulting foam is pharmaceutically equivalent to the respective gel (prior to adding the propellant), since immediately upon dispensing of the foam the propellant evaporates and the composition upon administration is similar to that of the gel. This is an important pragmatic advantage, because many drug development activities, including expensive and lengthy toxicology studies with numerous animals and clinical trials with thousands of patients can be saved by conducting such studies once for the gel and foam presentation instead of twice (for each presentation).

Gel

The primary essential components the gel of the present invention comprises (a) at least one hydrophobic oil, (b) at least one viscosity-modifying agent and (c) a tetracycline antibiotic. The concentration of the hydrophobic oil is between about 60% and about 99% by weight. In one or more other embodiments the concentration is between about 60% and about 95%, or is between about 65% and about 99%, or is between about 65% and about 95%, or is between about 70% and about 95%, or is between about 75% and about 95%, or is between about 80% and about 95%, or is between about 85% and about 99%, or is between about 85% and about 95%.

Surprisingly, we discovered that, while the addition of the viscosity-modifying agents to the hydrophobic oil increased the viscosity of such oil, even small amounts of a suspended tetracycline antibiotic increased the viscosity of the composition synergistically. The gel is stable and it retains its viscosity upon dispensing from a container, such as a tube, yet, it liquefies and spreads easily upon application of mild shear force. Further, whilst the gel is oily, it readily absorbs into the site of application such as the skin, and after a few minutes the surface looks and feels free of any oiliness or greasiness.

The combination of a tetracycline with a mixture of one or more hydrophobic oils, fatty alcohols, fatty acids and waxes has a strong synergistic effect and increases the formulation viscosity. For example, the viscosity of a formulation containing 0.50% minocycline HCl is about three times higher than the viscosity of the same formulation without the tetracycline. The effect on the formulation viscosity is directly related to the concentration of the tetracycline: the higher the tetracycline concentration, the higher the viscosity of the formulation. In certain cases, it appeared that the viscosity increasing effect of minocycline HCl reaches a plateau when the active ingredient is present at a concentration of about 0.50% or, in certain embodiments, when the viscosity of the carrier is in excess of about 25,000 cps.

Thus, in one or more embodiments, there is provided a gel containing at least one hydrophobic oil and a tetracycline in a synergistic combination with a fatty alcohol, and/or a fatty acid and/or a wax, wherein the viscosity of the formulation is increased by the addition of the active ingredient by more than about 30%, or more than about 50%, or more than about 100%, or more than about 200%, or more than about 300%, or more than about 500%.

In one or more embodiments, the increase in the formulation viscosity is correlated with the concentration of the active agent.

In one or more embodiments, the viscosity of the formulation is directly proportional to the concentration of the active agent: the higher the concentration of the active ingredient, the higher the formulation viscosity.

In one or more embodiments, the viscosity increasing effect of the active ingredient reaches a plateau when the concentration of the active ingredient is increased.

In one or more embodiments, the viscosity of the formulation containing the tetracycline is twice the viscosity of the sample formulation when the active ingredient is present at a concentration of less than about 10%, less than about 5%, less than about 1%, less than about 0.5%, less than about 0.1%, less than about 0.05%, less than about 0.01%.

In one or more embodiments the viscosity of the gel is higher than about 10000 cPs; or between about 1000 cPs and about 100000 cPs; or between about 5000 cPs and about 50000 cPs; or between about 10000 cPs and about 30000 cPs.

In one or more embodiments the increase in viscosity of the composition is at least about 100% and viscosity of the carrier is less than about 12,000 cPs; or less than about 8,000 cPs; or less than about 2,000 cPs. In one or more embodiments the viscosity of the carrier is more than about 1,000 cPs; or more than about 1,300 cPs; or more than about 1,500 cPs. or more than about 1,800 cPs or more than about 2000 cPs. In one or more embodiments the viscosity of the carrier is more than about 150 cPs; or more than about 300 cPs, or more than about 500 cPs or more than about 800 cPs.

In one or more embodiments the change in viscosity is between about 50% and about 100%. In one or more embodiments the change in viscosity is between about 100% and about 500%. In one or more embodiments the change in viscosity is between about 500% and about 1000%. In one or more embodiments the change in viscosity is between about 1000% and about 1500%. In one or more embodiments the change in viscosity is between about 1500% and about 2000%. In one or more embodiments the change in viscosity is between about 2000% and about 2500%. In one or more embodiments the change in viscosity is between about 50% and about 3000%. In one or more embodiments the change in viscosity is in a range between about 150% and about 1000%. In one or more embodiments the change in viscosity is in a range between about 1000% and about 2500% In one or more embodiments the change in viscosity is between about 100% and about 2500%; about 100% and about 2000%; about 100% and about 1500%; or about 100% and about 1000%.

The gel composition has the unique property of stabilizing the tetracycline antibiotic and protecting it from degradation. For example, when a gel, containing about 83% hydrophobic oils, about 4.5% waxes, about 6% fatty alcohols and 5% fatty acid and about 1% micronized minocycline HCl was applied to freshly retrieved and moist skin and stored on a Petri dish, with exposure to air and light for 6 hours the product remained substantially stable. Furthermore, even when a specimen of a hydrophobic gel with 1% minocycline was applied to a skin and exposed to direct sun light for two days, there was no apparent degradation, as shown by the conservation of the skin color. As tetracycline antibiotics, and especially minocycline are know to be susceptible to degradation by air, water and light, this protection effect is unique.

In an additional observation, while the minocycline was protected from the environmental factors (moisture light and air), it is not hindered or tightly encapsulated, as demonstrated by its efficient release into the skin in an in-vitro Franz cell model, an antibacterial test model and an anti-inflammation model, as further exemplified herein.

Foam

One skilled in the art would expect that a surfactant should be required in order to facilitate the production of foam.

However, surprisingly, when the gel composition described above, comprising (a) at least one hydrophobic oil, (b) at least one viscosity-modifying agent, and (c) a tetracycline antibiotic is introduced into an aerosol can, closed with an aerosol valve and pressurized with a propellant, it creates a breakable foam, i.e., a foam which is stable upon dispensing from a container, yet breaks and spreads easily upon application of mild shear force. As in the case of the gel, the foam it readily absorbs into the site of application such as the skin, and after a few minutes the surface looks and feels free of any oiliness or greasiness.

Foaming Propellant

Examples of suitable propellants include compressed gases, volatile hydrocarbons such as butane, propane, isobutane and fluorocarbon gases, or mixtures thereof.

In an embodiment, the propellant is hydrophobic and it miscible with the oils in the composition.

In certain embodiments, fluoro-hydrocarbon propellants, other than chloro-fluoro carbons (CFCs) which are non-ozone-depleting propellants, are particularly useful in the production of a non-flammable foamable composition.

Such propellants include, but are not limited to hydrofluorocarbon (HFC) propellants, that contain no chlorine atoms, and as such, falls completely outside concerns about stratospheric ozone destruction by chlorofluorocarbons or other chlorinated hydrocarbons. Exemplary non-flammable propellants according to this aspect of the invention include propellants made by DuPont under the registered trademark Dymel, such as 1,1,1,2 tetrafluorethane (Dymel 134), and 1,1,1,2,3,3,3 heptafluoropropane (Dymel 227), 1,1, difluoro ethane (Dymel 152) and 1,1,1,3,3,3 hexafluoropropane. HFCs possess Ozone Depletion Potential of 0.00 and thus, they are allowed for use as propellant in aerosol products.

Yet, in additional embodiments, the propellant is a self-foaming propellant, i.e., a volatile liquid having a boiling point of less than the temperature of the target treatment site (such as the skin). An example of a post-foaming propellant is isopentane (bp=26° C.)

In an embodiment, the ratio of composition other than propellant to propellant is between about 100:1 to about 100:25, or is between about 100:3 to about 100:30, or is between about 100:5 to about 100:20 or is between about 100:8 to about 100:16, or between about 100:20 and about 100:50.

In one or more embodiments a foam formulation can be expelled or helped to be expelled by using propellant which is separate from the formulation using, for example, a bag on valve (BOV) or can in can aerosol system. A BOV system consists of the aerosol valve with a welded bag. With the BOV system compressed air or other propellants are introduced in the aerosol can on the outside of the bag and acts as a propellant on the product which is inside the bag. Using such a system makes it possible to reduce the amount of propellant within the formulation but still enable expulsion from the canister of a foam with desirable qualities. So by way of example, the concentration of the propellant in the bag is between about 1% to 3%; or between about 2% to 4%; between about 3% to 5% (ratio of formulation to propellant of 100:1 to 100:3; 100:2 to 100:4; 100:3 to 5; respectively.

Foam Properties

A foamable composition manufactured according to one or more embodiments herein is very easy to use. When applied onto the afflicted body surface of mammals, i.e., humans or animals, it is in a foam state, allowing free application without spillage. Upon further application of a mechanical force, e.g., by rubbing the composition onto the body surface, it freely spreads on the surface and is rapidly absorbed.

In one or more embodiments the foamable composition is a single phase solution. In one or more embodiments the foamable composition is substantially a single phase solution. In certain circumstances, where the active agent is insoluble and is presented as a homogenous suspension, the formulation is turbid or cloudy.

In one or more embodiments the foam composition has an acceptable shelf-life of at least one year, or at least two years at ambient temperature. A feature of a product for cosmetic or medical use is long term stability. Propellants, which are a mixture of low molecular weight hydrocarbons, or HFCs, tend to impair the stability. The foamable compositions herein are surprisingly stable, even in the absence of surfactants. Following accelerated stability studies, they demonstrate desirable texture; they form fine bubble structures that do not break immediately upon contact with a surface. They spread easily on the treated area and absorb quickly.

The composition should also be free flowing, to allow it to flow through the aperture of the container, e.g., and aerosol container, and create an acceptable foam. Compositions containing a substantial amount of semi-solid hydrophobic oils, e.g., white petrolatum, as the main ingredients of the oil phase of the emulsion, will likely exhibit high viscosity and poor flowability and can be inappropriate candidates for a foamable composition. Thus in one or more embodiments semi-solid hydrophobic oils are a subsidiary component in the composition, for example being present at less than about 25%, less than about 20%, less than about 15%, less than about 10%, or less than about 5% by weight of the foamable composition. In other embodiments they can be present in higher amounts due to the solvent effect of the propellant diluting the formulation and enabling flowability or where the formulation is presented as a gel or ointment or when solvents are added that reduce the viscosity such as alkyl benzoates.

Foam Quality

Foam quality can be graded as follows:

Grade E (excellent): very rich and creamy in appearance, does not show any bubble structure or shows a very fine (small) bubble structure; does not rapidly become dull; upon spreading on the skin, the foam retains the creaminess property and does not appear watery.

Grade G (good): rich and creamy in appearance, very small bubble size, "dulls" more rapidly than an excellent foam, retains creaminess upon spreading on the skin, and does not become watery.

Grade FG (fairly good): a moderate amount of creaminess noticeable, bubble structure is noticeable; upon spreading on the skin the product dulls rapidly and becomes somewhat lower in apparent viscosity.

Grade F (fair): very little creaminess noticeable, larger bubble structure than a "fairly good" foam, upon spreading on the skin it becomes thin in appearance and watery.

Grade P (poor): no creaminess noticeable, large bubble structure, and when spread on the skin it becomes very thin and watery in appearance.

Grade VP (very poor): dry foam, large very dull bubbles, difficult to spread on the skin.

Topically administrable foams are typically of quality grade E or G, when released from the aerosol container. Smaller bubbles are indicative of a more stable foam, which does not collapse spontaneously immediately upon discharge from the container. The finer foam structure looks and feels smoother, thus increasing its usability and appeal.

Foam Density

Another property of the foam is specific gravity or density, as measured upon release from the aerosol can. Typically, foams have specific gravity of less than 0.5 g/mL; or less than 0.3 g/mL; or less than 0.2 g/mL; or less than 0.1 g/mL, depending on their composition and on the propellant concentration. In one or more embodiments the foam density is about less than 0.3 g/mL.

Shakability

'Shakability' means that the composition contains some or sufficient flow to allow the composition to be mixed or remixed on shaking. That is, it has fluid or semi fluid properties. Shakability is described further in the section on Tests. In one or more certain limited embodiments the formulation is poorly shakable but is nevertheless flowable.

Breakability/Collapse Time

A further aspect of the foam is breakability. The balance between stability and breakability of the foam coming out of the container is very delicate: on one hand the foam should preferably not be "quick breaking", i.e., it should be stable upon release from the pressurized container and not break as a result of exposure to skin temperature; and on the other hand, it should be "breakable", i.e., it should spread easily, break down and absorb into the skin or membrane upon application of mild shear force. The breakable foam is thermally stable, yet breaks under shear force. Shear-force breakability of the foam is clearly advantageous over thermally-induced breakability. Thermally sensitive foams can start to collapse immediately upon exposure to skin temperature and, therefore, cannot be applied on the hand and afterwards delivered to the afflicted area.

The collapse time of foam represents its tendency to be temperature-sensitive and its ability to be at least stable in the short term so as to allow a user sufficient time to comfortably handle and apply the foam to a target area without being rushed and or concerned that it may rapidly collapse, liquefy and or disappear. Collapse time, as an indicator of thermal sensitivity, is examined by dispensing a given quantity of foam and photographing sequentially its appearance with time during incubation at 36° C. Simple collapse time can be measured by applying a foam sample on a body surface like the fingers at normal body temperature of about 37° C.

Oils may cause foam to be thermolabile and "quick breaking." However, in certain embodiments herein, despite the presence of high oil content, quite unexpectedly the foam is substantially thermally stable. By "substantially thermally stable" it is meant that the foam upon application onto a warm skin or body surface at about 35-37° C. does not collapse within about 30 seconds. Thus, in one or more embodiments the simple collapse time of the foam is more than about 30 seconds or more than about one minute or more than about two minutes. In one or more limited embodiments simple collapse time can be a little shorter than 30 seconds, but not less than about 20 seconds. In one or further or alternative embodiments the collapse time is measured by introducing a sample of foam into an incubator at 36° C. and the collapse time of the foam is more than 30 seconds or more than about one minute or more than about two minutes.

Water Activity

The term "water activity" as used herein, activity represents the hydroscopic nature of a substance; or the tendency of a substance that absorbs water from its surroundings. Microorganisms require water to grow and reproduce, and such water requirements are best defined in terms of water activity of the substrate. The water activity of a solution is expressed as Aw=P/Po, where P is the water vapor pressure of the solution and Po is the vapor pressure of pure water at the same temperature. Every microorganism has a limiting Aw, below which it will not grow; e.g., for *Streptococci, Klebsiella* spp, *Escherichia coli, Clostridium perfringens*, and *Pseudomonas* spp, the Aw value is 0.95. *Staphylococcus aureus* is most resistant and can proliferate with an Aw as low as 0.86, and fungi can survive at Aw of at least 0.7. In one or more embodiments, the concentration of the hydrophobic oil in the gel or foam composition is sufficient to provide an Aw value selected from the ranges of (1) about 0.8 and about 0.9; (2) about 0.7 and about 0.8; and (3) less than about 0.7. By delivering the formulation in a pressurized package does not allow for humidity to be absorbed by the preparation, and therefore, the water free character of the composition cannot be damaged.

Tetracycline

The primary active agent in accordance with the present invention is a tetracycline compound (herein "a tetracycline" or "tetracyclines") or a pharmaceutically acceptable salt or hydrate thereof substantially stabilized in a base. The tetracyclines are characterized by a carbon skeleton composed of four linearly fused six-membered carbon rings (octahydrotetracene-2-carboxamide Skeleton). They are defined as "a subclass of polyketides having an octahydrotetracene-2-carboxamide skeleton". They are collectively known as "derivatives of polycyclic naphthacene carboxamide".

Non-limiting examples of tetracyclines, include the naturally-occurring Tetracycline, Chlortetracycline, Oxytetracycline and Demeclocycline, the semi-synthetic Doxycycline, Lymecycline, Meclocycline, Methacycline, Minocycline, Rolitetracycline, Chlorotetracycline and Tigecycline.

The tetracyclines can be present in a free base form a hydrate form, a salt form or a complex form. For example, minocycline can be present as the base form, as well as a hydrate or a hydrochloride salt.

Notably, various tetracyclines have different hydrophilic/hydrophobic characters. For example, the Log Kp (log of the of distribution constant at pH 7.0; buffer/CHCl$_3$) is 1.91, which means that it is highly hydrophilic. The Log Kp of Doxycycline is 0.2; and the Log Kp of Minocycline is −1.6, which stands for hydrophobic character of this compound (see Leive L et al, "Tetracyclines of various hydrophobicities as a probe for permeability of *Escherichia coli* outer membrane", Antimicrobial Agents and Chemotherapy 1984: 25, 539-544). Whilst any tetracycline compound is suitable as an active agent according to the present invention, there is preference to tetracycline compounds which are more hydrophobic. Thus, in an embodiment of the present invention the active agent is selected as one that has Log Kp equal to, or lower than about 0.2.

In an embodiment, the tetracycline antibiotic is hydrophobic due to the fact that it does not comprise any hydroxy group at Carbons 5, 6, and 7.

In certain embodiments, the tetracycline is selected from the group consisting of doxycycline and minocycline; and in a certain embodiment the tetracycline is minocycline.

According to the present invention, the tetracycline is employed in an amount ranging from about 0.001% to about 10%; or in an amount ranging from about 0.025% to about 6%; or in an amount ranging from about 0.1% to about 3%, by weight of the foamable composition.

The tetracycline in accordance to the present invention is insoluble or is partially soluble in the whole composition and all or part thereof is suspended. It is known that every chemical compound has different solubility in different solvents or compositions, and therefore it is not possible to provide a general list compounds that are not soluble or partially soluble or suspended in the composition. However, any tetracycline active agent, as exemplified herein, is suitable as insoluble or partially soluble or suspended, if visual or microscopic observation demonstrates crystals or particles of such active agent in the oleaginous composition.

In additional embodiments, the concentration of the tetracycline is determined by its ability to inhibit the occurrence of apoptosis in an ex-vivo human skin model; or by its ability to inhibit the occurrence of pro-inflammatory cytokines in an ex-vivo human skin model. In alternate embodiments, the concentration of the tetracycline is higher than the lowest concentration which results in intradermal delivery of sufficient concentrations of the tetracycline when tested in the Franz-cell in vitro model, using human or pig's skin.

Hydrophobic Oil

The term "hydrophobic oil" relates to a material, having solubility in distilled water at ambient temperature of less than about 1 gm per 100 mL, or less than about 0.5 gm per 100 mL, or less than about 0.1 gm per 100 mL. The hydrophobic oil is a liquid at ambient (room) temperature, e.g., about 20-30° C.

In an embodiment, the topical therapeutic composition comprises at least one hydrophobic oil, selected from the group consisting of a mineral oil, a hydrocarbon oil, an ester oil, a triglyceride oil, an oil of plant origin, an oil from animal origin, an unsaturated or polyunsaturated oil, a diglyceride, a PPG alkyl ether and a silicone oil.

As exemplified herein, members of each of the above listed groups of hydrophobic oils have been found to be compatible with hydrophobic tetracyclines, such as minocycline and doxycycline.

Non-limiting examples of hydrocarbon oils include mineral oil, liquid paraffin, an isoparaffin, a polyalphaolefin, a polyolefin, polyisobutylene, a synthetic isoalkane, isohexadecane and isododecane.

Non-limiting examples of ester oils include alkyl benzoate, alkyl octanoate, C12-C15 alkyl benzoate, C12-C15 alkyl octanoate, arachidyl behenate, arachidyl propionate, benzyl laurate, benzyl myristate, benzyl palmitate, bis (octyldodecyl stearoyl) dimer dilinoleate, butyl myristate, butyl stearate, cetearyl ethylhexanoate, cetearyl isononanoate, cetyl acetate, cetyl ethylhexanoate, cetyl lactate, cetyl myristate, cetyl octanoate, cetyl palmitate, cetyl ricinoleate, decyl oleate, diethyleneglycol diethylhexanoate, diethyleneglycol dioctanoate, diethyleneglycol diisononanoate, diethyleneglycol diisononanoate, diethylhexanoate, diethylhexyl adipate, diethylhexyl malate, diethylhexyl succinate, diisopropyl adipate, diisopropyl dimerate, diisopropyl sebacate, diisostearyl dimer dilinoleate, diisostearyl fumerate, dioctyl malate, dioctyl sebacate, dodecyl oleate, ethylhexyl palmitate, ester derivatives of lanolic acid, ethylhexyl cocoate, ethylhexyl ethylhexanoate, ethylhexyl hydroxystearate, ethylhexyl isononanoate, ethylhexyl palmytate, ethylhexyl pelargonate, ethylhexyl stearate, hexadecyl stearate, hexyl laurate, isoamyl laurate, isocetyl isocetyl behenate, isocetyl lanolate, isocetyl palmitate, isocetyl stearate, isocetyl salicylate, isocetyl stearate, isocetyl stearoyl stearate, isocetearyl octanoate, isodecyl ethylhexanoate, isodecyl isononanoate, isodecyl oleate, isononyl isononanoate, isodecyl oleate, isohexyl decanoate, isononyl octanoate, isopropyl isostearate, isopropyl lanolate, isopropyl laurate, isopropyl myristate, isopropyl palmitate, isopropyl stearate, isostearyl behenate, isostearyl citrate, isostearyl erucate, isostearyl glycolate, isostearyl isononanoate, isostearyl isostearate, isostearyl lactate, isostearyl linoleate, isostearyl linolenate, isostearyl malate, isostearyl neopentanoate, isostearyl palmitate, isostearyl salicylate, isostearyl tartarate, isotridecyl isononanoate, isotridecyl isononanoate, lauryl lactate, myristyl lactate, myristyl myristate, myristyl neopentanoate, myristyl propionate, octyldodecyl myristate, neopentylglycol dicaprate, octyl dodecanol, octyl stearate, octyl palmitate, octyldodecyl behenate, octyldodecyl hydroxystearate, octyldodecyl myristate, octyldodecyl stearoyl stearate, oleyl erucate, oleyl lactate, oleyl oleate, propyl myristate, propylene glycol myristyl ether acetate, propylene glycol dicaprate, propylene glycol dicaprylate, propylene glycol dicaprylate, maleated soybean oil, stearyl caprate, stearyl heptanoate, stearyl propionate, tocopheryl acetate, tocopheryl linoleate, glyceryl oleate, tridecyl ethylhexanoate, tridecyl isononanoate and triisocetyl citrate.

Non-limiting examples of triglycerides and oils of plant origin include alexandria laurel tree oil, avocado oil, apricot stone oil, barley oil, borage seed oil, calendula oil, canelle nut tree oil, canola oil, caprylic/capric triglyceride castor oil, coconut oil, corn oil, cotton oil, cottonseed oil, evening primrose oil, flaxseed oil, groundnut oil, hazelnut oil, glycereth triacetate, glycerol triheptanoate, glyceryl trioctanoate, glyceryl triundecanoate, hempseed oil, jojoba oil, lucerne oil, maize germ oil, marrow oil, millet oil, neopentylglycol dicaprylate/dicaprate, olive oil, palm oil, passionflower oil, pentaerythrityl tetrastearate, poppy oil, propylene glycol ricinoleate, rapeseed oil, rye oil, safflower oil, sesame oil, shea butter, soya oil, soybean oil, sweet almond oil, sunflower oil, sysymbrium oil, syzigium aromaticum oil, tea tree oil, walnut oil, wheat germ glycerides and wheat germ oil.

Non-limiting examples of PPG alkyl ethers include PPG-2 butyl ether, PPG-4 butyl ether, PPG-5 butyl ether, PPG-9 butyl ether, PPG-12 butyl ether, PPG-14 butyl ether, PPG-15 butyl ether, PPG-15 stearyl ether, PPG-16 butyl ether, PPG-17 butyl ether, PPG-18 butyl ether, PPG-20 butyl ether, PPG-22 butyl ether, PPG-24 butyl ether, PPG-26 butyl ether, PPG-30 butyl ether, PPG-33 butyl ether, PPG-40 butyl ether, PPG-52 butyl ether, PPG-53 butyl ether, PPG-10 cetyl ether, PPG-28 cetyl ether, PPG-30 cetyl ether, PPG-50 cetyl ether, PPG-30 isocetyl ether, PPG-4 lauryl ether, PPG-7 lauryl ether, PPG-2 methyl ether, PPG-3 methyl ether, PPG-3 myristyl ether, PPG-4 myristyl ether, PPG-10 oleyl ether, PPG-20 oleyl ether, PPG-23 oleyl ether, PPG-30 oleyl ether, PPG-37 oleyl ether, PPG-40 butyl ether, PPG-50 oleyl ether and PPG-11 stearyl ether. Preferred PPG alky ethers according to the present invention include PPG-15 stearyl ether, PPG-2 butyl ether and PPG-9-13 butyl ether.

Non-limiting examples of oils from animal origin include herring oil, cod-liver oil and salmon oil.

Non-limiting examples of silicone oils include cyclomethicone, a dimethyl polysiloxane, dimethicone, an epoxy-modified silicone oil, a fatty acid-modified silicone oil, a fluoro group-modified silicone oil, a methylphenylpolysiloxane, phenyl trimethicone and a polyether group-modified silicone oil.

Viscosity-Modifying Agent

A viscosity-modifying agent, in the context of the present invention is an agent which, when added to a hydrophobic oil, facilitates the creation of a hydrophobic breakable vehicle in the form of a breakable oil gel breakable oil foam.

The term "breakable" refers to a unique property of the oil gel or the foam wherein said oil gel foam is stable upon dispensing from a container, yet breaks and spreads easily upon application of mild shear force.

The at least one viscosity-modifying agent is selected from the group consisting of a fatty alcohol, a fatty acid and a wax, wherein said fatty alcohols and/or fatty acids have at least 12 carbon atoms in their carbon backbone.

Fatty Alcohols and Fatty Acids

Preferably, the fatty alcohol and/or fatty acid and/or wax are solid at ambient temperature. In certain embodiments, the fatty alcohol and/or the fatty acid and/or the wax or the mixture of them have a melting point of more than about 40° C.

In an embodiment of the present invention, the fatty alcohol is selected from the group consisting of lauryl alcohol, myristyl alcohol, cetyl alcohol, stearyl alcohol, arachidyl alcohol, behenyl alcohol, tetracosanol, hexacosanol, octacosanol, triacontanol, tetratriacontanol. In an embodiment of the present invention, the fatty acid is selected from the group consisting of dodecanoic acid, tetradecanoic acid, hexadecanoic acid, heptadecanoic acid, octadecanoic acid, eicosanoic acid, docosanoic acid, tetracosanoic acid, hexacosanoic acid, heptacosanoic acid, octacosanoic acid, triacontanoic acid, dotriacontanoic acid, tritriacontanoic acid, tetratriacontanoic acid and pentatriacontanoic acid.

In certain embodiments, the carbon chain of said fatty alcohol or said fatty acid is substituted with a hydroxyl group; and in an additional embodiment said fatty acid is 12-hydroxy stearic acid.

Waxes

Waxes that can be used as part of the viscosity-modifying agent include plant waxes, such as carnauba wax, candelilla wax, ouricury wax, sugarcane wax, retamo wax and jojoba oil; animal waxes, such as beeswax; petroleum derived waxes, including paraffin waxes which are mixtures of saturated of n- and isoalkanes, naphthenes, and alkyl- and naphthene-substituted aromatic compounds; and polyethylene and related derivatives.

In an embodiment the wax is selected from the group consisting of vegetable wax, beeswax, chinese wax, cotton wax, bayberry wax, candelilla wax, carnauba wax, castor wax, cuban palm wax, esparto wax, fir wax, flax wax, flower wax, fat wax, japan wax, sandy wax, lanolin wax, ouricury wax, palm waxes, rice bran wax, rice-oil wax, shellac wax, soy wax, sugar cane wax, ucuhuba wax, a hydrogenated oil, hydrogenated castor oil, hydrogenated cottonseed oil, or hydrogenated jojoba oil, mink wax, montan wax, ozokerite, PEG-6 beeswax, rezo wax, spent grain wax, stearyl dimethicone, a paraffin wax, paraffin 58-62° C. wax, paraffin 51-53° C. wax, paraffin 42-44° C. wax, synthetic mineral wax, fischer-tropsch wax, duroxon wax, or polymekon wax, synthetic waxes, albacer wax, atlasene wax, BASF waxes, cardis waxes, ceramid, glyco waxes, flexo wax, or oxazoline waxes, as well as other waxes, as described in "The Complete Technology Book on Wax and Polishes, Publisher: Asia Pacific Business Press Inc., 2006"

Mixtures of Fatty Alcohols, Fatty Acids and Waxes

It is to be understood that at least one viscosity-modifying agent is required, but that combinations of more than one viscosity-modifying agent are contemplated. In certain embodiments, a combination of two viscosity-modifying agents is preferred. In certain embodiments, the viscosity-modifying agent combination contains at least one fatty alcohol and at least one fatty acid; or at least one fatty alcohol and least one wax; or at least one fatty acid and at least one wax; or at least one fatty alcohol, at least one fatty acid and least one wax.

In one or more embodiments the range of ratio of fatty alcohol to fatty acid; or fatty alcohol to wax is about 100:1 to about 1:100; or about 90:1 to about 1:45; or about 80:1 to about 1:40; or about 70:1 to about 1:35; or about 60:1 to about 1:30; or about 50:1 to about 1:25; or about 40:1 to about 1:20; or about 30:1 to about 1:15; or about 20:1 to about 1:10; or about 15:1 to about 1:5; or about 10:1 to about 1:1; or any ranges in between such as 1:20 to 20:1, or preferably from 1:10 to 10:1, or 1:4 to 4:1, or 2:3 or 3:2.

In certain embodiments, the total concentration of viscosity-modifying agents can be about 0.1% to about 40% by weight; or about 0.4% to about 18% by weight; or about 1% to about 12% by weight.

In certain other embodiments, the composition comprises viscosity-modifying agents from two classes (e.g., at least one fatty alcohol and at least one fatty acid; or at least one fatty alcohol and at least one wax; or at least one fatty acid and at least one wax); and the concentration of each class respectively is within any one of the following ranges (i) between about 0.1% and about 1%, (ii) between about 1% and about 5%, (iii) between about 5% and about 10%, or (iv) between about 10% and about 20%.

Additional Active Agents

Since conditions that can be treated with a tetracycline are often associated with additional conditions, such as inflammation and infection by other microorganisms (other than bacteria), a combination of the tetracycline, and an additional active agent, suitable for the treatment of the underlying disorder or another disorder which substantially concurrently occurs in the same patient is useful for simultaneous therapy of the patient's condition.

Suitable active agents include but are not limited to an active herbal extract, an acaricides, an age spot and keratose removing agent, an allergen, an alpha hydroxyl acid, an analgesic agent, an androgen, an antiacne agent, an antiallergic agent, an antiaging agent, an antibacterial agent, an antibiotic, an antiburn agent, an anticancer agent, an antidandruff agent, an antidepressant, an antidermatitis agent, an antiedemic anent, an antifungal agent, an antihistamine, an antihelminth agent, an anti-hyperkeratosis agent, an antiinfective agent, an antiinflammatory agent, an antiirritant, an antilipemic agent, an antimicrobial agent, an antimycotic agent, an antioxidant, an antiparasitic agent, an antiproliferative agent, an antipruritic agent, an antipsoriatic agent, an antirosacea agent, an antiseborrheic agent, an antiseptic agent, an antiswelling agent, an antiviral agent, an anti-wart agent, an anti-wrinkle agent, an antiyeast agents, an astringent, a beta-hydroxy acid, benzoyl peroxide, a topical cardiovascular agent, a chemotherapeutic agent, a corticosteroid, an immunogenic substance, a dicarboxylic acid, a disinfectant, an estrogen, a fungicide, a hair growth regulator, a haptene, a hormone, a hydroxy acid, an immunosuppressant, an immunoregulating agent, an immunomodulator, an immunostimulant, an insecticide, an insect repellent, a keratolytic agent, a lactam, a local anesthetic agent, a lubricating agent, a masking agent, a metals, a metal oxide, a mitocide, a neuropeptide, a non-steroidal anti-inflammatory agent, an oxidizing agent, a pediculicide, a peptide, a pesticide, a protein, a photodynamic therapy agent, a progesterone, a radical scavenger, a refatting agent, a retinoid, a sanative, a scabicide, a sedative, a self tanning agent, a skin protective agent, a skin whitening agent, a steroid, a steroid hormone, a vasoactive agent, a vasoconstrictor, a vasodilator, a vitamin, a vitamin A, a vitamin A derivative, a vitamin B, a vitamin B derivative, a vitamin C, a vitamin C derivative, a vitamin D, a vitamin D derivative, a vitamin D analog, a vitamin F, a vitamin F derivative, a vitamin K, a vitamin K derivative, a wound healing agent and a wart remover.

Incompatible Excipients and Undesirable Excipients

In certain embodiments, the composition is free of petrolatum, surface active agents, protic solvents, certain polar aprotic solvents and silicone thickening agents; and in certain embodiments the foamable composition is substantially free of such excipients. In the context herein, the term "substantially-free" relates to a composition that contains a total of less than about 0.4% of petrolatum, surface active agents, protic solvents, certain polar aprotic solvents and silicone thickening agents cumulatively. Preferably, the composition comprises less than about 0.2% by weight of petrolatum, surface active agents, protic solvents, certain polar aprotic solvents and silicone thickening agents cumulatively and more preferably less than about 0.1%.

Surface Active Agents

Surfactants have been categorized in to various sub classes depending on there ionic characteristics, namely non-ionic surfactants, anionic, cationic, zwitterionic, amphoteric and amphiphilic surfactants. Surfactants of all kinds are undesirable in accordance with the present invention, as (i) they were found to cause degradation of the tetracycline antibiotic; and (ii) they are generally known to possess irritation potential.

Non-limiting examples of classes of non-ionic surfactants that are undesirable according to the present invention include: (i) polyoxyethylene sorbitan esters (polysorbates), such as polysorbate 20, polysorbate 40, polysorbate 60 and polysorbate 80; (ii) sorbitan esters, such as Sorbitan monolaurate and sorbitan monooleate; (iii) polyoxyethylene fatty acid esters, such as, PEG-8 Stearate, PEG-20 Stearate, PEG-40 Stearate, PEG-100 Stearate, PEG-150 Distearate, PEG-8 laurate, PEG-10 laurate, PEG-12 laurate, PEG-20 laurate, PEG-8 oleate, PEG-9 oleate, PEG-10 oleate, PEG-12 oleate, PEG-15 oleate and PEG-20 oleate; (iv) PEG-fatty acid diesters; (v) polyethylene glycol (PEG) ethers of fatty alcohols; (vi) glycerol esters, such as glyceryl monostearate, glyceryl monolaurate, glyceryl monopalmitate and glyceryl monooleate; (vii) PEG-fatty acid mono- and di-ester mixtures; (viii) polyethylene glycol glycerol fatty acid esters; (ix) propylene glycol fatty acid esters; (x) mono- and diglycerides; (xi) sugar esters (mono-, di- and tri-esters of sucrose with fatty acids) and (xii) polyethylene glycol alkyl phenols.

In additional embodiments, the term "substantially surfactant-free" relates to a composition wherein the ratio between the viscosity-modifying agent and the surfactant is between 10:1 or 5:1; or between 20:1 and 10:1 or between 100:1 and 20:1.

In the context of the present invention, while fatty alcohols, fatty acids and certain waxes are amphiphatic, these substances are not effective as stand-alone surfactants in foamable emulsion compositions, because of their very weak emulsifying capacity and further due to their weak foaming capacity on their own. Hence, fatty alcohols, fatty acids and certain waxes, which constitute the viscosity-modifying agent of the present invention, are not undesirable.

Protic Solvents

Protic solvents, such as short chain alcohols, glycols and glycerin are incompatible with tetracyclines and therefore they are undesirable.

Aprotic Polar Solvents

We discovered that certain polar aprotic solvents are incompatible with tetracycline antibiotics. Thus, aprotic polar solvents, such as dimethyl sulfoxide (DMSO), dimethylformamide (DMF), acetonitrile, acetone, methyl ethyl ketone, 1,4-Dioxane and tetrahydrofuran (THF), N-methylpyrrolidone, pyridine, piperidine, dimethylformamide, N-methyl-2-pyrrolidone and 1-methyl-2-pyrrolidinone) and azone (1-dodecylazacycloheptan-2-one) are undesirable.

Silicone Thickening Agents

Silicone thickening agents comprise one or more polysiloxane-derived components. Such polysiloxanes are typically cross-linked and they have rubber-like characteristics, which require their solubilization in an oil, usually a silicone oil. An example of such a silicone thickening agent is ST-Elastomer 10 (Dow Corning), is a mixture of high molecular weight dimethicone crosspolymer (12%), in cyclopentasiloxane (cyclomethicone, silicone solvent). With reference to bioavailability of an active agent in the skin following topical application, it is conceivable that cross co-polymers will create a non permeable film which should block skin penetration and therefore, it is undesirable. Further, in the context of a breakable foam, cyclomethicone is know as a defoamer and therefore it presence in high concentrations in the breakable hydrophobic composition is undesirable.

In one or more other specific embodiments the drug carrier is formulated substantially free of elastomers. In one or more other specific embodiments the drug carrier is formulated essentially free of elastomers. In one or more other specific embodiments the drug carrier is formulated substantially free of silicones. In one or more other specific embodiments the drug carrier is formulated essentially free of silicones. In one or more other specific embodiments the drug carrier is formulated with less than about 30% silicone, or less than about 25% silicone, or less than about 20% silicone, or less than about 15% silicone, or less than about 10% silicone, or less than about 7.5% silicone, or less than about 5% silicone or less than about 2% silicone; or less than about 1% silicone; or less than about 0.5% silicone.

Petrolatum

Petrolatum, also termed "Vaseline", can be disadvantageous, due to its greasy nature. It is known to leave greasy and sticky feeling after application and occasionally stain cloths. Thus, white petrolatum and other semi-solid oils are not a preferred hydrophobic oil according to the present invention. Additionally, compositions containing a substantial amount of semi-solid hydrophobic oils, e.g., white petrolatum, as the main ingredients of the oil phase of the emulsion, will likely exhibit high viscosity and poor flowability and can be inappropriate candidates for a foamable composition. Thus in one or more embodiments semi-solid hydrophobic oils are a subsidiary component in the composition, for example being present at less than about 25%, less than about 20%, less than about 15%, less than about 10%, or less than about 5% by weight of the hydrophobic breakable composition. In other embodiments formulations with more than 50% petrolatum have been made which produce foam of excellent quality, a collapse time of in excess of three minutes.

Skin Penetration

Surprisingly, despite the fact that said tetracyclines are hydrophobic at neutral pH (especially minocycline), they do not dissolve in the hydrophobic oils, even at a concentration of 0.05%. So, it arises that at any concentration of more than 0.1% the majority of the tetracycline is suspended, rather than dissolved. However, whilst intuitively the bioavailability of the drug in the skin following topical application is expected to be low, substantial amounts of the tetracycline are found in the skin following one application, as shown in in-vitro skin penetration tests. The amounts found in the skin following one application of a hydrophobic breakable composition comprising 1% minocycline and 4% minocycline for 24 hours was 9.49 and 43.12 µg/cm$^2$ respectively. The weight of skin at the delivery area is about 100 mg, which implies that the concentration of minocycline in the skin following 24 hours of exposure is about 90 µg/gr of skin for the 1% formulation and about 430 µg/gr for the 4% formulation. According to the literature, the minimum inhibitory concentration (MIC) for minocycline is less than 4 µg/mL, and therefore, it can be concluded that the concentrations found in the skin are sufficient, or even higher than required to treat bacterial skin infections.

Even more surprisingly, whilst the tetracycline penetrates well into the skin, the tetracycline does not permeate through the skin. This is a very important feature of the composition of the present invention, as it minimizes the probability of systemic side effects, when topical application is carried out. In one or more embodiments there is no or negligible transdermal delivery. In one or more embodiments the ratio of intradermal to transdermal delivery is about or more than 100:1.

This means that the current hydrophobic vehicle of minocycline is unique in targeting the delivery of the drug intra-dermally, rather than transdermally.

In an embodiment, the concentration of the tetracycline in the hydrophobic breakable composition, when tested in the Franz-cell in vitro model, using human or pig's skin is higher than the lowest intradermnal concentration of the tetracycline that is required to kill skin bacteria, such as *staphylococcus* and *streptococcus* strains.

Thus, in an embodiment, the composition, wherein, when tested in the Franz-cell in vitro model using human or pig's skin, affords an amount of the tetracycline in the skin which is higher than the respective amount transferred transdermally. In certain embodiments, when tested in the Franz-cell in vitro model using human or pig's skin, the ratio between the amount of the tetracycline in the skin and the respective amount transferred transdermally is higher than about 100; or between 100 and 10; or between 10 and 2; or more than 1.

Anti-Microbial Effect

In an in-vitro study, it was revealed that the hydrophobic breakable composition comprising 1% minocycline and 4% minocycline inhibited the growth of *streptococcus pyogenes, pseudomonas aeruginosa, staphylococcus aureus*, as well as a methicillin-resistant strain of *staphylococcus aureus* (MRSA). The formulation was also effective against *propionbacterium acnes*, the causative microorganism in acne.

This result was unexpected, as the minocycline was primarily suspended in the composition, thus minimizing its expected availability for the antibacterial effect.

Anti-Inflammatory and Anti-Apoptosis Effect of the Composition Comprising a Tetracycline This effect of minocycline, when treated after the induction of inflammation is surprising, as the literature teaches that "pre-treatment, but not post-treatment, with minocycline markedly attenuated increased pro-inflammatory cytokines release and oxidative and nitrosative stress in mononeuropathic rats." (see for example, Padi S S, Kulkarni S K, "Minocycline prevents the development of neuropathic pain, but not acute pain: possible anti-inflammatory and antioxidant mechanisms", Eur J Pharmacol. 2008; 601:79-

87). By contrast, when minocycline was included in the hydrophobic breakable composition of the present invention and applied to skin specimens after induction of UV damage, it significantly decreased apoptosis, as measured by caspase 3 activity; and to elevate skin cell viability.

In an embodiment, the concentration of the tetracycline is determined by its ability to inhibit the occurrence of apoptosis; or by its ability to decrease caspase 3 activity or by its ability to decrease the occurrence of pro-inflammatory cytokines in an ex-vivo human skin model.

Fields of Applications

The hydrophobic breakable tetracycline gel and foam compositions of the present disclosure are suitable for treating any inflicted surface. In one or more embodiments, foamable carrier is suitable for administration to the skin, a body surface, a body cavity or mucosal surface, e.g., the cavity and/or the mucosa of the nose, mouth, eye, respiratory system, vagina, urethra or rectum and the ear canal (severally and interchangeably termed herein "target site").

Many conditions can be contemplated based on the antimicrobial properties of the tetracyclines, plus the anti-inflammatory, anti-oxidative and neuroprotective effects of certain tetracycline compound (such as minocycline and doxycycline).

By selecting a suitable tetracycline compound, or a combination of a tetracycline with at least one additional active agent, the composition of the present disclosure is useful in treating an animal or a human patient having any one of a variety of dermatological disorders, including, but not limited to the list, provided here in an alphabetical manner: abscess, acne, acne conglobata, acne fulminans, acne vulgaris, acne scars, acute febrile neutrophilic dermatosis, acute lymphangitis, allergic contact dermatitis, alopecia, athlete's foot, atopic dermatitis, bacterial skin infections, baldness, basal cell carcinoma, blisters, bromhidrosis, bullous pemphigoid, burn, calluses candidiasis, carbuncles, cellulitis, chemical burns, chicken pox, cholesteatoma, cholinergic urticaria, chronic effects of sunlight, cold sores, cold urticaria, comedones, corns, creeping eruption, cutaneous abscess, cutaneous larva migrans, cutaneous myiasis, dark spots, delusional parasitosis, Dercum disease, dermatitis, dermatitis herpetiformis, dermatological pain, dermatological inflammation, dermographism, dermatophytoses, drug eruptions and reactions, dyshidrotic eczema, ectodermal dysplasia, eczema, ecthyma, epidermoid cyst, epidermal necrolysis, erysipelas, erysipelas, erythrasma, exfoliative dermatitis, erythema multiforme, erythema nodosum, folliculitis, fungal nail infections, fungal skin infections, furuncles, gangrene, genital herpes, granuloma annulare, head lice, hidradenitis suppurativa, hives, folliculitis, hirsutism, hyperhidrosis, hypohidrosis, ichthyosis, impetigo, inflammatory acne, ingrown nails, intertrigo, irritant contact dermatitis, ischemic necrosis, itching, jock itch, Kaposi's sarcoma, keratosis pilaris, lichen simplex chronicus, lichen planus, lichen sclerosus, lymphadenitis, lymphadenitis, lymphangitis, malignant melanoma, mastocytosis, measles, melanoma, melanoma, miliaria, moles, molluscum contagiosum, MRSA, necrotizing subcutaneous infection, necrotizing fasciitis, necrotizing myositis, nodular papulopustular acne, non-inflammatory acne, nummular dermatitis, oral herpes, panniculitis, parapsoriasis paronychia, parasitic skin infections, pemphigus, photo-allergy, photo-damage, photo-irritation, photosensitivity, papules, pediculosis, perioral dermatitis, pimples, *pityriasis rosea, pityriasis Lichenoides, pityriasis rosea, pityriasis rubra pilaris*, poison ivy, post-operative or post-surgical skin conditions, pressure ulcers, pressure urticaria, pruritis, pseudofolliculitis barbae, psoriasis, PUPPP, purpura, pustules, pyogenic granuloma, rash, ringworm, rosacea, roseola, rubella, scabies, scalded skin syndrome, scarring, scleroderma, sebaceous cyst, seborrheic dermatitis, seborrheic keratosis, shingles, skin aging, skin cancer, skin neoplasia, skin neoplasms, skin rash, skin ulcers, squamous cell carcinoma, staphylococcal scalded skin syndrome, stasis dermatitis, Stevens-Johnson syndrome, sunburn, sun spots, thermal burns, *tinea corporis, tinea cruris, tinea pedis, tinea versicolor*, toxic epidermal necrolysis, trauma or injury to the skin, varicella zoster virus, vitamin D deficiency, viral skin infections, vitiligo, warts, water hives, wrinkles, xerosis, yeast skin infections and zoster.

Likewise, the gel or foam composition of the present disclosure are suitable for treating a disorder of a body cavity or mucosal surface, e.g., the surface and/or mucosa of the nose, mouth, eye, ear, respiratory system, vagina, urethra, or rectum. Non limiting examples of such conditions include *chlamydia* infection, gonorrhea infection, hepatitis B, herpes, HIV/AIDS, human papillomavirus (HPV), genital warts, bacterial vaginosis, candidiasis, chancroid, granuloma Inguinale, lymphogranloma venereum, mucopurulent cervicitis (MPC), molluscum contagiosum, nongonococcal urethritis (NGU), trichomoniasis, vulvar disorders, vulvodynia, vulvar pain, yeast infection, vulvar dystrophy, vulvar intraepithelial neoplasia (VIN), contact dermatitis, pelvic inflammation, endometritis, salpingitis, oophoritis, genital cancer, cancer of the cervix, cancer of the vulva, cancer of the vagina, vaginal dryness, dyspareunia, anal and rectal disease, anal abscess/fistula, anal cancer, anal fissure, anal warts, Crohn's disease, hemorrhoids, anal itch, pruritus ani, fecal incontinence, constipation, polyps of the colon and rectum.

In one or more embodiments, the hydrophobic breakable gel is specifically useful for ophthalmic administration. Unlike customary ophthalmic ointments, which create a greasy film on the eye and blur the vision, the gel liquefies upon first eye blink and will spread on the eye surface.

Eye conditions that can be contemplated based on the antimicrobial properties of the tetracycline, plus the anti-inflammatory, anti-oxidative and neuroprotective effects of certain tetracycline compound (such as minocycline and doxycycline) can be categorized, in a non limiting fashion by their symptoms as follows: eye redness, eye pain or light sensitivity, blurred vision, loss of vision, visual disturbances—floaters, flashing, distortion, halos, etc., itching/burning, tearing/discharge, sensation of something in the eye, eyelid problems, double vision.

Examples of relevant conditions include macular degeneration, age-related macular degeneration, "dry" macular degeneration and "wet" macular degeneration, which are associated with photodamage and apoptosis, cataract, which is associated with apoptosis, glaucoma, open-angle glaucoma, closed-angle glaucoma (associated with optical nerve death and apoptosis), retinopathy, proliferative diabetic retinopathy (apoptosis), macular Edema (inflammation), conjunctivitis, uveitis and trachoma (infection).

Non-limiting examples of ophthalmic conditions that can be treated by a hydrophobic breakable tetracycline composition of the present invention; or such conditions whose complications can be treated by said composition; are provided herewith in their alphabetical order: allergy, blepharitis, cataract, central serous chorioretinopathy, color vision problems, corneal abrasion, corneal edema, corneal ulcer, conjunctivitis, contact lens complications, dacryocystitis, blurred distance vision, dry eye, eale's disease, episcleritis, eyelid ectropion, eyelid entropion, eyelid cellulitis, eye strain, focusing spasm, glaucoma, acute glaucoma, iritis, keratoconus, lyme disease, macular degeneration, macular edema, macular hole, eye medication toxicity, myasthenia gravis, ocular cicatricial pemphigoid, ophthalmic migraine, presbyopia, obstructed tear duct, optic neuritis, optic nerve stroke, orbital fracture, orbital cellulitis, phlyetenulosis, pterygium, recurrent corneal erosion, retinal artery occlusion, retinal detachment, retinal tear, retinal vein occlusion, sarcoidosis, scleritis, sinus disease, strabismus (ocular misalignment), subconjunctival hemorrhage, temporal arteritis, thyroid eye disease, trichiasis, eyelid tumor, twitching of eyelid (eyelid myokymia), uveitis, vitreous detachment and vitreous hemorrhage.

In light of the hygroscopic nature of the composition, it is further suitable for the treatment and prevention of post-surgical adhesions. Adhesions are scars that form abnormal connections between tissue surfaces. Post-surgical adhesion formation is a natural consequence of surgery, resulting when tissue repairs itself following incision, cauterization, suturing, or other means of trauma. When comprising appropriate protective agents, the foam is suitable for the treatment or prevention of post surgical adhesions. The use of foam is particularly advantageous because foam can expand in the body cavity and penetrate into hidden areas that cannot be reached by any other alternative means of administration.

In one or more embodiments, there is provided a composition for use in preventing or ameliorating or treating photodamage or radiation damage or photoaging or reducing oxidative stress or inflammation in skin pathologies which are known to be accompanied by apoptic cell death or any two or more thereof.

In one or more embodiments, there is provided a composition for use in preventing or ameliorating or treating a disorder, the tetracyline composition having at least one property or activity selected from a list including regenerative, anti-apoptotic, anti-inflammatory, anti-photodamaging anti-radiation damage and anti-photoaging.

In one or more embodiments, there is provided a composition comprising a tetracycline for use in preventing protecting from or ameliorating or treating UVB-induced skin damage.

In one or more embodiments, there is provided a composition comprising a tetracycline for use in preventing, protecting from or ameliorating or treating a disorder with symptoms including increased apoptosis and or decreased cell viability, where the formulation acts to decrease apoptosis and or increase cell viability. In one or more embodiments there is provided a composition for use in decreasing apoptosis and or increasing cell viability.

In one or more embodiments, there is provided a composition comprising a tetracycline for use in preventing or ameliorating or treating disorders by reducing oxidative stress and inflammation in skin pathologies which are known to be accompanied by apoptotic cell death including rosacea and impetigo.

In one or more embodiments there is provided a tetracycline composition having regenerative, or anti-apoptotic, or anti-inflammatory, or anti-photodamaging, or anti-photoaging activity, or protective and or therapeutic properties in the case of UVB-induced skin damage, or which decreases apoptosis and or increases cell viability, or in reducing oxidative stress and inflammation in skin pathologies accompanied by apoptotic cell death including rosacea and impetigo, or antibacterial activity, or any two or more thereof.

Cosmetic Use

In one or more embodiments, the composition may be used for cosmetic use. For example it may be used as part of a cosmetic formulation to prevent a cosmetic disorder or to improve the skin.

Administration

The compositions disclosed herein can be applied to the target site as a gel or a foam. Application can be hourly, 2 hourly, 3 hourly, four hourly, six hourly or eight hourly, twelve hourly, daily, alternate-day or intermittent, as necessary. For reasons of compliance less frequent applications, where possible are preferable such as twice-daily or daily single applications. In cases where prolonged or long term treatment is required a higher initial dose is provided followed by a gradual reduction to a lower maintenance dose, which can be increased if further outbreaks occur.

EXAMPLES

The invention is described with reference to the following examples, in a non-limiting manner. The following examples exemplify the foamable compositions and methods described herein. The examples are for the purposes of illustration only and are not intended to be limiting. Many variations will suggest themselves and are within the full intended scope.

Materials

Exemplary possible ingredients suitable for the production of foamable compositions disclosed herein. Equivalent materials from other manufacturers can also be used satisfactorily.

| Chemical Name | Function | Commercial Name | Supplier |
|---|---|---|---|
| Beeswax white | Foam adjuvant | Beeswax white | Henry Lamotte |
| Behenyl alcohol | Foam adjuvant | Lanette 22 | Cognis |
| Cetostearyl alcohol | Foam adjuvant | Speziol C16-C18 | Cognis |
| Cetyl alcohol | Foam adjuvant | Speziol C16 | Cognis |
| Coconut oil | Solvent | Coconut oil | Henry Lamotte |
| Cyclomethicone-5 | Solvent | ST-cyclomethicone-5 | Dow |
| Heavy Mineral Oil | Solvent | Paraffin oil liquid heavy | Gadot |
| Hydrogenated castor oil | Foam adjuvant | Cutina HR | Cognis |
| Isostearic acid | Foam adjuvant | Isostearic acid | Stearinerie Dubois |
| Lanolin | Foam adjuvant | Lanolin | Spectrum |
| Light Mineral Oil | Solvent | Pioner 2076P | Hansen & Rosenthal |
| MCT Oil | Solvent | Captex 355 | Abitec |
| Minocycline HCl | Active agent | Minocycline HCl | Hovione |
| Myristyl alcohol | Foam adjuvant | Speziol C14 | Cognis |
| Octyldodecanol | Solvent | Eutanol G | Cognis |
| Paraffin wax 51-53 | Wax | Paraffin 51-53 | Merck |
| PPG 15 stearyl ether | Solvent | Arlamol E | Uniqema |
| Propane/Isobutane/Butane (20:78:2) | Propellant | A-46 | Aeropres |
| Propane/Isobutane/Butane (55:18:27) | Propellant | AP-70 | Aeropres |
| Silicon dioxide | Dispersant | Aerosil R 972 PET | Evonik-Goldschmidt |
| Soybean oil | Solvent | Soybean oil | Spectrum |
| Stearic acid | Foam adjuvant | Edenol ST1M | Cognis |
| Stearyl Alcohol | Foam adjuvant | Speziol C18 | Cognis |

Part A—Gel Formulations

Example 1—General Manufacturing Procedures for a Gel

The following procedures are used to produce gel samples described in the examples below, in which only the steps relevant to each formulation are performed depending on the type and nature of ingredients used.

Step 1: Hydrophobic oil are heated to 60-70° C.

Step 2: Fatty alcohols if present, fatty acids if present, wax if present, are added to the hydrophobic oil and the formulation is mixed until complete melting.

Step 3: The formulation is cooled down to 30-40° C., the tetracycline antibiotic is added and the formulation is mixed until homogeneity is obtained.

Step 4: The formulation is cooled down to room temperature under mixing and packaged into suitable containers.

By way of non-limiting example, tests are briefly set out below as would be appreciated by a person of the art.

Viscosity is measured with Brookfield LVDV-II+PRO with spindle SC4-25 at ambient temperature and 20, 10, 5 and 1 RPM. Viscosity is usually measured at 10 RPM. However, at the apparent upper limit for the spindle of about 50,000 CP, the viscosity at 1 RPM may be measured, although the figures are of a higher magnitude.

Chemical Stability: the amount of the tetracycline antibiotic is analyzed chromatographically. Analysis is carried out after formulation preparation and at appropriate time intervals thereafter. The samples are typically stored in controlled temperature incubators at one or more of 5° C., 25° C. and 40° C. for several weeks or months. At appropriate time intervals samples are removed from the incubators and the concentration of active agent is measured.

Example 2—Gel Formulations with Low Viscosity

The different hydrophobic oils suitable for use in topical pharmaceutical compositions are generally liquid oils have a low viscosity. When these oils are used as-is for active agents topical delivery, they have inter alia two non desirable properties: (1) because of their low viscosity, they tend to drop and to be runny and therefore not easy for the patient to apply onto the skin, (2) they have poor suspending properties leading to the rapid sedimentation of non-dissolved active ingredients (APIs), as described in Table 2.

TABLE 2

Low viscosity oleaginous preparations

| | Formulations | | | |
|---|---|---|---|---|
| | 001P % w/w | 001 % w/w | 002P % w/w | 002 % w/w |
| Ingredients | | | | |
| Heavy mineral oil | 75.00 | 75.00 | — | — |
| Light mineral oil | 25.00 | 25.00 | — | — |
| Soybean oil | — | — | 100 | 100 |
| Total | 100.00 | 100.00 | 100.00 | 100.00 |
| Minocycline HCl | — | 0.1 | — | 0.1 |
| Results | | | | |
| Viscosity at 10 rpm (cP) | 96 | 92 | 47 | 49 |

As shown in formulations 001P and 002P, mixtures of mineral oils and soybean oil have a low viscosity. Formulations 001 and 002, show that after the addition of Minocycline HCl, the viscosity of the formulation remains unchanged and that the active ingredient sediments.

Example 3—Mineral Oil-Based Formulations with Improved Viscosity

The influence of the combination of a tetracycline with fatty alcohols, fatty acids and waxes on formulation viscosity was assessed, as described in Table 3a. Formulations containing a mixture of mineral oils with fatty alcohols, fatty acids or waxes were prepared, and their viscosity was measured before and after the addition of a tetracycline, namely minocycline HCl. Table 3a below presents the results of formulation viscosity before and after the addition of a tetracycline, as well as the percentage of viscosity increase due to the addition of the active ingredient.

TABLE 3a

Combination of a tetracycline with fatty alcohols, fatty acid and waxes

| | Formulations | | | |
|---|---|---|---|---|
| | 003 % w/w | 004 % w/w | 005 % w/w | 005B % w/w |
| Ingredients | | | | |
| Heavy mineral oil | 65 | 65 | 65 | 65 |
| Light mineral oil | 25 | 25 | 25 | 30 |
| Stearyl alcohol | 10 | — | — | — |
| Stearic acid | — | 10 | — | — |
| Beeswax | — | — | 10 | — |
| Hydrogenated Castor oil | — | — | — | 5 |
| Total | 100.00 | 100.00 | 100.00 | 100.00 |
| Results | | | | |
| Viscosity Results at 10 rpm (cP) | | | | |
| Without Minocycline HCl | 951 | 1858 | 942 | 848 |
| With 0.1% Minocycline HCl | 2652 | 8142 | 1695 | 6223 |
| % Viscosity Increase | +179% | +338% | +80% | +634% |

Very surprisingly, it was discovered that the addition of minocycline HCl to mineral oil-based formulations 003 to 005B led to a very substantial increase in viscosity, despite the very low amount of minocycline HCL used, namely 0.1%. This totally unexpected results show that the combination of a tetracycline, even at very low concentrations, with fatty alcohols, fatty acids or waxes has a strong synergistic effect on oleaginous formulation viscosity.

The influence of the addition of different concentrations of a tetracycline on a mineral oils-based formulation was then studied when the active ingredient is combined with a mixture of mineral oils, fatty alcohols, fatty acids and waxes, as described in Table 3b and 3c.

TABLE 3b

Oleaginous preparations

| | Formulations |
|---|---|
| | 238P % w/w |
| Ingredients | |
| Heavy mineral oil | 59.25 |
| Light mineral oil | 25.00 |
| Cyclomethicone | 5.00 |
| Stearyl alcohol | 1.50 |
| Beeswax | 2.00 |
| Stearic acid | 2.00 |
| Hydrogenated castor oil | 1.50 |
| Behenyl alcohol | 1.00 |

TABLE 3b-continued

Oleaginous preparations

| | Formulations |
|---|---|
| | 238P % w/w |
| Cetostealyl alcohol | 2.50 |
| Silicon dioxide | 0.25 |
| Total | 100.00 |
| Minocycline HCl | — |
| Results | |
| Viscosity Results at 1.0 rpm (cP) | 6639 |
| % Viscosity Increase | — |

TABLE 3c

Oleaginous preparations

| | Formulations | | | | |
|---|---|---|---|---|---|
| | 238P % w/w | 238A % w/w | 238B % w/w | 238C % w/w | 238D % w/w |
| Ingredients | | | | | |
| Formulation 238P | 100.00 | 99.90 | 99.80 | 99.50 | 99.00 |
| Minocycline HCl | — | 0.10 | 0.20 | 0.50 | 1.00 |
| Results | | | | | |
| Viscosity Results at 10 rpm (cP) | 6639 | 15789 | 18476 | 20876 | 20748 |
| % Viscosity Increase | — | +138% | +178% | +214% | +213% |

The combination of a tetracycline with a mixture of mineral oils, fatty alcohols, fatty acids and waxes has a strong synergistic effect and increases the formulation viscosity. The viscosity of a formulation containing 0.50% minocycline HCl is about three times higher than the viscosity of the placebo formulation. The effect on the formulation viscosity is directly related to the concentration of the tetracycline: the higher the tetracycline concentration, the higher the viscosity of the formulation. In formulation 238, it appears that the viscosity increasing effect of minocycline HCl reaches a plateau when the active ingredient is present at a concentration of about 0.50%.

In one or more embodiments, there is provided an oleaginous formulation containing mineral oils and a tetracycline in synergistic combination with a fatty alcohol, and/or a fatty acid and/or a wax, wherein the viscosity of the formulation is increased by the addition of the active ingredient by more than about 50%, more than about 100%, more than about 200%, more than about 300%, more than about 500%.

In one or more embodiments, there is provided an oleaginous formulation containing hydrophobic oils, an active ingredient in synergistic combination with a solidifying agent, wherein the viscosity of the formulation is increased by the addition of the active ingredient by more than about 50%, more than about 100%, more than about 200%, more than about 300%, more than about 500%.

In one or more embodiments, there increase in the formulation viscosity is related to the concentration of the active agent.

In one or more embodiments, the viscosity of the formulation is directly proportional to the concentration of the active agent: the higher the concentration of the active ingredient, the higher the formulation viscosity.

In one or more embodiments, the viscosity increasing effect of the active ingredient reaches a plateau when the concentration of the active ingredient is increased.

In one or more embodiments, the viscosity of the formulation containing the active ingredient is twice the viscosity of the sample formulation when the active ingredient is present at a concentration of less than about 10%, less than about 5%, less than about 1%, less than about 0.5%, less than about 0.1%, less than about 0.05%, less than about 0.01%.

Example 4—Vegetable Oils-Based Formulations with Improved Viscosity

Formulation with different vegetable oils, such as soybean oil and coconut oil were prepared as described in Table 4a, to study the influence of the combination of a tetracycline with a fatty alcohol on formulation viscosity.

TABLE 4a

Formulation based on vegetable oils

| | Formulations | |
|---|---|---|
| | 006 % w/w | 007 % w/w |
| Ingredients | | |
| Soybean oil | 90 | — |
| Coconut oil | — | 90 |
| Stearyl alcohol | 10 | 10 |
| Total | 100.00 | 100.00 |
| Minocycline HCl | — | 1.15 |
| Results | | |
| Viscosity Results at 10 rpm (cP) | | |
| Without Minocycline HCl | 2771 | 24571 |
| With 0.1% Minocycline HCl | 1826 | 22459 |
| % Viscosity Increase | −34% | −9% |

In contrast with the phenomenon observed with mineral oil-based formulations, no increase in the viscosity was observed with the vegetable oils-based formulation when a tetracycline is combined with a fatty alcohol.

The influence of the addition of a tetracycline on vegetable oils-based formulations was then studied when the active ingredient is combined with a mixture of vegetable oils, fatty alcohols, fatty acids and waxes, as described in Table 4b.

TABLE 4b

Formulation based on vegetable oils with improved viscosity

| | Formulations | | |
|---|---|---|---|
| | 244P % w/w | 244B % w/w | 244A % w/w |
| Ingredients | | | |
| Soybean oil | 50.00 | 50.00 | 50.00 |
| Coconut oil | 23.60 | 23.60 | 23.60 |
| Light Mineral oil | 5.55 | 4.40 | 0.95 |
| Cyclomethicone | 5.00 | 5.00 | 5.00 |
| Cetostearyl alcohol | 3.50 | 3.50 | 3.50 |
| Stearic acid | 3.00 | 3.00 | 3.00 |
| Myristyl alcohol | 2.50 | 2.50 | 2.50 |
| Hydrogenated castor oil | 2.00 | 2.00 | 2.00 |
| Beeswax | 2.00 | 2.00 | 2.00 |
| Stearyl alcohol | 1.50 | 1.50 | 1.50 |

TABLE 4b-continued

Formulation based on vegetable oils with improved viscosity

| | Formulations | | |
|---|---|---|---|
| | 244P % w/w | 244B % w/w | 244A % w/w |
| Behenyl alcohol | 1.10 | 1.10 | 1.10 |
| Silicon dioxide | 0.25 | 0.25 | 0.25 |
| Total | 100.00 | 100.00 | 100.00 |
| Minocycline HCl | — | 1.15 | 4.60 |
| Results | | | |
| Viscosity Results at 10 rpm (cP) | 7214 | 14429 | 17084 |
| % Viscosity Increase | — | +100% | +137% |

As shown in Table 4b, unexpectedly, the combination of a tetracycline with a mixture of hydrophobic oils, fatty alcohols, fatty acids and waxes has a strong synergistic thickening effect and increases the formulation viscosity. The viscosity of a formulation containing 1.15% Minocycline HCl was about twice higher than the viscosity of the placebo formulation. Moreover, the effect on the formulation viscosity was directly related to the concentration of the tetracycline: the higher the tetracycline concentration, the higher the viscosity of the formulation.

Thus, in one or more embodiments, there is provided an oleaginous formulation containing vegetable oils and a tetracycline in synergistic combination with a fatty alcohol, a fatty acid and a wax, wherein the viscosity of the formulation is increased by the addition of the active ingredient by more than about 50%, more than about 100%, more than about 200%, more than about 300%, more than about 500%.

In another experiment, a sample of formulation 244B gel was stored during 6 months at 40° C. and tested for minocycline content uniformity. It was found that minocycline was homogeneously dispersed in the formulation, and remained so even after prolonged incubation at 40° C. Additionally, the assay of minocycline in the formulation did not change after 6 months of storage at 40° C. Thus, in one or more embodiments, there is provided a hydrophobic gel formulation wherein the tetracycline is homogeneously dispersed the gel and remains homogeneously dispersed and stable after 6 months of incubation at 40° C.

Part B—Foam Formulations

Example 5—General Manufacturing Procedures for a Foam

The following procedures are used to produce the foam samples described in the examples below, in which only the steps relevant to each formulation are performed depending on the type and nature of ingredients used.

Step 1: Hydrophobic oils such as mineral oils are mixed at room temperature. Others solvents such as silicones, if present, are added at room temperature under mixing until formulation homogeneity is obtained.

Step 2: The formulation is warmed to 70-80° C. and solid compounds such as fatty alcohols, fatty acids and waxes are added and mixed until complete dissolution.

Step 3: The formulation is cooled down to 30-40° C. and active agents are added under mixing until formulation homogeneity is obtained.

Step 4: The formulation is packaged in aerosol canisters which are crimped with a valve, pressurized with propellant and equipped with an actuator suitable for foam dispensing. Optionally a metered dosage unit can utilized, to achieved delivery of desirable and/or repeatable measured doses of foam.

Step 5: Pressurizing is carried out using a hydrocarbon gas or gas mixture. Canisters are filled and then warmed for 30 seconds in a warm bath at 50° C. and well shaken immediately thereafter.

Tests

By way of non-limiting examples certain tests to characterize the foam and its stability are briefly set out below.

Collapse Time

Collapse Time, which is the measure of thermal stability, is examined by dispensing a given quantity of foam and photographing sequentially its appearance with time during incubation at 36° C. The collapse time result is defined as the time when the foam height reaches 50% of its initial height or if the foam has not yet reached 50% of its initial height after say 180 seconds then the collapse time is recorded as being >180. By way of illustration one foam may remain at 100% of its initial height for three minutes, a second foam may reach 90% of its initial height after three minutes, a third foam may reach 70% of its initial height after three minutes, and a fourth foam may reach 51% of its initial height after three minutes, nevertheless in each of these four cases the collapse time is recorded as >180 seconds since for practical purposes for easy application by a patient to a target the majority of the foam remains intact for more than 180 seconds. If the foam for example reaches 50% of its original height after say 100 seconds it would be recorded as having a collapse time of 100 seconds. It is useful for evaluating foam products, which maintain structural stability at skin temperature for at least 1 minute. Foams which are structurally stable on the skin for at least one minute are termed "short term stable" carriers or foams.

Density

The foam product is dispensed into preweighed tubes of a known volume and weight. Replicate measurements of the mass of foam filling the tube are made and the density is calculated.

Viscosity

Viscosity is measured with Brookfield LVDV-II+PRO with spindle SC4-25 at ambient temperature and 10, 5 and 1 RPM. Viscosity is usually measured at 10 RPM. However, at about the apparent upper limit for the spindle of ~>50,000 cPs, the viscosity at 1 RPM may be measured, although the figures are of a higher magnitude. Unless otherwise stated viscosity of the pre-foam formulation (PFF) is provided. It is not practical to try and measure the viscosity of the foamable formulation with regular propellants since they have to be stored in sealed pressurized canisters or bottles. In order to simulate the viscosity in the foamable formulations with propellant an equivalent weight of pentane (a low volatile hydrocarbon) is added to and mixed with the pre-foam formulation and left overnight. The viscosity is then measured as above.

Chemical Stability

The amount of active agent present is analyzed chromatographically in foam released from various pressurized canisters. Analysis is carried out at baseline and at appropriate time intervals thereafter. The canisters are typically stored in controlled temperature incubators at one or more of 5° C., 25° C. and 40° C. At appropriate time intervals canisters are removed and the amount of active agent in the foam sample is measured.

Bubble Size

Foams are made of gas bubbles entrapped in liquid. The bubble size and distribution reflects in the visual texture and smoothness of the foam. Foam bubbles size is determined by dispensing a foam sample on a glass slide, taking a picture of the foam surface with a digital camera equipped with a macro lens. The diameter of about 30 bubbles is measured relatively to calibration standard template. Statistical parameters such as mean bubble diameter, standard deviation and quartiles are then determined. Measuring diameter may also be undertaken with image analysis software. The camera used was a Nikon D40X Camera (resolution 10 MP) equipped with Sigma Macro Lens (ref: APO MACRO 150 mm F2.8 EX DG HSM). Pictures obtained are cropped to keep a squared region of 400 pixels×400 pixels.

Microscopic Observation

The light microscope enables observing and measuring particles from few millimeters down to one micron. Light microscope is limited by the visible light wavelength and therefore is useful to measuring size of particles above 800 nanometers and practically from 1 micron (1,000 nanometers).

Shakability

Shakability represents the degree to which the user is able to feel/hear the presence of the liquid contents when the filled pressurized canister is shaken. Shaking is with normal mild force without vigorous shaking or excessive force. When the user cannot sense the motion of the contents during shaking the product may be considered to be non-shakable. This property may be of particular importance in cases where shaking is required for affecting proper dispersion of the contents.

| Table of Shakability scoring | |
|---|---|
| Good shakability (conforms to required quality specification) | 2 |
| Moderate shakability (conforms to required quality specification) | 1 |
| Not shakable (fails to meet required quality specification) but may still be flowable and allow foam formation of quality | 0 |
| Is substantially not able to pass through valve | Block |

Centrifugation

The centrifugation used in this procedure serves as a stress condition simulating the aging of the liquid formulation under investigation. Under these conditions, the centrifugal force applied facilitates coalescence of dispersed globules or sedimentation of dispersed solids, resulting in loss of the desired properties of the formulation.

Centrifugation can also be executed at a higher rpm for a shorter period or a lower rpm for a longer period bearing in mind the G-force experienced by the formulations is many fold greater than the one G to which a formulation would be exposed to during its shelf life. Centrifugation can also be executed at a higher rpm for the same period, say 3000 or 10,000 rpm to simulate an extremely high stress level.

Example 6—Surfactant—Free Hydrophobic Foam Formulations

Surface active agents are known to be useful foaming agents, and thus it is not obvious to produce good quality foams free of surfactants. As shown table 6 below, formulations 001F and 002F containing a mixture of heavy mineral oil and light mineral oil with or without cyclomethicone fail to produce foams and release only liquids from the pressurized canisters. Compounds other than customary surfactants have been identified below that are suitable for the foaming of oleaginous vehicles.

TABLE 6

Oleaginous compositions

| | Formulations | |
|---|---|---|
| | 001F % w/w | 002F % w/w |
| Ingredients | | |
| Heavy mineral oil | 75.00 | 70.00 |
| Light mineral oil | 25.00 | 25.00 |
| Cyclomethicone | — | 5.00 |
| Total | 100.00 | 100.00 |
| Propellant A46 | 12.00 | 12.00 |
| Results | | |
| Foam quality | Poor | Poor |

Silicone oils such as cyclomethicone are included in the formulations primarily as cosmetic agent, for their contribution to skin feeling properties. Volatile cyclomethicones can help reduce the greasy skin feeling that may be present in oleaginous formulations.

Example 7—Surfactant Free Foams Containing Either Fatty Acid or Fatty Alcohol

Two fatty acids were used in combination with heavy mineral oil, light mineral oil and cyclomethicone, and tested for their foaming properties. As described in Table 7a below, formulation 003F containing isostearic acid (a liquid fatty acid) did not give rise to foam but merely generated bubbly liquids. Formulation 004F containing stearic acid (a solid fatty acid) initially produced a fairly good quality foam, but which was not stable and collapsed after 10 seconds. Likewise, compositions containing fatty alcohols produced fairly good quality foams that quickly collapsed (Table 7b). It follows that that fatty acids alone or fatty alcohols alone are not sufficient to stabilize a hydrophobic foam in the absence of a surfactant, even in reasonably high concentrations.

TABLE 7a

Compositions containing a fatty acid

| | Formulations | |
|---|---|---|
| | 003F % w/w | 004F % w/w |
| Ingredients | | |
| Heavy mineral oil | 60.00 | 60.00 |
| Light mineral oil | 25.00 | 25.00 |
| Cyelomethicone | 5.00 | 5.00 |
| Stearic acid (C18) | — | 10.00 |
| Isostearic acid (C18) | 10.00 | — |
| Total | 100.00 | 100.00 |
| Propellant A46 | 12.00 | 12.00 |
| Results | | |
| Foam quality | Fair | Fairly Good |
| Collapse Time (see) | 10 | 10 |
| Foam density (/mL) | — | 0.071 |
| PFF Viscosity (cP) | 58 | 1442 |

TABLE 7b

Compositions containing fatty alcohols

| | Formulations | | | |
|---|---|---|---|---|
| | 005 % w/w | 006 % w/w | 007 % w/w | 009 % w/w |
| Ingredients | | | | |
| Heavy mineral oil | 60.00 | 60.00 | 60.00 | 60.00 |
| | 25.00 | 25.00 | 25.00 | 25.00 |
| Cyclomethicone | 5.00 | 5.00 | 5.00 | 5.00 |
| Myristyl alcohol C 14) | 10.00 | — | — | — |
| Cetyl alcohol (C16) | — | 10.00 | — | — |
| Stearyl alcohol (C18) | — | — | 10.00 | — |
| Behenyl alcohol (C22) | — | — | — | 10.00 |
| Total | 100.00 | 100.00 | 100.00 | 100.00 |
| Propellant A46 | 12.00 | 12.00 | 12.00 | 12.00 |
| Results | | | | |
| Foam quality | Fair | Fair | Fair | Fairly Good |
| Collapse Time (sec) | 10 | 10 | 10 | 10 |
| Foam density (/mL) | — | — | — | 0.160 |
| PFF Viscosity (cP) | 206 | 938 | 585 | 3839 |

Example 8—Surfactant Free Hydrophobic Foam Formulations Containing a Combination of Fatty Acids and Fatty Alcohols Formulations were prepared, containing a combination of fatty acids and fatty alcohols and checked for their foaming properties. As described in Table 8 below, formulations 010 (containing stearic acid and myristyl alcohol) and formulation 017 (containing isostearic acid and stearyl alcohol) did not give rise to quality foams but merely generated bubbly liquids.

However, surprisingly, the combination of stearic acid with cetyl alcohol, stearyl alcohol, cetostearyl alcohol or behenyl alcohol (without any surfactants) gave rise to good quality foams having a fine bubble structure as shown in formulations 011, 012, 013 and 014. Such foams can be successfully produced in the presence or in the absence of silicone oils, as shown in formulation 011 and 016, despite the defoaming effect of silicones. Moreover, formulations 012 and 014 containing a combination of stearic acid with stearyl alcohol or behenyl alcohol give rise to stable foams which did not collapse after 180 sec at 36° C. Thus, it has been discovered that a combination of fatty alcohols and fatty acids has a synergistic effect and possesses effective foaming properties in the case of oleaginous compositions to achieve a thermally stable breakable foam. Interestingly, cetyl and stearyl alcohol achieved the lowest average bubble size, whilst using a combination of the two led to a substantial reduction in viscosity of the pre foam formulation.

TABLE 8

Oleaginous compositions containing various Fatty Acids and Fatty Alcohols

| | Formulation | | | |
|---|---|---|---|---|
| | 010 % w/w | 011 % w/w | 012 % w/w | 013 % w/w |
| Ingredients | | | | |
| Heavy mineral oil | 60.00 | 60.00 | 60.00 | 60.00 |
| Light Mineral oil | 25.00 | 25.00 | 25.00 | 25.00 |
| Cyclomethicone | 5.00 | 5.00 | 5.00 | 5.00 |
| Myristyl alcohol | 5.00 | — | — | — |
| Cetyl alcohol | — | 5.00 | — | — |
| Stearyl alcohol | — | — | 5.00 | — |
| Cetostearyl alcohol | — | — | — | 5.00 |
| Behenyl alcohol | — | — | — | — |
| Isostearic acid | — | — | — | — |
| Stearic acid | 5.00 | 5.00 | 5.00 | 5.00 |
| Total | 100.00 | 100.00 | 100.00 | 100.00 |
| Propellant A46 | 12.00 | 12.00 | 12.00 | 12.00 |
| Propellant AP-70 | — | — | — | — |
| Results | | | | |
| Foam quality | Fair | Good | Good | Good |
| Collapse Time (sec) | 10 | 30 | >180 | 30 |
| Foam density (g/mL) | — | 0.142 | 0.157 | 0.210 |
| Bubble size (micrometers) | — | 60 | 74 | 137 |
| PFF Viscosity (cP) | 107 | 22763 | 23866 | 107 |

| | Formulation | | | |
|---|---|---|---|---|
| | 014 % w/w | 015 % w/w | 016 % w/w | 017 % w/w |
| Ingredients | | | | |
| Heavy mineral oil | 60.00 | 57.00 | 60.00 | 60.00 |
| Light Mineral oil | 25.00 | 25.00 | 30.00 | 25.00 |
| Cyclomethicone | 5.00 | 5.00 | — | 5.00 |
| Myristyl alcohol | — | 3.00 | — | — |
| Cetyl alcohol | — | — | — | — |
| Stearyl alcohol | — | 5.00 | 5.00 | 5.00 |
| Cetostearyl alcohol | — | — | — | — |
| Behenyl alcohol | 5.00 | — | — | — |
| Isostearic acid | — | — | — | 5.00 |
| Stearic acid | 5.00 | 5.00 | 5.00 | — |
| Total | 100.00 | 100.00 | 100.00 | 100.00 |
| Propellant A46 | 12.00 | — | 12.00 | 12.00 |
| Propellant AP-70 | — | 8.00 | — | — |
| Results | | | | |
| Foam quality | Good | Good | Good | Fair |
| Collapse Time (sec) | >180 | >180 | >180 | 10 |
| Foam density (g/mL) | 0.139 | 0.082 | 0.100 | — |
| Bubble size (micrometers) | 139 | — | — | — |
| PFF Viscosity (cP) | 5023 | 18987 | — | — |

Example 9—Surfactant Free Hydrophobic Foam Formulations Containing Fatty Alcohols, Fatty Acids and Waxes Formulations, containing a combination of fatty acids, fatty alcohols and waxes were prepared and checked for their foaming properties. As noted in Table 9a below, formulations 018 containing fatty alcohols and low amounts of stearic acid did not give rise to quality foams but generated fairly good quality foam that very quickly collapsed. Surprisingly, the addition of hydrogenated castor oil and beeswax (in formulation 019) both of which are solid waxes at room temperature enhanced the foam quality and good quality foam that was stable at 36° C. was obtained. Furthermore, formulations containing waxes feel less greasy upon application on skin. Thus, it has been discovered that waxes, in combination with a fatty alcohol and a fatty acid, are useful in producing a high quality foam without surfactants.

TABLE 9a

Hydrophobic foam compositions containing waxes

| | Formulations | |
|---|---|---|
| | 018 % w/w | 019 % w/w |
| Ingredients | | |
| Heavy mineral oil | 63.00 | 59.50 |
| Light mineral oil | 25.00 | 25.00 |
| Cyclomethicone | 5.00 | 5.00 |
| Hydrogenated castor oil | — | 1.50 |
| Beeswax | — | 2.00 |
| Cetostearyl alcohol | 2.50 | 2.50 |
| Stearyl alcohol | 1.50 | 1.50 |
| Behenyl alcohol | 1.00 | 1.00 |
| Stearic acid | 2.00 | 2.00 |
| Total | 100.00 | 100.00 |
| Propellant A46 | 12.00 | 12.00 |
| Results | | |
| Foam quality | Fairly Good | Good |
| Collapse Time (scc) | 10 | 120 |
| Foam density (g/mL) | — | 0.207 |
| Bubble Size micrometers | 155 | 79 |

Additional formulations were prepared, containing waxes alone and in combination with a fatty acid or a fatty alcohol and checked for their foaming properties. As described in Table 9b below, formulations 021, 021b and 022 containing beeswax alone or in combination with hydrogenated castor oil did not give rise to quality foams but merely generated bubbly liquids. Formulations 020 containing hydrogenated castor oil alone generated fairly good quality foam that collapsed after 60 seconds. On the other hand the combination of beeswax, hydrogenated castor oil and fatty alcohol enhanced the foam quality and produced good quality foam that were stable at 36° C. for more than 180 seconds, as shown in formulation 023. However, formulations 024 and 024b composed of combinations of beeswax, hydrogenated castor oil and fatty acid only without fatty alcohol generated fairly good foam that quickly collapsed. This shows the importance of the presence of both fatty alcohols and waxes in oleaginous foam compositions. Additionally, wax such as hydrogenated caster oil or beeswax can not only be used in place of a fatty acid but can be used to facilitate a lower level of fatty acid presence without compromising the foam properties.

TABLE 9b

Hydrophobic foam compositions containing waxes

| Formulations Ingredients | 020 % w/w | 021 % w/w | 021b % w/w | 022 % w/w | 023 % w/w | 024 % w/w | 024b % w/w |
|---|---|---|---|---|---|---|---|
| Heavy mineral oil | 60.00 | 60.00 | 60.00 | 60.00 | 60.00 | 60.00 | 60.00 |
| Light mineral oil | 25.00 | 25.00 | 30.00 | 25.00 | 25.00 | 25.00 | 25.00 |
| Cyclomethicone | 5.00 | 5.00 | — | 5.00 | 5.00 | 5.00 | 5.00 |
| Hydrogenated castor oil | 10.00 | — | — | 5.00 | 2.50 | 2.50 | 5.00 |
| Beeswax | — | 10.00 | 10.00 | 5.00 | 2.50 | 2.50 | 2.50 |
| Stearyl alcohol | — | — | — | — | 5.00 | — | — |
| Stearic acid | — | — | — | — | — | 5.00 | 5.00 |
| Total | 100.00 | 100.00 | 100.00 | 100.00 | 100.00 | 100.00 | 100.00 |
| Propellant A46 | 12.00 | 12.00 | 12.00 | 12.00 | 12.00 | 12.00 | 12.00 |
| Results | | | | | | | |
| Foam quality | Fairly Good | Fair | Fair | Fair | Good | Fairly Good | Fairly Good |
| Collapse Time (sec) | 10 | 10 | 10 | 10 | >180 | 10 | 10 |

Example 10—Tetracycline Foam Formulations Containing Different Hydrophobic Oils

Minocycline foam formulations were prepared containing soybean oil, octyldodecanol, Medium Chain Triglycerides (MCT) oil and coconut oil, which are other examples of hydrophobic oils. Parameters such as foam quality, collapse time and density were evaluated. As described in Table 10, foams of good quality which did not collapse at 36° C. were obtained in different compositions containing these hydrophobic oils. Coconut oil, which on its own is a semi solid paste like oil, was used in combination with liquid soybean oil.

TABLE 10

Foam formulation containing different hydrophobic oils

| Formulations | 199 | 216 | 232A | 235 | 238 | 245 | 248 | 251 | 252 |
|---|---|---|---|---|---|---|---|---|---|
| Heavy mineral oil | 55.89 | 58.82 | — | — | 58.14 | — | — | — | — |
| Light Mineral oil | 25.00 | 25.00 | 25.00 | — | 25.00 | 4.44 | 3.04 | 4.44 | 5.54 |
| Cyclomethicone | 5.00 | 5.00 | 5.00 | 5.00 | 5.00 | 5.00 | 5.00 | 5.00 | 5.00 |

TABLE 10-continued

Foam formulation containing different hydrophobic oils

| Formulations | 199 | 216 | 232A | 235 | 238 | 245 | 248 | 251 | 252 |
|---|---|---|---|---|---|---|---|---|---|
| MCT oil | — | — | — | 48.89 | — | — | — | — | — |
| Octyldodecanol | — | — | — | 12.00 | — | — | — | — | — |
| Coconut oil | — | — | 25.00 | — | — | 23.60 | 25.00 | 21.60 | 25.00 |
| PPG 15 stearyl ether | — | — | — | 15.00 | — | — | — | — | — |
| Soybean oil | — | — | 28.39 | — | — | 50.00 | 50.00 | 50.00 | 50.00 |
| Lanolin. | — | — | — | — | — | — | — | 2.0 | 2.00 |
| Hydrogenated castor oil | — | 1.50 | 2.00 | 2.00 | 1.50 | 2.00 | 2.00 | 2.00 | 2.00 |
| Beeswax | — | 1.87 | 2.50 | 2.50 | 2.00 | 2.00 | 2.00 | 2.00 | 2.00 |
| Cholesterol | — | — | — | — | — | — | 2.50 | — | — |
| Myristyl alcohol | 3.00 | — | — | — | — | 2.50 | 2.50 | — | — |
| Cetostearyl alcohol | — | 2.50 | — | 2.50 | 2.50 | 1.50 | 1.50 | 3.50 | 2.50 |
| Stearyl alcohol | 5.00 | 1.50 | 5.00 | 5.00 | 1.50 | 3.50 | 3.50 | 1.50 | 1.50 |
| Behenyl alcohol | — | 0.70 | 1.00 | 1.00 | 1.00 | 1.10 | 1.10 | 1.10 | 1.10 |
| Aerosil (SiO2) | — | — | — | — | 0.25 | 0.25 | 0.25 | 0.25 | 0.25 |
| Stearic acid | 5.00 | 2.00 | 5.00 | 5.00 | 2.00 | 3.00 | 3.00 | 3.00 | 2.00 |
| Minocycline HCl | 1.11 | 1.11 | 1.11 | 1.11 | 1.11 | 1.11 | 1.11 | 1.11 | 1.11 |
| Total | 100 | 100 | 100 | 100 | 100 | 100 | 100 | 100 | 100 |
| Propellant A46 | — | 12.00 | — | 12.00 | — | 12.00 | 12.00 | 12.00 | 12.00 |
| Propellant A70 | 8.00 | — | 8.00 | — | 8.00 | — | — | — | — |
| Results | | | | | | | | | |
| Foam Quality | G | G | E | E | G | E | E | E | G |
| Collapse Time at 36° C. (sec) | >180 | >180 | 160 | >180 | 150 | >180 | 140 | >180 | >180 |
| Foam Density (g/mL) | 0.082 | 0.225 | 0.149 | 0.293 | 0.237 | 0.295 | 0.211 | 0.223 | 0.167 |

Comments: All the foams were of high quality and had a collapse time at 36° C. in excess of 100 seconds, a foam density of less than 0.3 g/ml and the formulations were able to withstand 4 freeze and thaw cycles and still generate foam of high quality with a collapse time at 36° C. in excess of 100 seconds. The above formulations, without the addition of propellant, are semi-solid gel-like homogeneous compositions where no separation or sedimentation of the ingredients is observed.

Example 11—Tetracycline Foam Formulations Containing a Wax

The foaming properties of formulations containing mineral oil, a paraffin wax, a propellant and a tetracycline were studied. As shown in Table 11 below, formulations containing minocycline HCl, produced breakable foams of quality having a collapse time of more than 1 minute at 36° C., despite the absence of fatty alcohols and fatty acids.

TABLE 11

Tetracycline foam foimulations containing a wax

| Ingredients | Formulations 053D % w/w |
|---|---|
| Heavy mineral oil | 79.0 |
| Paraffin 51-53 | 20.0 |
| Minocycline HCL | 1.0 |
| Total | 100.0 |
| Propellant AP-70 | 8.0 |
| Results | |
| Foam Quality | Excellent |
| Shakability | 2 |
| Collapse Time at 36° C. (sec) | >180 |

Example 12—Petrolatum Based Foamable Compositions

Foam formulations were prepared containing high amounts of Petrolatum, in combination with liquid oils, fatty alcohols and waxes, according to the general manufacturing procedure described in Example 1. As described in Table 12a, quality breakable foams were obtained in different compositions containing Petrolatum. The pre-foam formulations were viscous semi-solid. Upon addition of propellant, the formulations were shakable, indicating that the formulation within the aerosol canister is liquid.

TABLE 12a

Oleaginous Fotinulations containing Petrolatum

| Formulations | A1 | A2 | A3 | A8 |
|---|---|---|---|---|
| White petrolatum | 70.00 | 50.00 | 50.00 | 91.00 |
| Grape seed oil | — | 15.00 | — | — |
| jojoba oil | 15.00 | 15.00 | 15.00 | — |
| Mineral oil | 5.00 | 9.00 | 10.00 | — |
| Wheat germ oil | — | — | 15.00 | — |
| Paraffin wax 51-53 | — | 2.00 | 5.00 | — |
| Beeswax | 1.00 | 1.00 | — | 1.00 |
| Cetostearyl alcohol | 4.00 | 4.00 | 4.00 | 4.00 |
| Hydrogenated castor oil | 3.00 | 2.00 | — | 3.00 |
| Cyclomethicone 5-NF | 1.00 | 1.00 | — | — |
| Behenyl alcohol | 1.00 | 1.00 | 1.00 | 1.00 |
| Total | 100 | 100 | 100 | 100 |
| Propellant A70 | 10.00 | 10.00 | 10.00 | 10.00 |
| Results | | | | |
| Foam Quality | Excellent | Excellent | Excellent | Excellent |
| Foam Density (g/mL) | 0.159 | 0.154 | 0.175 | 0.226 |
| Collapse time at 36° C. (sec) | >180 | >180 | >180 | >180 |
| Mean Bubble size (micrometers) | — | — | 150 | — |

In one or more embodiments, there is provided a foamable formulation comprising Petrolatum, optionally a liquid oil, a fatty alcohol and a wax, wherein the formulation generates quality breakable foam.

Foam formulations were also prepared without waxes, containing high amounts of Petrolatum, in combination with liquid oils and fatty alcohols, according to the general manufacturing procedure described in Example 1. As described in Table 12b, quality breakable foams were obtained in different compositions containing Petrolatum without waxes. The pre-foam formulations were viscous semi-solid. Upon addition of propellant, the formulations were shakable, indicating that the formulation within the aerosol canister is liquid.

TABLE 12b

Oleaginous Formulations containing Petrolatum

| Formulations | A4 | A5 | A6 | A7 |
|---|---|---|---|---|
| White petrolatum | 50.00 | 70.00 | 70.00 | 75.00 |
| Wheat germ oil | — | 10.00 | — | — |
| Jojoba oil | — | 5.00 | — | — |
| Avocado oil | 15.00 | — | — | — |
| Coconut oil | 15.00 | — | — | — |
| Mineral oil | 10.00 | 3.00 | 2000 | 20.00 |
| Shea butter | 5.00 | 5.00 | 5.00 | — |
| C,etostearyl alcohol | 4.00 | 4.00 | 4.00 | 4.00 |
| Cyclomethicone 5-NF | — | 2.00 | — | — |
| Behenyl alcohol | 1.00 | 1.00 | 1.00 | 1.00 |
| Total | 100 | 100 | 100 | 100 |
| Propellant A70 | 10.00 | 10.00 | 10.00 | 10.00 |
| Results | | | | |
| Foam Quality | Good | Excellent | Excellent | Excellent |
| Foam Density (g/mL) | 0.200 | 0.197 | 0.140 | 0.175 |
| Collapse time at 36° C. (sec) | 175 | >180 | >180 | >180 |

In one or more embodiments, there is provided a foamable formulation comprising Petrolatum, and a fatty alcohol with optionally shea butter, wherein the formulation generates quality breakable foam. In one or more embodiments, there is provided a foamable formulation comprising Petrolatum, optionally a liquid oil, and a fatty alcohol with optionally shea butter, wherein the formulation generates quality breakable foam.

Part C—Additional Properties of Tetracycline Compositions

Example 13—Stability of a Tetracycline Antibiotic in Surfactant Free Hydrophobic Formulations Tetracycline antibiotics are known to be very unstable active agents that are degraded by a wide range of commonly used pharmaceutical excipients. For example, it has been found that minocycline is degraded in a few days by different hydrophilic solvents (such as water, glycerin, sodium PCA, propylene glycol and polyethylene glycols), by water dispersed polymers (such as xanthan gum, poloxamers, carbomers, methocel, sodium CMC) and by surfactants (such as polysorbates, sorbitan esters, polyoxyalkyl esters and also lanolin-based surfactants). Thus, the achievement of a long term stable foamable formulation of tetracycline antibiotics described herein was a major challenge and required both extensive research and creativity.

The following example illustrates the physical stability of foams and the chemical stability of minocycline HCl ("MCH") in hydrophobic formulations, namely 238 and 244B as described in Tables 13a, 13b(i) and 13b(ii). In an accelerated stability study, samples were stored at 40° C., and the concentrations of minocycline HCl were determined by HPLC. The stability test results following 2 months, 3 months and 6 months of storage are shown in Tables 13b(i) and 13b(ii).

TABLE 13a

Composition of foam formulation incubated at 40° C.

| | Formulations | |
|---|---|---|
| Ingredients | 238 % w/w | 244B % w/w |
| Heavy mineral oil | 58.14 | — |
| Light mineral oil | 25.00 | 4.44 |
| Cyclomethicone | 5.00 | 5.00 |
| Coconut oil | — | 23.60 |
| Soybean oil | — | 50.00 |
| Lanolin | — | — |
| Hydrogenated castor oil | 1.50 | 2.00 |
| Beeswax | 2.00 | 2.00 |
| Cetos earyl alcohol | 2.50 | 3.50 |
| Stearyl alcohol | 1.50 | 1.50 |
| Bahenyl alcohol | 1.00 | 1.10 |
| Myristyl alcohol | — | 2.50 |
| Aerosil (SiO2) | 0.25 | 0.25 |
| Stearic acid | 2.00 | 3.00 |
| Minocycline HCl | 1.11 | 1.11 |
| Total | 100.00 | 100.00 |
| Propellant A46 | 12.00 | — |
| Propellant AP-70 | 8.00 | — |
| Results | | |
| Foam quality | Excellent | Excellent |
| Collapse Time (sec) | >180 | >180 |
| Foam density (g/mL) | 0.237 | 0.284 |

TABLE 13b(i)

Chemical stability of foam compositions containing minocycline HCl

| | Minocycline content (% of label claim) | | | |
|---|---|---|---|---|
| Formulation | T0 | 2 months at 40° C. | 3 months at 40° C. | 6 months at 40° C. |
| 238 | 98.6 | 95.7 | 96.0 | 92.9 |
| 244B | 98.7 | 97.1 | 93.8 | 90.3 |

NM = not measured

TABLE 13b(ii)

Physical stability of foam compositions containing minocycline HCl

| Formulation | Test | T0 | 2 months at 40° C. | 3 months at 40° C. | 6 months at 40° C. |
|---|---|---|---|---|---|
| 238 | Foam Quality | Excellent | Good | Good | Good |
| | Collapse Time (sec) | >180 | >180 | 160 | NM |
| | Foam Density (g/mL) | 0.237 | 0.259 | 0.289 | 0.263 |
| 244B | Foam Quality | Excellent | Good | Good | Good |
| | Collapse Time (sec) | >180 | >180 | >180 | NM |
| | Foam Density (g/mL) | 0.284 | 0.256 | NM | 0.232 |

NM = not measured

Surprisingly, and despite the known instability of tetracycline antibiotics, the accelerated stability results of both formulations after storage at 40° C. showed minimal degradation of the active agent in the formulations. The formulations disclosed herein thus show an extended accelerated stability for the tetracycline antibiotic and an outstanding physical stability.

These results further illustrate the difficulty, complexity and unexpected and non obvious achievement of discovering surfactant free and water free formulations that are chemically stable and are also physically stable over short term, medium term and or long term periods. Testing and identifying single substances that are compatible chemically with the active agent is not sufficient. Combining multiple substances, which on their own are compatible can lead to collective incompatibility. The discovery and knowledge of substances are chemically compatible does not presume physical stability of the composition or vice-versa. Running a compatibility study between individual formulation components and the active agents does not ensure nor achieve physical stability. Discovering combinations of ingredients that can lead to a physically stable formulation in the absence of surfactant, is itself unexpected.

Example 14—Drug Comparison of the Stability of Minocycline in a Hydrophobic Gel or Foam Formulation Vs. A Reference Gel, on Contact with Skin The objective of this study was to assess the degradation of minocycline following exposure to skin. Two samples were tested:

a. Hydrophobic minocycline formulation #244, containing 25% light mineral oil, 5% cyclomethicone, 25% coconut oil, 28.5% soybean oil (hydrophobic oils); 2% hydrogenated castor oil, 2.5% beeswax (waxes); 5% stearyl alcohol, 1% behenyl alcohol (fatty alcohols), 5% stearic acid (fatty acid and about 1% micronized minocycline HCl b. A reference minocycline gel, which comprised, amongst other components, silicone and ST Elastomer 10, which were mixed prior to application with an additional component that included water, ethanol and propylene glycol.

Samples were applied to freshly retrieved pig's ear skin and stored on a Petri dish, with exposure to air and light for 6 hours at 35° C.; and the concentrations of minocycline HCl and its 4-epi degradant were monitored by liquid chromatography.

As shown in Table 14 below, the reference gel exhibited rapid degradation of minocycline. After 6 hours of exposure the minocycline content decreased by 34% and its 4-epi degradant content reached 19.4%, showing that the reference gel product fails to deliver the all the antibiotic amount to the skin in its active form.

By complete contrast, the "244", surprisingly, and despite the known instability of minocycline, the skin stability results after 6 h showed a very minimal degradation of the active agent: with the content of 4-epi degradant only reached 3.3% and no detectable decrease was observed in the amount of minocycline. Therefore, the foam formulation has an active protective effect on the tetracycline antibiotic upon contact with the skin, and prevents its degradation on the target site of treatment over several hours.

In consequence of these observations, it is contemplated that the hydrophobic breakable composition protects the tetracycline antibiotic from degradation; and therefore it is useful for the treatment of body sites and surfaces which are moist and are exposed top air and/or light, without losing its potency following the application.

As known in the art of medicine, the duration of the effect of a drug relates directly to its residence in the treatment site in its active form; and therefore, it can be concluded that the current hydrophobic breakable tetracycline composition will provide long-term treatment and facilitate administration of the drug in lower frequency, in comparison with other forms of the same drug (if available).

TABLE 14

Skins stability results of compositions containing minocycline HCl

| | Reference Silicone Gel | 244 Formulation |
|---|---|---|
| Initial minocycline skin concentration | 96.90 | 92.20 |
| Initial 4-epi degradant skin concentration | 2.60 | 0.80 |
| Minocycline skin concentration after 6h at 35° C. | 64.00 | 93.70 |
| 4-epi degradant skin concentration after 6h at 35° C. | 19.40 | 3.30 |

Example 15: Safety of the Inactive Ingredients

All inactive ingredients used in the breakable hydrophobic tetracycline formulations are intended for topical use and listed in the current FDA Inactive Ingredient Database; and the concentrations used do not exceed the maximum concentrations given in Database. As an example, Table 15 lays out the acute dose effects of the formulation inactive ingredients of formulation 244, indicating that all these ingredients can be generally regarded as safe (GRAS).

TABLE 15

Acute dose effects of the formutation inactive ingredients of formulation 244

| Ingredient | Toxicity |
|---|---|
| Cyclomethicone | Oral LD50 Rat: >24,134 mg/kg |
| Coconut oil | NA (edible) |
| Soybean oil | IV LD50 Rat: 16.5 g/kg; IV LD50 Mouse: 22.1 g/kg |
| Hydrogenated castor oil | Oral LD50 Rat >10 g/kg |
| Beeswax | Oral LD50 Rat: >5,000mg/kg |
| NI ,fistyl alcohol | Oral LD50 Rat: >10,000 mg/kg; Dermal LD50 Rabbit: >8,000 mg/kg |
| Cetostcatyl alcohol | Oral LD50 Rat: >10,000 mg/kg; Dermal LD50 Rabbit: >8,000 mg/kg |
| Stearyl alcohol | Oral LD50 Rat: >10,000 mg/kg; Dermal LD50 Rabbit: >8,000 mg/kg |
| Behenyl alcohol | Oral LD50 Rat: 12,800 mg/kg |
| Aerosil R 972 (modified silica) | Oral LD50 Brachydanio rerio: >10,000 mg/kg |
| Stearic acid | Oral LD50 Rat: LD50 = 4640; Dermal LD50 Rabbit: >5000 mg/kg |

Example 16: Eye Irritation Studies—HET CAM

The potential of compounds to cause irreversible or severe eye irritation or corrosion may be detected by observing adverse changes, which occur in the chorioallantoic membrane (CAM) of the egg after exposure to test chemicals (Luepke, N. P., Kemper, F. H. "*The HET-CAM Test: An Alternative to the Draize Eye Test.*" Fd Chem. Toxic. (1986) 24, 495-496). Fertilized hen's eggs are rotated in an incubator for 9 days, after which any defective eggs are discarded. The shell around the air cell is removed and the inner membranes are extracted to reveal the chorioallantoic membrane. Test chemicals are added to the membrane and left in contact for up to 5 minutes. The membrane is examined for vascular damage and the time taken for injury to occur is recorded. Irritancy is scored according to the speed at which damage occurs. To validate the HET-CAM data, positive and negative controls and vehicle control, are tested in parallel to the test item.

For each test item, mean scores of replicate eggs is determined. Irritation Score (IS) is interpreted as follows:

| Irritation Score | Irritation Classification |
|---|---|
| 0-0.9 | Non-Irritant |
| 1-4.9 | Slight Irritant |
| 5-8.9 | Moderate Irritant |
| 9-21 | Severe Irritant |

As can be seen in Table 16 using the in vitro irritation HET-CAM, FXFM244 with no dilution, demonstrated no signs of irritation.

TABLE 16

HET CAM studies of formulation 244 with 1% and 4% minocycline

| Treatment | Irritation Score | Classification |
|---|---|---|
| Negative Control | 0 | Non irritant |
| Positive Control | 17.09 | Severe |
| Formulation 244B (1%) | 0 | Non irritant |
| Formulation 244A (4%) | 0 | Non irritant |
| FXFM244-Placebo | 0 | Non irritant |

In consequence of these observations, the hydrophobic breakable tetracycline composition is especially suitable for the treatment of ocular conditions, as well as other conditions that afflict sensitive skin and mucosal membrane areas. Notably, the composition does not include any surfactants, which are known to cause irritation of the eye and additional sensitive areas.

Eye conditions that can be contemplated based on the antimicrobial properties of the tetracycline, plus the anti-inflammatory, anti-oxidative, anti-apoptosis and neuroprotective effects of certain tetracycline compound (such as minocycline and doxycycline) include, in a non limiting fashion can be categorized by their symptoms as follows: eye redness, eye pain or light sensitivity, blurred vision, loss of vision, visual disturbances—floaters, flashing, distortion, halos, etc., itching/burning, tearing/discharge, sensation of something in the eye, eyelid problems, double vision.

Examples of relevant conditions include macular degeneration, age-related macular degeneration, "dry" macular degeneration and "wet" macular degeneration, which are associated with photodamage and apoptosis, cataract, which is associated with apoptosis, glaucoma, open-angle glaucoma, closed-angle glaucoma (associated with optical nerve death and apoptosis), retinopathy, proliferative diabetic retinopathy (apoptosis), macular Edema (inflammation), conjunctivitis, uveitis and trachoma (infection).

Non-limiting examples of ophthalmic conditions that can be treated by a hydrophobic breakable tetracycline composition of the present invention; or such conditions whose complications can be treated by said composition; are provided herewith in their alphabetical order: allergy, blepharitis, cataract, central serous chorioretinopathy, color vision problems, corneal abrasion, corneal edema, corneal ulcer, conjunctivitis, contact lens complications, dacryocystitis, blurred distance vision, dry eye, eale's disease, episcleritis, eyelid ectropion, eyelid entropion, eyelid cellulitis, eye strain, focusing spasm, glaucoma, acute glaucoma, iritis, keratoconus, lyme disease, macular degeneration, macular edema, macular hole, eye medication toxicity, myasthenia gravis, ocular cicatricial pemphigoid, ophthalmic migraine, presbyopia, obstructed tear duct, optic neuritis, optic nerve stroke, orbital fracture, orbital cellulitis, phlyctenulosis, pterygium, recurrent corneal erosion, retinal artery occlusion, retinal detachment, retinal tear, retinal vein occlusion, sarcoidosis, scleritis, sinus disease, strabismus (ocular misalignment), subconjunctival hemorrhage, temporal arteritis, thyroid eye disease, trichiasis, eyelid tumor, twitching of eyelid (eyelid myokymia), uveitis, vitreous detachment and vitreous hemorrhage.

Example 17: In-Vitro Demonstration of Antibacterial Effects of Formulation 244

In an in-vitro study it was revealed that formulation 244 with 1% and 4% minocycline inhibited the growth of *Streptococcus pyogenes, Pseudomonas aeruginosa, Staphylococcus aureus*, as well as a methicillin-resistant strain of *Staphylococcus aureus* (MRSA), as shown in Table 11. The formulation is also effective against *Propionbacterium acnes*, the causative microorganism in acne. A reference antibiotic product, namely Fucidin Ointment (containing 2% fucidic acid) was effective only against the *Streptococcus* strains.

Notably, this effect was observed even though the tetracycline antibiotic is suspended, and is not expected to be readily available for migration on the Petri dish as required for excreting its antimicrobial activity.

TABLE 17

In Vitro Antibacterial Effect: Comparison between formulation 244, Fucidin Ointment and Placebo-Diameter of inhibition (mm)

|  | 244 1% Inhibition Diameter* | 244 4% Inhibition Diameter* | 244 Placebo Inhibition Diameter* | Fucidin Inhibition Diameter* |
|---|---|---|---|---|
| Staphylococcus aureus 6538 | 35, 39, 36 mm | >40 >40 >40 mm | 13, 21, 20 mm | >40, >40, >40 mm |
| Pseudomonas aeruginosa 9027 | 35, 36, 35 mm | 40, 40, 40 mm | 0, 0, 0, mm | 11, 12, 16 mm |
| Staphylococcus aureus MRSA 43300 | 32, 30, 21 mm | >40, >40, >40 mm | 17, 18, 20 mm | 40, 40, 38 mm |
| Streptococcus pyogenes 19615 | 45, 38, 39 mm | 38, 43, 40 mm | 12, 15, 11 mm | 10, 12, 22 mm |
| Propionbacterium acnes | 32, 30, 35 min | 32, 30, 35 mm | NA | NA |

*0 = Ineffective;
≥30 = Very Effective

In consequence of these observations, it is contemplated that the hydrophobic breakable tetracycline composition of the present invention is useful in the treatment of any condition or disease, which can be treated with a gel or a foam, which includes a bacterial component as one of its etiological factors.

In consequence of these observations, the hydrophobic breakable tetracycline composition is especially suitable for the treatment of any condition, which involves as a direct etiological factor or as a secondary complication an infection involving a microorganism which is susceptible to treatment with tetracycline.

Skin conditions that can be contemplated based on the antimicrobial properties of the tetracycline, plus the anti-inflammatory, anti-oxidative and neuroprotective effects of certain tetracycline compound (such as minocycline and doxycycline) include, in a non limiting fashion include, for example: cellulitis, cutaneous abscess, erysipelas, erythrasma, folliculitis, furuncles and carbuncles, hidradenitis suppurativa, impetigo, ecthyma, lymphadenitis, lymphangitis, MRSA infections, necrotizing subcutaneous infection and staphylococcal scalded skin syndrome.

Likewise, the composition of the present invention is suitable for the treatment of any eye condition that involve bacterial infection, vaginal infections, and any additional infections of target sites that may be treated by a gel or a foam.

The same compositions can be applicable in any case of a condition which involves a secondary infection, such as atopic dermatitis and other itching and xerotic conditions.

Example 18: Skin Delivery and Systemic Bioavailability of Minocycline

The transdermal penetration of minocycline was tested using the Franz cell in-vitro diffusion system. This system is commonly used to test the delivery of drugs through the skin from semisolid topical dosage forms. Porcine skin was used according to the OECD Draft New Guideline 428, due to its similar permeation characteristics to human skin. The following experimental parameters were employed:

Two formulations were tested: 244 1% and 244 4% (comprising 1% and 4% Minocycline respectively).

Vertical Franz diffusion cells were used (PermeGear, 1.77 $cm^2$ area, 14 ml receptor fluid).

6 cells were used to test the 4% formulation, 5 cells were used to test the 1% formulation and. One cell was used as a "negative control" (without any applied sample). Approximately 500 mg of product was placed in each cell.

The receiving compartments were sampled at baseline and 3, 6, 9 and 24 hours following application. At the 24 hours time point the skin was processed as follows:

Residues of materials were removed from the skin using filter paper, followed by stripping the skin once using adhesive tape "Scotch Magic® Tape", 3M.

Sequential 19 tapes (9 and 10) should be transferred into two separate vials with 3 mL extraction solution ("Stratum Corneum 1" and "Stratum Corneum 2").

The circular skin area (1.77 $cm^2$) was cut and transferred to a 3 mL extraction solution (Viable skin— VS samples) vial.

TABLE 18

| In Vitro Skin Delivery: Formulation 244 (1% and 4%) | | | | |
|---|---|---|---|---|
| | FX244 foam 1% (n = 5) | | FIVWX244 foam 4% (n = 6) | |
| | Minocycline $\mu g/cm^2$ | STD | Minocycline $\mu g/cm^2$ | STD |
| Stratum Corneum 1 | 7.77 | 4.32 | 33.63 | 20.41 |
| Stratum Corneuni 2 | 0.93 | 0.77 | 7.49 | 8.67 |
| Total Stratum Corneum | 8.70 | 4.97 | 41.12 | 16.89 |
| Viable Skin | 0.79 | 0.19 | 2.00 | 0.81 |
| Total Intradermal Delivery | 9.49 | | 43.12 | 17.48 |
| Receiving Compartment | 0.00 | | 0.00 | |

The following conclusions can be drawn from this experiment

1. Transdermal delivery: Following 24 hours of exposure the amount which was found in the receptor cells was below the limit of quantitation (LOQ) of the analytical method (LOQ=2 µg/mL). This result clearly demonstrates no systemic absorption of the drug from the FMFX244 foam formulation. It can therefore be concluded that topical application of FMFX244 foam should not involve any systemic adverse effects.

2. Intra-dermal delivery (delivery into the skin): The total mean amount of Minocycline in the skin following 24 hours of exposure was 9.5 µg/$cm^2$ for the 1% formulation and 43 µg/$cm^2$ for the 4% formulation. The weight of skin at the delivery area is about 100 mg, which implies that the concentration of Minocycline in the skin following 24 hours of exposure is about 90 µg/gr of skin for the 1% formulation and about 430 µg/gr for the 4% formulation. According to the literature, the minimum inhibitory concentration (MIC) for Minocycline is less than 4 µg/mL, and therefore, it can be concluded that the concentrations found in the skin are sufficient to treat bacterial skin infections.

Notably, this skin penetration profile was observed even though the tetracycline antibiotic is suspended, and is not expected to be readily available for migration into the skin.

In consequence of these observations, the hydrophobic breakable tetracycline composition is especially suitable for the treatment of any skin condition, which occurs in the skin.

Skin conditions that can be contemplated based on the antimicrobial properties of the tetracycline, plus the anti-inflammatory, anti-oxidative, anti-apoptosis and neuroprotective effects of certain tetracycline compound (such as minocycline and doxycycline) include, in a non limiting fashion include, for example: abscess, acne, acne scars, acute febrile neutrophilic dermatosis, allergic contact dermatitis, alopecia, athlete's foot, atopic dermatitis, basal cell carcinoma, blisters, bromhidrosis, burn, calluses candidiasis, carbuncles, cellulitis, chicken pox, cholinergic urticaria, chronic effects of sunlight, cold sores, cold urticaria, comedones, corns, cutaneous abscess, cutaneous larva migrans, cutaneous myiasis, dark spots, delusional parasitosis, dermatitis, dermographism, dermatophytoses, drug eruptions and reactions, dyshidrotic eczema, ecthyma, epidermoid cyst, erysipelas, erysipelas, erythrasma, exfoliative dermatitis, erythema multiforme erythema nodosum, folliculitis, fungal nail infections, furuncles, genital herpes, granuloma annulare, head lice, hidradenitis suppurativa, hives, folliculitis, hirsutism, hyperhidrosis, hypohidrosis, ichthyosis, impetigo, ingrown nails, intertrigo, irritant contact dermatitis, itching, jock itch, keratosis pilaris, lichen simplex chronicus, lichen planus, lichen sclerosus, lymphadenitis, lymphangitis, mastocytosis, measles, melanoma, miliaria, moles, molluscum contagiosum, MRSA, necrotizing subcutaneous infection, nummular dermatitis, oral herpes, panniculitis, parapsoriasis paronychia, photo-allergy, photo-damage, photo-irritation, photosensitivity, papules, perioral dermatitis, pimples, *pityriasis rosea, pityriasis Lichenoides, pityriasis rosea, pityriasis rubra* pilaris, poison ivy, pressure ulcers, pressure urticaria, pruritis, pseudofolliculitis barbae, psoriasis, PUPPP, pustules, pyogenic granuloma, rash, ringworm, rosacea, roseola, rubella, scabies, sebaceous cyst, seborrheic dermatitis, seborrheic keratosis, shingles, skin cancer, skin rash, staphylococcal scalded skin syndrome, stasis dermatitis, Stevens-Johnson syndrome, sunburn, *tinea corporis, tinea cruris, tinea pedis, tinea versicolor*, toxic epidermal necrolysis, varicella zoster virus, vitamin D deficiency, water hives, xerosis, zoster.

Example 19: Ex-Vivo Studies of the Anti-Apoptosis Effects of Formulation 244 with 1% and 4% Minocycline UVB irradiation of the skin is known to decrease cell viability, total antioxidant capacity, while increasing the levels of inflammation (pro-inflammatory cytokines secretion) and epidermal cell apoptosis.
Pre-Treatment with Formulation 244
Specimens of human skin in organ culture were treated topically with Formulation 244 (placebo, 1% and 4% minocycline) for 24 hours, then irradiated with UVB (400 mJ/cm2) and incubated for additional 72 hours. Apoptosis activation was measured 24 h post-irradiation by measuring the extent of caspase 3 activity in epidermal sheets.

Table 19a and Table 19b demonstrate the effect of formulation 244 (with or without minocycline) on epidermal cell apoptosis and viability following UVB irradiation of the skin organ culture. As shown in Table 19a, apoptosis activation was significantly decreased by FXFM244 in a dose-dependant manner.

Cell viability, as measured by the MTT assay 72 hours after irradiation was increased, as shown in Table 19b. One set of mediators implicated in apoptosis belong to the asparate-specific cysteinyl proteases or caspases. A member of this family, caspase-3 has been identified as being a key mediator of apoptosis of mammalian cells. In general terms, as caspase activation increases, a higher percentage of cell death will ensue.

TABLE 19a

Effect of Formulation 244 on apoptosis activation in skin organ culture after UVB irradiation

| | Caspase 3 activity (slope/min) | |
| --- | --- | --- |
| | Non-irradiated | irradiated |
| Carrier | 24 | 177 |
| 244-1% MCH | 4 | 100 |
| 244-4% MCII | 3 | 69 |

TABLE 19b

Effect of Formulation 244 on skin organ culture viability

| | Viability (RFU 540/590 nm) | |
| --- | --- | --- |
| | Non-irradiated | Irradiated |
| Carrier | 6971.25 | 6207.5 |
| 244-1% MCFI | 7615.25 | 8862.25 |
| 244-4% MCH | 8155.5 | 9015.5 |

Comments: It was observed that in the case of cells in contact with a placebo formulation, irradiation causes a decrease in cell viability. On the other hand, in cells in contact with a formulation containing minocycline, higher cell viability was observed both before and after irradiation compared to the placebo, which is a sign of cell regeneration. Therefore, the present formulation comprising minocycline is able to prevent cell death in the case of irradiation and can even stimulate or cause cell regeneration.
Treatment with Formulation 244 after UV Damage Induction
Specimens of human skin in organ culture were irradiated with UVB (400 mJ/cm2) and incubated for additional 72 hours. Formulation 244 4% was then applied to the skin and apoptosis activation was measured 24 h post-treatment by measuring the extent of caspase 3 activity in epidermal sheets.

As shown in Table 19c, Formulation 4% treatment resulted in about 60% decrease in epidermal cell apoptosis.

TABLE 19c

Therapeutic effect of Formulation 244 (application post irradiation)

| | Caspase 3 activity (slope/min) |
| --- | --- |
| Control | 118 |
| 244-4% MCH | 46 |

Conclusion

These results demonstrate that Formulation 244 has protective properties in the case of UVB-induced sun damage or any other condition associated with sunlight or other light (e.g., lazer) exposure. It may therefore be able to reduce skin photodamage and photoaging, and more generally to reduce oxidative stress and inflammation in skin pathologies which are known to be accompanied by apoptotic cell death.

Notably, this skin penetration profile was observed even though the tetracycline antibiotic is suspended, and is not expected to be readily available for migration into the tissue and providing the desirable anti-apoptotic effect.

In consequence of these observations, the hydrophobic breakable tetracycline composition is especially suitable for the treatment of any condition, which includes apoptosis as one of its etiological factors.

Example 20—Compatibility Study

Procedure: Minocycline hydrochloride ("MCH") was incubated as a suspension with various excipients at 25° C. and 40° C. for maximum of sixty days or to the point where degradation was suspected. The ratio between MCH and the tested excipient is detailed below. Visual inspection was the major criterion for indication of compatibility. The color of intact MCH suspension is pale yellow; and any change of color (e.g., to dark orange, red, green, brown and black) indicates oxidation or degradation.

Hydrophilic solvents were tested for compatibility with MCH at a ratio of MCH:excipient of 1:250. dimethyl isosorbide, glycerin, ethanol, propylene glycol, butylene glycol, PEG 200, hexylene glycol, PEG 400, dimethyl sulfoxide and diethylene glycol monoethyl ether were found to be incompatible with MCH.

Oily emollients and waxes were tested for compatibility with MCH at a ratio of MCH:excipient of 1:250 for Oily emollients and 1:50 for waxes. Hydrogenated castor oil, castor oil, cocoglycerides, disopropyl adipate, mineral oil, coconut oil, beeswax, MCT oil, cyclomethicone, isododecane, cetearyl octanoate, gelled mineral oil, isopropyl myristate, PPG 15 stearyl ether, mineral oil heavy, octyl dodecanol, white petrolatum, petrolatum, paraffin 51-53, paraffin 58-62, calendula oil, shea butter, grape seed oil, almond oil, jojoba oil, avocado oil, peanut oil, wheat germ oil and hard fat were found to be compatible with MCH. Pomegranate seed oil was found to be incompatible with MCH.

The compatibility of MCH with hydrophobic surfactant was tested following solubilization of the surfactant in mineral oil (mineral oil was previously shown to be compatible with MCH). Surfactants were tested for compatibility with MCH at a ratio of MCH:excipient of 1:50. PEG 150 distearate, laureth 4, PEG 40 hydrogenated castor oil, PEG 75 lanolin, glucam P20 distearate, PEG 100 stearate, glyceryl monostearate, PEG 40 stearate, montanov S (cocoyl alcohol (and) C12-20 alkyl glucoside)), alkyl lactate, benton gel, SPAN 60, sorbitan sesquistearate, SPAN 40, SPAN 80, Tween 20, Tween 60, ceteth 2, sucrose stearic acid esters D1813, ceteareth 20, steareth 2/steareth 21, methyl glucose sesquistearate, Oleth 20, and PPG 20 methyl glucose ether were found to be incompatible with MCH. Sucrose stearic acid esters D1803, sucrose stearic acid esters D1807 and sucrose stearic acid esters D1811 were found to be compatible with MCH; however, not all of them dissolved in oil (e.g. 1811, 1813).

Foam adjuvants were tested for compatibility with MCH at a ratio of MCH:excipient of 1:50. Isostearyl alcohol, behenyl alcohol, stearyl alcohol, cetyl alcohol, oleyl alcohol, myristyl alcohol, cetostearyl alcohol, palmitic acid, stearic acid and oleic acid were found to be compatible with MCH. Isostearic acid was not compatible with MCH.

Additives were tested for compatibility with MCH at a ratio of MCH:excipient of 1:50. Aerosil and Menthol were found to be compatible with MCH. Titanium dioxide and Ethocel were not compatible with MCH.

Additives were tested for compatibility with MCH. Minimal quantities of water (100 µL) were added to MCH, suspended in excipients that had demonstrated compatibility to examine whether water can enhance oxidation/degradation in the absence or presence of antioxidant. In parallel, antioxidants were added to the MCH suspensions comprising water. Antioxidants were also added to excipients which were found to be non compatible with MCH. Addition of water caused prompt degradation of MCH. Addition of the antioxidants alpha-tocopherol, BHA/BHT and propyl gallate did not prevent MCH degradation. Compatible excipients became incompatible in the presence of water. Addition of antioxidants did not alter this result.

Example 21—Color and Pigmentation Study

Part A—Color Change

Samples of formulations 238 and 216 with 1% minocycline were incubated during 3 months at 25° C., 30° C. and 40° C. Following this period the foam product was actuated and the change in color was observed. Minimal to no change was observed following 3 months storage at all three temperatures.

Part B—Pigmentation

A large amount of MCH 244 4% was actuated on human skin to observe whether any skin pigmentation occurs. Minimal to no skin pigmentation following rubbing the foam onto the skin was noticed, when observed after about 30 seconds.

What is claimed is:

1. A method of treating rosacea, comprising administering a waterless foam composition comprising a minocycline and a foamable carrier, the carrier comprising:
    a) at least one hydrophobic oil; and
    b) an agent comprising (i) at least one fatty alcohol and at least one wax; (ii) at least one fatty acid and at least one wax; (iii) at least one fatty alcohol, at least one fatty acid, and at least one wax; (iv) a wax comprising a hydrogenated oil; or (v) a combination of two or more waxes;
    wherein the composition does not contain one or more minocycline incompatible substance selected from the group consisting of dimethyl sulfoxide (DMSO), dimethylformamide (DMF), acetonitrile, acetone, methyl ethyl ketone, 1,4-dioxane, tetrahydrofuran (THF), N-methylpyrrolidone, pyridine, piperidine, N-methyl-2-pyrrolidone and 1-methyl-2-pyrrolidinone), azone (1-dodecylazacycloheptan-2-one), dimethyl isosorbide, glycerin, ethanol, propylene glycol, butylene glycol, PEG 200, hexylene glycol, PEG 400, diethylene glycol monoethyl ether, pomegranate seed oil, isostearic acid, and ethylcellulose;
    wherein the composition does not contain a surfactant; and
    wherein the composition does not contain a polyol.

2. The method of claim 1, wherein the at least one hydrophobic oil comprises a mineral oil, a cocoglyceride, a silicone oil, a liquid paraffin, a caprylic/capric triglyceride, a coconut oil, a soybean oil, a cyclomethicone, disopropyl adipate isododecane, cetearyl octanoate, a gelled mineral oil, isopropyl myristate, PPG 15 stearyl ether, octyl dodecanol, a petrolatum, a calendula oil, a grape seed oil, an almond oil, a jojoba oil, an avocado oil, a peanut oil, a wheat germ oil, or a mixture of any two or more thereof.

3. The method of claim 1, wherein at least one or both of the fatty alcohol and the fatty acid has at least 12 carbon atoms in its carbon backbone.

4. The method of claim 1, wherein the agent comprises at least one fatty alcohol, at least one fatty acid, and at least one wax, wherein the at least one wax comprises a beeswax, a hydrogenated oil, or both.

5. The method of claim 1, wherein the composition contains less than 0.4% by weight of a protic solvent, a polar aprotic solvent, and a silicone thickening agent, or wherein the composition contains less than 0.4% by weight of a polymeric gelling agent, a short chain alcohol, and a silicone thickening agent.

6. The method of claim 1, wherein the minocycline is minocycline hydrochloride.

7. The method of claim 1, wherein the foamable carrier comprises:
    a) 45% to 55% by weight of a soybean oil;
    b) 21.2% to 26% by weight of a coconut oil;
    c) 4.5% to 5.5% by weight of a cyclomethicone;
    d) 0.85% to 4.8% by weight of a light mineral oil;
    e) 3.2% to 3.9% by weight of cetostearyl alcohol;
    f) 2.7% to 3.3% by weight of stearic acid;
    g) 2.3% to 2.8% by weight of myristyl alcohol;
    h) 1.8% to 2.2% by weight of hydrogenated castor oil;
    i) 1.8% to 2.2% by weight of beeswax;
    j) 1.4% to 1.7% by weight of stearyl alcohol; and
    k) 1% to 1.2% by weight of behenyl alcohol.

8. The method of claim 1, wherein the minocycline is present at about 1% to about 10% of the composition.

9. The method of claim 1, wherein the minocycline is present at about 1.5% or about 3% of the composition.

10. The method of claim 1, wherein the composition is free of or comprises less than 10% petrolatum by weight of the composition.

11. The method of claim 1, wherein the at least one hydrophobic oil is about 60% to about 99% by weight of the composition.

12. The method of claim 1, wherein the composition is administered at least once daily.

13. The method of claim 1, wherein the composition is administered at least once daily and the minocycline is present at about 1.5% or about 3% of the composition.

14. The method of claim 1, wherein the foam composition is produced with a liquefied or compressed gas propellant.

15. The method of claim 1, wherein the at least one hydrophobic oil comprises a hydrocarbon oil, an ester oil, an ester of a dicarboxylic acid, a triglyceride oil, an unsaturated or polyunsaturated oil, an essential oil, a canola oil, a castor oil, a corn oil, a cotton oil, a cottonseed oil, glycerol, an olive oil, a palm oil, a dimethicone, a fatty acid-modified silicone oil, or a mixture of any two or more thereof.

16. A method of treating rosacea, comprising administering
   a waterless composition comprising
   a carrier and 1% to 10% by weight of the composition of a minocycline, wherein the carrier comprises:
   a) at least one hydrophobic oil; and
   b) an agent comprising (i) at least one fatty alcohol and at least one wax; (ii) at least one fatty acid and at least one wax; (iii) at least one fatty alcohol, at least one fatty acid, and at least one wax; (iv) a wax comprising a hydrogenated oil; or (v) a combination of two or more waxes;
   wherein the composition does not contain a surfactant; and
   wherein the composition does not contain a polyol.

17. The method of claim 16, wherein the minocycline is minocycline hydrochloride and is present at an amount of about 1.5% or about 3% by weight of the composition.

18. The method of claim 16, wherein the agent comprises at least one fatty alcohol, at least one fatty acid, and at least one wax.

19. The method of claim 16, wherein the composition is a foam composition, and wherein the foam composition is produced upon addition of a liquefied or compressed gas propellant to the carrier.

20. The method of claim 16, wherein the carrier comprises:
   a) 45% to 55% by weight of a soybean oil;
   b) 21.2% to 26% by weight of a coconut oil;
   c) 4.5% to 5.5% by weight of a cyclomethicone;
   d) 0.85% to 4.8% by weight of a light mineral oil;
   e) 3.2% to 3.9% by weight of cetostearyl alcohol;
   f) 2.7% to 3.3% by weight of stearic acid;
   g) 2.3% to 2.8% by weight of myristyl alcohol;
   h) 1.8% to 2.2% by weight of hydrogenated castor oil;
   i) 1.8% to 2.2% by weight of beeswax;
   j) 1.4% to 1.7% by weight of stearyl alcohol; and
   k) 1% to 1.2% by weight of behenyl alcohol.

21. A method of treating rosacea, comprising administering
   a foam produced from a foamable composition comprising
   a carrier and a liquified or compressed gas propellant, the carrier comprising:
   a) a tetracycline antibiotic;
   b) a combination of two or more hydrophobic oils, wherein at least one of the hydrophobic oils is a light mineral oil and the other hydrophobic oil comprises a heavy mineral oil, soybean oil, and/or coconut oil; and
   c) a combination of two or more fatty alcohols, wherein at least one of the fatty alcohols is stearyl alcohol;
   wherein the hydrophobic oils are present at between about 70% and 95% by weight of the carrier; and
   wherein the ratio of the carrier to the propellant is between about 100:1 and about 100:25.

22. The method of claim 21, wherein the foamable composition further comprises stearic acid, wherein the ratio of the fatty alcohols to stearic acid is between about 4:1 and 1:4.

23. The method of claim 21, wherein the tetracycline antibiotic comprises minocycline.

24. The method of claim 23, wherein the minocycline is present at about 1.5% to about 3% by weight of the carrier.

25. The method of claim 21, wherein the carrier further comprises at least one wax, wherein the wax is selected from the group consisting of a beeswax, a hydrogenated castor oil, a paraffin 58-62° C. wax, a paraffin 51-53° C. wax, a paraffin 42-44° C. wax, and a mixture of two or more thereof.

26. The method of claim 25, wherein the fatty alcohols and the wax are present at a ratio between about 4:1 and 3:2.

27. The method of claim 21, wherein the combination of the hydrophobic oils comprises a light mineral oil, a soybean oil, a coconut oil, and cyclomethicone.

28. The method of claim 21, wherein the combination of the fatty alcohols comprises stearyl alcohol, cetostearyl alcohol, behenyl alcohol, and myristyl alcohol.

29. A method of treating rosacea, comprising administering
   a foam produced from a foamable composition comprising
   a carrier and a liquified or compressed gas propellant, the carrier comprising:
   a) a minocycline;
   b) a combination of two or more hydrophobic oils, wherein at least one of the hydrophobic oils is a light mineral oil and the other hydrophobic oil comprises a heavy mineral oil, soybean oil, and/or coconut oil;
   c) a combination of two or more fatty alcohols, wherein at least one of the fatty alcohols is stearyl alcohol; and
   d) at least one wax;
   wherein the hydrophobic oils are present at between about 70% and 95% by weight of the carrier;
   wherein the fatty alcohols and the wax are present at a ratio between about 4:1 and 3:2; and
   wherein the ratio of the carrier to the propellant is between about 100:1 and about 10025.

30. The method of claim 29, wherein the carrier further comprises a stearic acid and wherein the ratio of the fatty alcohols to stearic acid is between about 4:1 and 1:4.

* * * * *